United States Patent [19]
Bombrun

[11] Patent Number: 6,043,252
[45] Date of Patent: Mar. 28, 2000

[54] CARBOLINE DERIVATIVES

[75] Inventor: Agnes Bombrun, Paris, France

[73] Assignee: Icos Corporation, Bothell, Wash.

[21] Appl. No.: 09/154,052

[22] Filed: Sep. 16, 1998

Related U.S. Application Data

[63] Continuation-in-part of application No. PCT/EP97/02277, May 5, 1997.

[51] Int. Cl.$^7$ .................................................. A61K 31/44
[52] U.S. Cl. ............................................ 514/292; 546/85
[58] Field of Search ................................ 514/292; 546/85

[56] References Cited

U.S. PATENT DOCUMENTS

| | | | |
|---|---|---|---|
| 4,801,587 | 1/1989 | Voss et al. ............................... | 514/248 |
| 5,770,606 | 6/1998 | El-Rashidy et al. .................... | 514/284 |
| 5,874,437 | 2/1999 | Garvey et al. .......................... | 514/258 |

*Primary Examiner*—Dwayne C. Jones
*Assistant Examiner*—C. Delacroix-Muirheid

*Attorney, Agent, or Firm*—Marshall, O'Toole, Gerstein, Murray & Borun

[57] ABSTRACT

Carboline derivatives of formula (I)

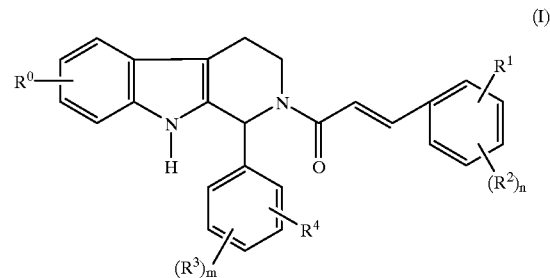

are potent and selective inhibitors of cyclic guanosine 3',5'-monophosphate specific phosphodiesterase (cGMP-specific PDE) and have utility in a variety of therapeutic areas where such inhibition is thought to be beneficial, including the treatment of cardiovascular disorders and erectile dysfunction.

14 Claims, No Drawings

CARBOLINE DERIVATIVES

CROSS-REFERENCE TO RELATED APPLICATION

This is a continuation-in-part application of PCT/EP97/02277, filed May 5, 1997.

FIELD AND BACKGROUND OF THE INVENTION

This invention relates to a series of carboline derivatives, to processes for their preparation, to pharmaceutical compositions containing them, and to their use as therapeutic agents. In particular, the invention relates to carboline derivatives which are potent and selective inhibitors of cyclic guanosine 3',5'-monophosphate specific phosphodiesterase (cGMP-specific PDE) having utility in a variety of therapeutic areas where such inhibition is considered beneficial, including the treatment of cardiovascular disorders and erectile dysfunction.

SUMMARY OF THE INVENTION

Thus, according to a first aspect, the present invention provides compounds of formula (I)

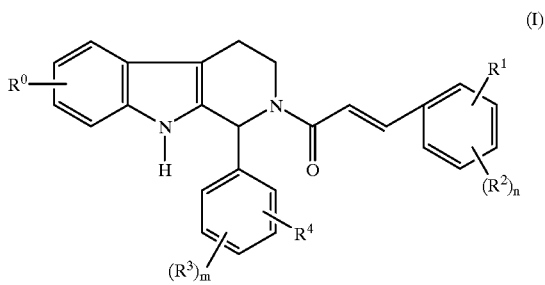

(I)

wherein
$R^0$ represents hydrogen or halogen;
$R^1$ is selected from the group consisting of:
hydrogen,
$NO_2$,
trifluoromethyl,
trifluoromethoxy,
halogen,
cyano,
a 5- or 6-membered heterocyclic group containing at least one heteroatom selected from oxygen, nitrogen and sulphur, and is optionally substituted by —$C(=O)OR^a$ or $C_{1-4}$alkyl,
$C_{1-6}$alkyl optionally substituted by —$OR^a$,
$C_{1-3}$alkoxy,
$C(=O)R^a$,
$O$—$C(=O)R^a$,
$C(=O)OR^a$,
$C_{1-4}$alkylene$C(=O)OR^a$,
$O$—$C_{1-4}$alkylene-$C(=O)OR^a$,
$C_{1-4}$alkylene-$O$—$C_{1-4}$alkylene-$C(=O)OR^a$,
$C(=O)NR^aSO_2R^c$,
$C(=O)C_{1-4}$alkyleneHet,
$C_{1-4}$alkyleneNR$^a$R$^b$,
$C_{2-6}$alkenyleneNR$^a$R$^b$,
$C(=O)NR^aR^b$,
$C(=O)NR^aR^c$,
$C(=O)NR^aC_{1-4}$alkyleneOR$^b$
$C(=O)NR^aC_{1-4}$alkyleneHet,
$OR^a$
$OC_{2-4}$alkylene NR$^a$R$^b$,
$OC_{1-4}$alkylene-CH(OR$^a$)CH$_2$NR$^a$R$^b$,
$O$—$C_{1-4}$alkylene Het,
$O$—$C_{2-4}$alkylene-OR$^a$,
$O$—$C_{2-4}$alkylene-NR$^a$—C(=O)OR$^b$,
NR$^a$R$^b$,
NR$^a$C$_{1-4}$alkyleneNR$^a$R$^b$,
NR$^a$C(=O)R$^b$,
NR$^a$C(=O)NR$^a$R$^b$,
N(SO$_2$C$_{1-4}$alkyl)$_2$,
NR$^a$(SO$_2$C$_{1-4}$alkyl),
SO$_2$NR$^a$R$^b$, and
OSO$_2$trifluoromethyl;
$R^2$ is selected from the group consisting of:
hydrogen,
halogen,
OR$^a$,
$C_{1-6}$alkyl,
$NO_2$, and
NR$^a$R$^b$,
or $R^1$ and $R^2$ are taken together to form a 3- or 4-membered alkylene or alkenylene chain component of a 5- or 6-membered ring, optionally containing at least one heteroatom;
$R^3$ is selected from the group consisting of:
hydrogen,
halogen,
$NO_2$,
trifluoromethoxy,
$C_{1-6}$alkyl, and
$C(=O)OR^a$;
$R^4$ is hydrogen,
or $R^3$ and $R^4$ are taken together to form a 3- or 4-membered alkylene or alkenylene chain component of a 5- or 6-membered ring, optionally containing at least one heteroatom;
Het represents a 5- or 6-membered heterocyclic group containing at least one heteroatom selected from the group consisting of oxygen, nitrogen, and sulfur, and is optionally substituted with $C_{1-4}$alkyl;
$R^a$ and $R^b$ can be the same or different, and are independently selected from hydrogen and $C_{1-6}$alkyl;
$R^c$ represents phenyl or $C_{4-6}$cycloalkyl, wherein the phenyl or $C_{4-6}$cycloalkyl can be optionally substituted by one or more halogen atoms, one or more —$C(=O)OR^a$, or one or more —$OR^a$;
n is an integer selected from 1, 2 and 3;
m is an integer selected from 1 and 2;
and pharmaceutically acceptable salts and solvates (e.g., hydrates) thereof.

The term alkyl or alkylene as used herein respectively contains the indicated number of carbon atoms and includes straight chained and branched alkyl or alkylene groups, typically methyl, methylene, ethyl, and ethylene groups, and straight chained and branched propyl, propylene, butyl, and butylene groups. The term $C_{2-6}$alkenylene as used herein contains 2 to 6 carbon atoms and includes straight chained and branched alkenylene groups, in particular ethenylene or the like.

The terms $C_{4-6}$ cycloalkyl denotes cyclic groups containing 4 to 6 carbon atoms, namely cyclobutane, cyclopentane, and cyclohexane.

The term halogen as used herein includes fluorine, chlorine, bromine, and iodine.

The term 5- or 6-membered heterocyclic group as used herein includes 5- or 6- membered heterocycloalkyl and heteroaryl groups, e.g., tetrahydrofuranyl, piperidyl, piperazinyl, pyrrolidinyl, morpholinyl, pyridyl, imidazolyl, furyl, and tetrazolyl.

Appropriately, $R^0$ represents hydrogen. Alternatively, $R^0$ can represent halogen, in particular fluorine.

$R^1$ can represent any of the substituents as hereinbefore described, or more particularly can represent any of —$OR^a$, —O—$C_{2-4}$alkyleneNR$^a$R$^b$, —O—$C_{1-4}$alkyleneHet and —O—$C_{2-4}$alkylene-OR$^a$. In particular, $R^1$ represents —O—$C_{2-4}$alkyleneNR$^a$R$^b$, wherein $C_{2-4}$alkylene can represent ethylene, and, $R^a$ and $R^b$ can independently represent methyl. Particularly suitably $R^2$ represents hydrogen. Alternatively, in the case where $R^1$ and $R^2$ together form a 3- or 4-membered alkylene or alkenylene chain component of a 5- or 6-membered ring, optionally containing at least one heteroatom as hereinbefore described, $R^1$ and $R^2$ together form a methylenedioxy chain, an ethyleneoxy chain, an ethylenedioxy chain, an ethenyleneoxy chain, a propylene chain, a butylene chain or —NR$^a$ethylene-O- . Aptly, $R^1$ and $R^2$ together form methylenedioxy, propylene, or —N(CH$_3$)—(CH$_2$)$_2$—O—.

Suitably $R^3$ and $R^4$ taken together form a 3- or 4-membered alkylene or alkenylene chain component of a 5- or 6-membered ring, optionally containing at least one heteroatom as hereinbefore described. Particularly $R^3$ and $R^4$ together form a methylenedioxy chain, an ethyleneoxy chain, an ethylenedioxy chain, an ethenyleneoxy chain, a propylene chain, a butylene chain, or —NR$^a$ethylene-O—. Aptly $R^3$ and $R^4$together form a methylenedioxy chain, an ethyleneoxy chain, an ethylenedioxy chain, an ethenyleneoxy chain, or a propylene chain. In particular, $R^3$ and $R^4$ together form methylenedioxy or ethyleneoxy, most particularly ethyleneoxy.

A particular subgroup of compounds according to the present invention can be represented by formula (Ia)

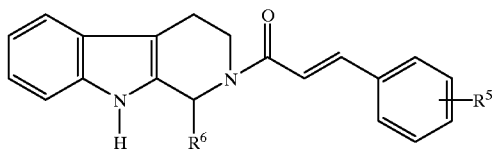

(Ia)

wherein $R^5$ is selected from the group consisting of —OH, —OC$_{2-4}$alkylene NR$^a$R$^b$, and O—C$_{1-4}$alkylene Het, wherein Het is as hereinbefore described, and $R^6$ represents

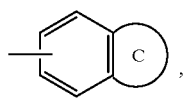

wherein C represents a 5- or 6-membered ring which can be saturated or partially or fully unsaturated, and comprises carbon atoms and optionally one or two heteroatoms selected from oxygen, sulphur and nitrogen, optionally substituted by $C_{1-4}$alkyl;

and pharmaceutically acceptable salts and solvates (e.g., hydrates thereof).

Typically, $R^5$ represents —OC$_{2-4}$alkylene NR$^a$R$^b$, in particular —OCH$_2$CH$_2$N(CH$_3$)$_2$. Alternatively, $R^5$ can represent —O—$C_{1-4}$alkylene Het, where Het can be piperidyl, pyrrolidinyl (optionally substituted by $C_{1-4}$alkyl, e.g., methyl) or morpholinyl.

Particularly $R^6$ represents

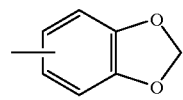

or

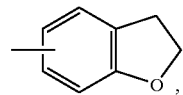

especially

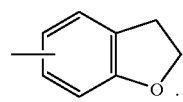

The compounds of formula (I) can contain one or more asymmetric centers and thus can exist as enantiomers or diastereoisomers. It is to be understood that the invention includes both mixtures and separate individual isomers of the compounds of formula (I).

The pharmaceutically acceptable salts of the compounds of formula (I) which contain a basic center are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulphonate, benzenesulphonate and p-toluenesulphonate salts. Compounds of the formula (I) can also provide pharmaceutically acceptable metal salts, in particular alkali metal salts, with bases. Examples include the sodium and potassium salts.

Particular individual compounds of the invention include:

(E)-1-(1-Phenyl-1,3,4,9-tetrahydro-β-carbolin-2-yl)-3-phenylpropene-1-one (E)-1-(1-Phenyl-1,3,4,9-tetrahydro-β-carbolin-2-yl)-3-(4-nitrophenyl)propene-1-one (E)-1-(1-Phenyl-1,3,4,9-tetrahydro-β-carbolin-2-yl)-3-(4-trifluoromethylphenyl)propene-1-one (E)-1-(1-Phenyl-1,3,4,9-tetrahydro-β-carbolin-2-yl)-3-(4-methoxyphenyl)propene-1-one (E)-1-[1-(4-Methoxyphenyl)-1,3,4,9-tetrahydro-β-carbolin-2-yl]-3-(4-trifluoromethylphenyl)propene-1-one (E)-N-[4-[3-Oxo-3-(1-phenyl-1,3,4,9-tetrahydro-β-carbolin-2-yl)propenyl]phenyl]acetamide (E)-1-[1-(4-Methoxyphenyl)-1,3,4,9-tetrahydro-β-carbolin-2-yl)-3-phenylpropene-1-one (E)-1-[1-(3,4-Methylenedioxyphenyl)-1,3,4,9-tetrahydro-β-carbolin-2-yl]-3-phenylpropene-1-one (E)-1-(1-Phenyl-1,3,4,9-tetrahydro-β-carbolin-2-yl)-3-(4-formylphenyl)propene-1-one (E)-N-[4-[3-Oxo-3-(1-(4-nitrophenyl)-1,3,4,9-tetrahydro-β-carbolin-2-yl)propenyl]phenyl]acetamide (E)-1-[1-(4-Nitrophenyl)-1,3,4,9-tetrahydro-β-carbolin-2-yl]-3-phenylpropene-1-one (E)-1-[1-(4-Trifluoromethoxyphenyl)-1,3,4,9-tetrahydro-β-carbolin-2-yl]-3-phenylpropene-1-one (E)-1-[1-(4-Methylphenyl)-1,3,4,9-tetrahydro-β-carbolin-2-yl]-3-phenylpropene-1-one (E)-N-[4-[3-Oxo-3-(1-(3,4-methylenedioxyphenyl)-1,3,4,9-tetrahydro-β-carbolin-2-yl)-propenyl]phenyl]acetamide (E)-4-[3-Oxo-3-(1-phenyl-1,3,4,9-tetrahydro-β-carbolin-2-yl)-propenyl]benzoic acid, methyl ester (E)-1-[1-(2-Chlorophenyl)-1,3,4,9-tetrahydro-β-carbolin-2-yl]-3-phenylpropene-1-one (E)-1-(1-Phenyl-1,3,4,9-tetrahydro-β-carbolin-2-yl)-3-(3,4-methylenedioxyphenyl)-propene-1-one (E)-1-[1-(3,4-Methylenedioxyphenyl)-1,3,4,9-tetrahydro-β-carbolin-2-yl]-3-(4-bromophenyl)-propene-1-one (E)-1-[1-(4-Chlorophenyl)-1,3,4,9-tetrahydro-β-carbolin-2-yl]-3-phenylpropene-1-one (E)-1-[1-(3,4-Methylenedioxyphenyl)-1,3,4,9-tetrahydro-β-carbolin-2-yl]-3-(4-ethoxyphenyl)propene-1-one (E)-4-[3-Oxo-3-(1-(3,4-methylenedioxyphenyl)-1,3,4,9-tetrahydro-β-carbolin-2-yl)propenyl]acetic acid, phenyl ester (E)-1-[1-(3,4-Methylenedioxyphenyl)-1,3,4,9-tetrahydro-β-carbolin-2-yl]-3-(4-hydroxyphenyl)propene-1-one (E)-1-[1-(3,4-Methylenedioxyphenyl)-1,3,4,9-tetrahydro-β-carbolin-2-yl]-3-(4-formylphenyl)propene-1-one (E)-1-[4-[3-Oxo-3-(1-(3,4-methylenedioxyphenyl)-1,3,4,9-tetrahydro-β-carbolin-2-yl)-propenyl]phenyl]-3-phenylurea (E)-1-(3,4-Methylenedioxyphenyl)-1,3,4,9-tetrahydro-β-carbolin-2-yl]-3-(4-aminophenyl)-propene-1-one (E)-1-[1-(3,4-Methylenedioxy-phenyl)-1,3,4,9-tetrahydro-β-carbolin-2-yl]-3-(4-nitrophenyl)-propene-1-one (E)-1-[1-(3,4-Methylenedioxyphenyl)-1,3,4,9-tetrahydro-β-carbolin-2-yl]-3-[(4-bis(methylsulfonyl)-aminophenyl]-propene-1-one (E)-4-[3-Oxo-3-[1-(3,4-methylenedioxyphenyl)-1,3,4,9-tetrahydro-β-carbolin-2-yl]-propenyl]benzoic acid, methyl ester (E)-N-[4-[3-Oxo-3-[1-(3,4-methylenedioxyphenyl)-1,3,4,9-tetrahydro-β-carbolin-2-yl]propenyl]phenyl]methanesulfonamide (E)-4-[3-Oxo-3-[1-(3,4-methylenedioxyphenyl)-1,3,4,9-tetrahydro-β-carbolin-2-yl]propenyl]benzamide]

(E)-4-[3-Oxo-3-[1-(3,4-methylenedioxyphenyl)-1,3,4,9-tetrahydro-β-carbolin-2-yl]-propenyl]benzoic acid (E)-1-[1-(3,4-Methylenedioxyphenyl)-1,3,4,9-tetrahydro-β-carbolin-2-yl]-3-(4-cyanophenyl)propene-1-one (E)-1-[1-(3,4-Methylenedioxyphenyl)-1,3,4,9-tetrahydro-β-carbolin-2-yl]-3-(4-trifluoromethylphenyl)propene-1-one (E)-1-[1-(3,4-Methylenedioxyphenyl)-1,3,4,9-tetrahydro-β-carbolin-2-yl]-3-(3,4-methylenedioxyphenyl)propene-1-one (E)-1-[1-(3,4-Methylenedioxyphenyl)-1,3,4,9-tetrahydro-β-carbolin-2-yl]-3-(4-chlorophenyl)-propene-1-one (E)-1-[1-(3,4-Methylenedioxyphenyl)-1,3,4,9-tetrahydro-β-carbolin-2-yl]-3-(4-trifluoromethoxyphenyl)propene-1-one (E)-1-[1-(3,4-Methylenedioxyphenyl)-1,3,4,9-tetrahydro-β-carbolin-2-yl]-3-(4-methylphenyl)propene-1-one (E)-[4-[3-Oxo-3-(1-(3,4-methylenedioxyphenyl)-1,3,4,9-tetrahydro-β-carbolin-2-yl)propenyl]phenyl]urea (E)-1-[1-(3,4-Methylenedioxyphenyl)-1,3,4,9-tetrahydro-β-carbolin-2-yl]-3-(4-hydroxymethylphenyl)propene-1-one (E)-N-Benzyl-4-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-(2,4-dichlorophenyl)propene-1-one (E)-1-[1-(3,4-Methylenedioxyphenyl)-1,3,4,9-tetrahydro-β-carbolin-2-yl]-3-(3-methoxy-4-hydroxyphenyl)propene-1-one (E)-1-[1-(3,4-Methylenedioxyphenyl)-1,3,4,9-tetrahydro-β-carbolin-2-yl]-3-(3-hydroxy-4-methoxyphenyl)propene-1-one (E)-1-[1-(3,4-Methylenedioxyphenyl)-1,3,4,9-tetrahydro-β-carbolin-2-yl]-3-(4-fluorophenyl)-propene-1-one (E)-1-[1-(3,4-Methylenedioxyphenyl)-1,3,4,9-tetrahydro-β-carbolin-2-yl]-3-indan-5-yl-1-propene-1-one (E)-N-[4-[3-Oxo-3-(1-(3,4-methylenedioxyphenyl)-1,3,4,9-tetrahydro-β-carbolin-2-yl)propenyl]benzoyl]benzenesulfonamide (E)-1-[1-(3,4-Methylenedioxyphenyl)-1,3,4,9-tetrahydro-β-carbolin-2-yl]-3-(3,4-dichlorophenyl)propene-1-one (E)-1-[1-(3,4-Methylenedioxyphenyl)-1,3,4,9-tetrahydro-β-carbolin-2-yl]-3-(3,4-dimethoxyphenol)propene-1-one (E)-1-[1-(3,4-Methylenedioxyphenyl)-1,3,4,9-tetrahydro-β-carbolin-2-yl]-3-(3,4-dihydroxyphenyl)propene-1-one (E)-N-Methyl-N-[4-[3-oxo-3-(1-(3,4-methylenedioxyphenyl)-1,3,4,9-tetrahydro-β-carbolin-2-yl)propenyl]phenyl]acetamide (E)-2,2-Dimethyl-N-[4-[3-Oxo-3-(1-(3,4-methylenedioxyphenyl)-1,3,4,9-tetrahydro-β-carbolin-2-yl)propenyl]phenyl]propionamide (E)-1-[1-(3,4-Methylenedioxyphenyl)-1,3,4,9-tetrahydro-β-carbolin-2-yl]-3-(3,5-dimethoxyphenyl)propene-1-one (E)-(N)-{4-[3-[1-(3,4-Methylenedioxyphenyl)-6-fluoro-1,3,4,9-tetrahydro-β-carbolin-2-yl]-3-oxopropenyl]-phenyl}-acetamide (E)-1-[1-(3,4-Methylenedioxyphenyl)-1,3,4,9-tetrahydro-β-carbolin-2-yl]-3-(3,4,5-trimethoxyphenyl)propene-1-one (E)-N-[4-[3-Oxo-3-(1-(3,4-methylenedioxyphenyl)-1,3,4,9-tetrahydro-β-carbolin-2-yl)propenyl]phenyl]isobutyramide (E)-1-[1-(3,4-Methylenedioxyphenyl)-6-fluoro-1,3,4,9-tetrahydro-β-carbolin-2-yl]-3-phenylpropene-1-one (E)-N-(2-Methoxyethyl)-4-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-(3-hydroxyphenyl)propene-1-one (E)-1-[1-(3,4-Methylenedioxyphenyl)-1,3,4,9-tetrahydro-β-carbolin-2-yl]-3-(3-methoxyphenyl)propene-1-one (E)-1-[1-(3,4-Methylenedioxyphenyl)-1,3,4,9-tetrahydro-β-carbolin-2-yl]-3-(3-nitrophenyl)propene-1-one (E)-1-[1-(3,4-Methylenedioxyphenyl)-1,3,4,9-tetrahydro-β-carbolin-2-yl]-3-[4-(2-dimethylaminoethoxy)phenyl]propene-1-one (E)-N-(2-Morpholin-4-ylethyl)-4-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-[4-(1H-tetrazol-5-yl)phenyl]propene-1-one (E)-1-[1-(3,4-Methylenedioxyphenyl)-1,3,4,9-tetrahydro-β-carbolin-2-yl]-3-(3-aminophenyl)propene-1-one (E)-N-Cyclohexyl-4-[3-oxo-3-(1-(3,4-methylenedioxyphenyl)-1,3,4,9-tetrahydro-β-carbolin-2-yl)propenyl]benzamide (E)-N-(Tetrahydrofuran-2-ylmethyl)-4-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-(3-cyanophenyl)propene-1-one (E)-N-(4-Piperidine-4-carboxylic acid, ethyl ester)-4-[3-oxo-3-(1-(3,4-methylenedioxyphenyl)-1,3,4,9-tetrahydro-β-carbolin-2-yl)propenyl]benzamide (E)-N-(4-Piperidine-4-carboxylic acid)-4-[3-oxo-3-(1-(3,4-methylenedioxyphenyl)-1,3,4,9-tetrahydro-β-carbolin-2-yl)propenyl]benzamide (E)-3-[3-Oxo-3-[1-(3,4-methylenedioxyphenyl)-1,3,4,9-tetrahydro-β-carbolin-2-yl]-propenyl]benzoic acid (E)-1-[1-(3,4-Methylenedioxyphenyl)-1,3,4,9-tetrahydro-β-carbolin-2-yl]-3-(3-(4-methylpiperazine-1-carbonyl)-phenyl)propene-1-one (E)-N-(2-Piperazin-1-ylethyl)-3-[3-oxo-3-(1-(3,4-methylenedioxyphenyl)-1,3,4,9-tetrahydro-β-carbolin-2-yl)propenyl]benzamide (E)-4-[3-Oxo-3-(1-(3,4-methylenedioxyphenyl)-1,3,4,9-tetrahydro-β-carbolin-2-yl)-propenyl]acetic acid ethyl ester (E)-1-[1-(3,4-Methylenedioxyphenyl)-1,3,4,9-tetrahydro-β-carbolin-2-yl]-3-(3-tetrazolophenyl)propene-1-one (E)-2-[3-Oxo-3-[1-(3,4-methylenedioxyphenyl)-1,3,4,9-tetrahydro-β-carbolin-2-yl]-propenyl]benzoicacid, methyl ester (E)-3-[3-Oxo-3-[1-(3,4-methylenedioxyphenyl)-1,3,4,9-tetrahydro-β-carbolin-2-yl]-propenyl]benzoic acid, methyl ester (E)-1-(4-[3-Oxo-3-(1-(3,4-methylenedioxyphenyl)-1,3,4,9-tetrahydro-β-carbolin-2-yl)-propenyl]phenyl)piperidine-4-carboxylic acid, ethyl ester (E)-N-(1-Ethylpyrrolidin-2-yl-methyl)-3-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-(3-(2-dimethylaminoethoxy)phenyl)propene-1-one (E)-1-[1-(3,4-Methylenedioxyphenyl)-1,3,4,9-tetrahydro-β-carbolin-2-yl]-3-(3,5-diterbutyl-4-hydroxyphenyl)propene-1-one (E)-3-[3-Oxo-3-[1-(4-methoxycarbonylphenyl)-1,3,4,9-tetrahydro-β-carbolin-2-yl]propenyl]benzoic acid, methyl ester (E)-2-[3-Oxo-3-[1-(3,4-methylenedioxyphenyl)-1,3,4,9-tetrahydro-β-carbolin-2-yl]propenyl]benzoic acid (E)-(4-[3-Oxo-3-(1-(3,4-methylenedioxyphenyl)-1,3,4,9-tetrahydro-β-carbolin-2-yl)propenyl]phenoxy)acetic acid, ethyl ester (E)-(4-[3-Oxo-3-(1-(3,4-methylenedioxyphenyl)-1,3,4,9-tetrahydro-β-carbolin-2-yl)-propenyl]phenyl)acetic acid (E)-(4-[3-Oxo-3-(1-(3,4-methylenedioxyphenyl)-1,3,4,9-tetrahydro-β-carbolin-2-yl)propenyl]phenoxy)acetic acid (E)-1-[1-(3,4-Methylenedioxyphenyl)-1,3,4,9-tetrahydro-β-carbolin-2-yl]-3-(3-nitro-4-chlorophenyl)propene-1-one (E)-1-[1-(3,4-Methylenedioxyphenyl)-1,3,4,9-tetrahydro-β-carbolin-2-yl]-3-(5-nitro-2-chlorophenyl)propene-1-one (E)-3-Chloro-4-[3-oxo-3-[1-(3,4-methylenedioxyphenyl)-1,3,4,9-tetrahydro-β-carbolin-2-yl]propenyl]benzoic acid, methyl ester (E)-(4-[3-Oxo-3-(1-(3,4-methylenedioxyphenyl)-1,3,4,9-tetrahydro-β-carbolin-2-yl)propenyl]benzyloxy)acetic acid (E)-1-[1-(3,4-Methylenedioxyphenyl)-1,3,4,9-tetrahydro-β-carbolin-2-yl]-3-(5-amino-2-chlorophenyl)propene-1-one (E)-3-Chloro-4-[3-oxo-3-[1-(3,4-methylenedioxyphenyl)-1,3,4,9-tetrahydro-β-carbolin-2-yl]propenyl]benzoic acid (E)-1-[1-(3,4-Methylenedioxyphenyl)-1,3,4,9-tetrahydro-β-carbolin-2-yl]-3-(3,5-dibromo-4-hydroxyphenyl)propene-1-one (E)-1-[1-(3,4-Methylenedioxyphenyl)-1,3,4,9-tetrahydro-β-carbolin-2-yl]-3-(4-(2-dimethylaminopropoxy)phenyl)propene-1-one (E)-2-Chloro-5-[3-oxo-3-[1-(3,4-methylenedioxyphenyl)-1,3,4,9-tetrahydro-β-carbolin-2-yl]propenyl]benzoic acid, methyl ester (E)-1-[1-(3,4-Methylenedioxyphenyl)-1,3,4,9-tetrahydro-β-carbolin-2-yl]-3-(4-(2-diisopropylaminoethoxy)phenyl)propene-1-one (E)-2-Chloro-5-[3-oxo-3-[1-(3,4-methylenedioxyphenyl)-1,3,4,9-tetrahydro-β-carbolin-2-yl]propenyl]benzoic acid (E)-1-[1-(3,4-Methylenedioxyphenyl)-1,3,4,9-tetrahydro-β-carbolin-2-yl]-3-(3-hydroxy-4-nitro-phenyl)propene-1-one (E)-1-[1-(3,4-Methylenedioxyphenyl)-1,3,4,9-tetrahydro-β-carbolin-2-yl]-3-(3,5-dimethyl-4-hydroxyphenyl)propene-1-one (E)-1-[1-(3,4-Methylenedioxyphenyl)-1,3,4,9-tetrahydro-β-carbolin-2-yl]-3-(3-(2-dimethylaminoethoxy)-4-nitrophenyl)propene-1-one (E)-1-[1-(3,4-Methylenedioxyphenyl)-1,3,4,9-tetrahydro-β-carbolin-2-yl]-3-(3-(2-dimethylaminoethoxy)-4-aminophenyl)propene-1-one (E)-1-[1-(3,4-Methylenedioxyphenyl)-1,3,4,9-tetrahydro-β-carbolin-2-yl]-3-(3-nitro-4-hydroxy-5-methoxyphenyl)propene-1-one (E)-1-[1-(3,4-Methylenedioxyphenyl)-1,3,4,9-tetrahydro-β-carbolin-2-yl]-3-(3-chlorophenyl)propene-1-one (E)-1-[1-(4-Methoxy-phenyl)-1,3,4,9-tetrahydro-β-carbolin-2-yl]-3-(2-chloro-5-nitrophenyl)propene-1-one (E)-1-[1-(3,4-Methylenedioxyphenyl)-1,3,4,9-tetrahydro-β-carbolin-2-yl]-3-(2,6-dichlorophenyl)propene-1-one (E)-1-[1-(3,4-Methylenedioxyphenyl)-1,3,4,9-tetrahydro-β-carbolin-2-yl]-3-(4-methylaminomethylphenyl)propene-1-one (E)-1-[1-(3,4-Methylenedioxyphenyl)-1,3,4,9-tetrahydro-β-carbolin-2-yl]-3-(3-methylphenyl)propene-1-one (E)-N-Methyl-(4-[3-oxo-3-(1-(3,4-methylenedioxyphenyl)-1,3,4,9-tetrahydro-β-carbolin-2-yl)propenyl]benzenesulfonamide (E)-1-[1-(3,4-Methylenedioxyphenyl)-1,3,4,9-tetrahydro-β-carbolin-2-yl]-3-(3-hydroxy-4-acetylphenyl)propene-1-one (E)-1-[1-(2,3-Dihydrobenzofuran-5-yl)-1,3,4,9-tetrahydro-β-carbolin-2-yl]-3-(2-chloro-5-nitrophenyl)propene-1-one (E)-1-[1-(3,4-Methylenedioxyphenyl)-1,3,4,9-tetrahydro-β-carbolin-2-yl]-3-(2-hydroxyphenyl)propene-1-one (E)-1-[1-(3,4-Methylenedioxyphenyl)-1,3,4,9-tetrahydro-β-carbolin-2-yl]-3-(3-nitro-2-piperidin-1-ylphenyl)propene-1-one (E)-1-[1-(2,3-Dihydrobenzofuran-5-yl)-1,3,4,9-tetrahydro-β-carbolin-2-yl]-3-phenylpropene-1-one (E)-1-[1-(4-Isopropylphenyl)-1,3,4,9-tetrahydro-β-carbolin-2-yl]-3-(3-nitrophenyl)propene-1-one (E)-1-[1-(2,3-Dihydrobenzofuran-5-yl)-1,3,4,9-tetrahydro-β-carbolin-2-yl]-3-(3-nitrophenyl)propene-1-one (E)-(R)-1-[1-(3,4-Methylenedioxyphenyl)-1,3,4,9-tetrahydro-β-carbolin-2-yl]-3-phenylpropene-1-one (E)-(S)-1-[1-(3,4-Methylenedioxyphenyl)-1,3,4,9-tetrahydro-β-carbolin-2-yl]-3-phenylpropene-1-one (E)-1-[1-(4-Methoxyphenyl)-1,3,4,9-tetrahydro-β-carbolin-2-yl]-3(3-nitrophenyl)propene-1-one (E)-1-[1-(4-Methylphenyl)-1,3,4,9-tetrahydro-β-carbolin-2-yl]-3-(2-chloro-5-nitrophenyl)propene-1-one (E)-N-(Tetrahydrofuran-2-ylmethyl)-3-[3-oxo-3-(1-(3,4-methylenedioxy)-1,3,4,9-tetrahydro-β-carbolin-2-yl)propenyl]benzamide (E)-1-[1-(Indan-5-yl)-1,3,4,9-tetrahydro-β-carbolin-2-yl]-3-phenylpropene-1-one (E)-1-[1-(3,4-Methylenedioxyphenyl)-1,3,4,9-tetrahydro-β-carbolin-2-yl]-3-(3-acetylphenyl)propene-1-one (E)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one (E)-4-[3-Oxo-3-[1-(4-methoxyphenyl)-1,3,4,9-tetrahydro-β-carbolin-2-yl]propenyl]benzoic acid, methyl ester (E)-1-[1-(3,4-Methylenedioxyphenyl)-1,3,4,9-tetrahydro-β-carbolin-2-yl]-3-(4-methyl-3,4-dihydro-2H-benzo[1,4]-oxazin-6-yl)propene-1-one (E)-1-[1-(3,4-Methylenedioxyphenyl)-1,3,4,9-tetrahydro-β-carbolin-2-yl]-3-(2-hydroxy-5-nitrophenyl)propene-1-one (E)-4-[3-Oxo-3-[1-(2,3-dihydrobenzofuran-5-yl)-1,3,4,9-tetrahydro-β-carbolin-2-yl]propenyl]benzoic acid, methyl ester (E)-4-[3-Oxo-3-[1-(4-methoxyphenyl)-1,3,4,9-tetrahydro-β-carbolin-2-yl]propenyl]benzoic acid (E)-4-[3-Oxo-3-[1-(2,3-dihydrobenzofuran-5-yl)-1,3,4,9-tetrahydro-β-carbolin-2-yl]propenyl]benzoic acid (E)-1-[1-(Benzofuran-5-yl)-1,3,4,9-tetrahydro-β-carbolin-2-yl]-3-phenylpropene-1-one (E)-3-[3-Oxo-3-(1-(3,4-methylenedioxyphenyl)-1,3,4,9-tetrahydro-β-carbolin-2-yl)-propenyl]phenyl) trifluoromethanesulfonic acid, phenyl ester (E)-1-[1-(3,4-Methylenedioxyphenyl)-1,3,4,9-tetrahydro-β-carbolin-2-yl]-3-[4-(2-hydroxyethoxy)phenyl]propene-1-one (E)-1-[1-(Benzofuran-5-yl-1,3,4,9-tetrahydro-β-carbolin-2-yl)]-3-(4-(2-dimethylaminoethoxy)phenyl)propene-1-one (E)-1-[1(3,4-Methylenedioxyphenyl)-1,3,4,9-tetrahydro-β-carbolin-2-yl]-3-(2-dimethylaminophenyl)propene-1-one (E)-1-[1-(3,4-Methylenedioxyphenyl)-1,3,4,9-tetrahydro-β-carbolin-2-yl]-3-(2-piperidin-1-ylphenyl)propene-1-one (E)-4-[3-Oxo-3-[1-(benzofuran-5-yl-1,3,4,9-tetrahydro-β-carbolin-2-yl]-propenyl]-benzoic acid, methyl ester (E)-4-[3-(1-Benzofuran-5-yl-1,3,4,9-tetrahydro-β-carbolin-2-yl)-3-oxo-propenyl]-benzoic acid (E)-4-[3-Oxo-3-(1-(3,4-methylenedioxyphenyl)-1,3,4,9-tetrahydro-β-carbolin-2-yl)propenyl]phenyl) trifluoromethanesulfonic acid, phenyl ester (E)-1-[1-(3,4-Methylenedioxyphenyl)-1,3,4,9-tetrahydro-β-carbolin-2-yl]-3-(2-(2-dimethylaminoethoxy)phenyl) propene-1-one (E)-1-[1-(3-Fluoro-4-methoxyphenyl)-1,3,4,9-tetrahydro-β-carbolin-2-yl]-3-phenylpropene-1-one (E)-(R)-1-[1-(2,3-Dihydrobenzofuran-5-yl)-1,3,4,9-tetrahydro-β-carbolin-2-yl)]-3-(4-(2-dimethylaminoethoxy) phenyl)propene-1-one (E)-[1-(2,3-Dihydrobenzo[1,4]dioxin-6-yl)-1,3,4,9-tetrahydro-β-carbolin-2-yl]-3-phenylpropene-1-one (E)-1-[1-(2,3-Dihydrobenzofuran-5-yl)-1,3,4,9-tetrahydro-β-carbolin-2-yl)]-3-(4-(2-pyrrolidin-1-ylethoxy) phenyl)propene-1-one (E)-1-[1-(3,4-Methylenedioxyphenyl)-1,3,4,9-tetrahydro-β-carbolin-2-yl]-3-[4-pyrrolidin-1-ylphenyl]propene-1-one (E)-(R)-1-[1-(2,3-Dihydrobenzofuran-5-yl)-1,3,4,9-tetrahydro-β-carbolin-2-yl)]-3-(3-nitrophenyl)propene-1-one (E)-1-[1-(3,4-Methylenedioxyphenyl)-1,3,4,9-tetrahydro-β-carbolin-2-yl]-3-[4-imidazol-1-ylphenyl]propene-1-one (E)-4-[3-[1-(2,3-Dihydrobenzo[1,4]dioxin-6-yl)-1,3,4,9-tetrahydro-β-carbolin-2-yl]-3-oxo-propenyl]benzoic acid, methyl ester (E)-1-[1-(2,3-Dihydrobenzo[1,4]dioxin-6-yl)-1,3,4,9-tetrahydro-β-carbolin-2-yl]-3-(3-nitrophenyl)propene-1-one (E)-1-[1-(2,3-Dihydrobenzo[1,4]dioxin-6-yl)-1,3,4,9-tetrahydro-β-carbolin-2-yl)]-3-(4-(2-dimethylaminoethoxy) phenyl)propene-1-one (E)-1-[1-(3-Fluoro-4-methoxyphenyl)-1,3,4,9-tetrahydro-β-carbolin-2-yl]-3-(4-(2-dimethylaminoethoxy) phenyl)propene-1-one (E)-4-[3-[1-(2,3-Dihydrobenzo[1,4]dioxin-6-yl)-1,3,4,9-tetrahydro-β-carbolin-2-yl]-3-oxopropenyl]benzoic acid (E)-(R)-1-[1-(2,3-Dihydrobenzofuran-5-yl)-1,3,4,9-tetrahydro-β-carbolin-2-yl]-3-phenylpropene-1-one (E)-(S)-1-[1-(2,3-Dihydrobenzofuran-5-yl)-1,3,4,9-tetrahydro-β-carbolin-2-yl)]-3-(4-(2-dimethylaminoethoxy) phenyl)propene-1-one (E)-1-[1-(2,3-Dihydrobenzofuran-5-yl)-1,3,4,9-tetrahydro-β-carbolin-2-yl]-3-(4-aminophenyl)propene-1-one (E)-(S)-1-[1-(2,3-Dihydrobenzofuran-5-yl)-1,3,4,9-tetrahydro-β-carbolin-2-yl]-3-phenylpropene-1-one (E)-(S)-1-[1-(2,3-Dihydrobenzofuran-5-yl)-1,3,4,9-tetrahydro-β-carbolin-2-yl]-3-(3-nitrophenyl)propene-1-one (E)-(R)-1-[1-(2,3-Dihydrobenzofuran-5-yl)-1,3,4,9-tetrahydro-β-carbolin-2-yl)]-3-(4-(1-(S)-methylpyrrolidin-2-yl-methoxy)phenyl)propene-1-one (E)-(R)-1-[1-(2,3-Dihydrobenzofuran-5-yl)-1,3,4,9-tetrahydro-β-carbolin-2-yl)]-3-(3-hydroxyphenyl)propene-1-one (E)-(R)-1-[1-(2,3-Dihydrobenzofuran-5-yl)-1,3,4,9-tetrahydro-β-carbolin-2-yl)]-3-(4-(2-dimethylamino-1-methylethoxy)phenyl)propene-1-one (E)-1-(1-Phenyl-1,3,4,9-tetrahydro-β-carbolin-2-yl)-3-(4-(4-methylpyperazin-1-yl)-phenyl)propene-1-one (E)-(R)-1-[1-(3,4-Methylenedioxyphenyl)-1,3,4,9-tetrahydro-β-carbolin-2-yl)]-3-(4-(1-(S)-methylpyrrolidin-2-yl-methoxy)phenyl)propene-1-one (E)-(R)-1-[1-(3,4-Methylenedioxyphenyl)-1,3,4,9-tetrahydro-β-carbolin-2-yl)]-3-(4-(2-dimethylamino-1-methylethoxy)phenyl)propene-1-one (E)-(R)-1-[1-(3,4-Methylenedioxyphenyl)-1,3,4,9-tetrahydro-β-carbolin-2-yl)]-3-(4-(2-dimethylaminopropoxy)phenyl)propene-1-one (E)-4-[3-Oxo-3-[1-(3,4-fluorophenyl)-1,3,4,9-tetrahydro-β-carbolin-2-yl]propenyl]benzoic acid, methyl ester (E)-(R)-[1-(2,3-Dihydrobenzofuran-5-yl)-1,3,4,9-tetrahydro-β-carbolin-2-yl)]-3-(4-(2-diethylaminoethoxy) phenyl)propene-1-one (E)-(R)1-[1-(2,3-Dihydrobenzofuran-5-yl)-1,3,4,9-tetrahydro-β-carbolin-2-yl)]-3-(4-(2-dimethylaminopropoxy)phenyl)propene-1-one (E)-4-[3-Oxo-3-[1-(3,4-difluorophenyl)-1,3,4,9-tetrahydro-β-carbolin-2-yl]propenyl]benzoic acid (E)-(R)-1-[1-(2,3-Dihydrobenzofuran-5-yl)-1,3,4,9-tetrahydro-β-carbolin-2-yl)]-3-(4-aminophenyl)propene-1-one (E)-(R)-1-[1-(3,4-Methylenedioxyphenyl)-1,3,4,9-tetrahydro-β-carbolin-2-yl)]-3-(4-aminophenyl)propene-1-one (E)-(R)-1-[1-(3,4-Methylenedioxyphenyl)-1,3,4,9-tetrahydro-β-carbolin-2-yl)]-3-(4-(2-pyrrolidin-1-ylethoxy) phenyl)propene-1-one (E)-(R)-1-[1-(3,4-Methylenedioxyphenyl)-1,3,4,9-tetrahydro-β-carbolin-2-yl)]-3-(4-(2-diethylaminoethoxy) phenylpropene-1-one (E)-1-[1-(3-Fluoro-4-methoxyphenyl)-1,3,4,9-tetrahydro-β-carbolin-2-yl)]-3-(3-nitrophenyl)propene-1-one (E)-(R)-1-[1-(2,3-Dihydrobenzofuran-5-yl)-1,3,4,9-tetrahydro-β-carbolin-2-yl]-3-(4-trifluoromethylphenyl) propene-1-one (E)-(R)-1-[1-(2,3-Dihydrobenzofuran-5-yl)-1,3,4,9-tetrahydro-β-carbolin-2-yl]-3-(3-trifluoromethylphenyl) propene-1-one (E)-(R)-1-[1-(2,3-Dihydrobenzofuran-5-yl)-1,3,4,9-tetrahydro-β-carbolin-2-yl]-3-(4-(2-morpholin-4-ylethoxy) phenyl)propene-1-one (E)-(R)-1-[1-(2,3-Dihydrobenzofuran-5-yl)-1,3,4,9-tetrahydro-β-carbolin-2-yl]-3-(4-(2-(ethylmethylamino) ethoxy)phenyl)propene-1-one (E)-1-[1-(2,3-Dihydrobenzofuran-5-yl)-1,3,4,9-tetrahydro-β-carbolin-2-yl]-3-(4-(3-(dimethylamino) propenyl)phenyl)propene-1-one (E)-(R)-1-[1-(2,3-Dihydrobenzofuran-5-yl)-1,3,4,9-tetrahydro-β-carbolin-2-yl]-3-(4-(3-dimethylamino-2-hydroxypropoxy)phenyl)propene-1-one (E)-(R)-1-(1-(2,3-Dihydrobenzofuran-5-yl)-1,3,4,9-tetrahydro-β-carbolin-2-yl)-3-(4-formylphenyl)propene-1-one (E)-(R)-1-[1-(2,3-Dihydrobenzofuran-5-yl)-1,3,4,9-tetrahydro-β-carbolin-2-yl]-3-(4-propylaminomethyl) phenyl)propene-1-one (E)-(R)-1-[1-(2,3-Dihydrobenzofuran-5-yl)-1,3,4,9-tetrahydro-β-carbolin-2-yl]-3-[4-(2-dimethylaminoethylamino)phenylpropene-1-one (E)-(R)-1-[1-(2,3-Dihydrobenzofuran-5-yl)-1,3,4,9-tetrahydro-β-carbolin-2-yl]-3-(4-(2-aminoethoxy)phenyl) propene-1-one (E)-(R)-1-[1-(2,3-Dihydrobenzofuran-5-yl)-1,3,4,9-tetrahydro-β-carbolin-2-yl]-3-(4-hydroxyphenyl)propene-1-one (E)-(R)-1-[1-(2,3-Dihydrobenzofuran-5-yl)-1,3,4,9-tetrahydro-β-carbolin-2-yl]-3-(4-(4-methylpiperazin-1-yl) phenylpropene-1-one (E)-(R)-1-[1-(2,3-Dihydrobenzofuran-5-yl)-1,3,4,9-tetrahydro-β-carbolin-2-yl]-3-(4-methylaminomethyl) phenyl)propene-1-one (E)-(R)-1-[1-(2,3-Dihydrobenzofuran-5-yl)-1,3,4,9-tetrahydro-β-carbolin-2-yl]-3-(4-isopropylaminomethyl) phenyl)propene-1-one (E)-(R)-1-[1-(2,3-Dihydrobenzofuran-5-yl)-1,3,4,9-tetrahydro-β-carbolin-2-yl]-3-(4-dimethylaminomethyl) phenyl)propene-1-one (E)-(R)-1-[1-(2,3-Dihydrobenzofuran-5-yl)-1,3,4,9-tetrahydro-β-carbolin-2-yl]-3-[4-(3-dimethylaminopropoxy)phenyl]propene-1-one (E)-(R)-1-[1-(2,3-Dihydrobenzofuran-5-yl)-1,3,4,9-tetrahydro-β-carbolin-2-yl]-3-(4-(2-piperidin-1-ylethoxy) phenyl)propene-1-one (E)-1-[1-(3,4-Methylenedioxyphenyl)-1,3,4,9-tetrahydro-β-carbolin-2-yl)-3-(4-(2-piperidin-1-yl-ethoxy)phenyl] propene-1-one (E)-(R)-[2-(4-{3-[1-(2,3-Dihydrobenzofuran-5-yl)-1,3,4,9-tetrahydro-β-carbolin-2-yl]-3-oxopropenyl}-phenoxy) ethyl]methylcarbamic acid, tertbutyl ester (E)-(R)-1-[1-(2,3-Dihydrobenzofuran-5-yl)-1,3,4,9-tetrahydro-carbolin-2-yl]-3-[4-(2-methylaminoethoxy) phenyl]propene-1-one and pharmaceutically acceptable salts and solvates (e.g., hydrates) thereof.

A specific compound of the invention is:

(E)-(R)-1-[1-(2,3-Dihydrobenzofuran-5-yl)-1,3,4,9-tetrahydro-β-carbolin-2-yl)]-3-(4-(2-dimethylaminoethoxy) phenyl)propene-1-one, and pharmaceutically acceptable salts and solvates (e.g., hydrates) thereof.

DETAILED DESCRIPTION OF THE PREFERRED EMBODIMENTS

It has been shown that compounds of the present invention are potent and selective inhibitors of cGMP-specific PDEs 1, 5, and 6, and particularly PDE5. Thus, compounds of formula (I) are of interest for use in therapy, specifically for the treatment of a variety of conditions where selective inhibition of cGMP-specific PDE is thought to be beneficial.

In summary, the biochemical, physiological, and clinical effects of PDE5 inhibitors suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, peptic ulcer, osteoporosis, preterm labor, benign prostatic hypertrophy, male and female erectile dysfunction, and diseases characterized by disorders of gut motility (e.g., irritable bowel syndrome or IBS).

An especially important use is the treatment of male erectile dysfunction, which is one form of impotence and is a common medical problem. Impotence can be defined as a lack of power, in the male, to copulate and can involve an inability to achieve penile erection or ejaculation, or both. The incidence of erectile dysfunction increases with age, with about 50% of men over the age of 40 suffering from some degree of erectile dysfunction.

Many compounds have been investigated for their therapeutic potential in the treatment of MED, including phenoxybenzamine, papaverine, prostaglandin E1 (PGE1), and phentolamine. These compounds, either alone or in combination, are typically self-administered by intracavernosal (i.c.) injection. While such treatments are effective, a treatment that is less invasive than injection therapy is preferred because pain, priapism, and fibrosis of the penis are associated with the i.c. administration of these agents.

For example, alprostadil (i.e., prostaglandin E1) delivered by intraurethral deposition has been approved for the treatment of MED. However, clinical studies showed that this route of administration is not effective in all patients. In addition, phentolamine and apomorphine are being evaluated as oral and sublingual therapies for MED, but neither compound has demonstrated efficacy across a broad range of subjects. Potassium channel openers (KCO) and vasoactive intestinal polypeptide (VIP) also have been shown to be active i.c., but cost and stability issues could limit development of the latter. An alternative to the i.c. route is the use of glyceryl trinitrate (GTN) patches applied to the penis, which has been shown to be effective but produces side effects in both patient and partner.

As an alternative to pharmacological treatment, a variety of penile prostheses have been used to assist achievement of an erection. The short-term success rate is good, but problems with infection and ischemia, especially in diabetic men, make this type of treatment a final option rather than a first-line therapy.

Because of the disadvantages of prior treatments for MED, new strategies to improve erectile response that exploit different physiological mechanisms are being investigated. One area of investigation is increasing the intracellular concentration of cGMP by providing a new type of oral therapy for the treatment of MED.

Increasing cGMP concentration is an important step in the physiology of penile erections. A penile erection is caused by neural stimuli that ultimately cause vasodilation of the arteries and sinusoidal spaces of the corpus cavernosum. Research indicates that nitric oxide plays a central role in this vasodilation.

In particular, atrial natriuretic peptides (ANP) and nitric oxide (NO, sometimes referred to as endothelium-derived relaxing factor or EDRF) relax smooth muscle by increasing guanylyl cyclase activity, which raises intracellular cGMP concentration. Intracellular cGMP is hydrolyzed by phosphodiesterases (PDEs), thereby terminating the action of the cyclic nucleotide. PDE5 is the major cGMP hydrolyzing enzyme in vascular smooth muscle. Accordingly, PDE5 inhibition potentiates the relaxant effects of ANP and nitric oxide by increasing the cGMP levels. Therefore, a compound that inhibits the PDE5 enzyme (and thereby indirectly inhibits the hydrolysis of cGMP) should potentiate the vascular response to nitric oxide, thereby facilitating the achievement and maintenance of erection.

PDE5 inhibitors have potential for use in treating male erectile dysfunction (MED), hypertension, heart failure, and other disease states because of their ability to facilitate the action of ANP and NO. For example, sildenafil, a PDE inhibitor showing little selectivity with respect to PDE6, has the structure:

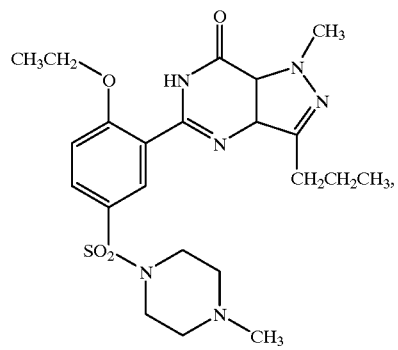

and has shown efficacy in oral administration clinical trials for MED, which supports the hypothesis that augmenting normal or subnormal guanylyl cyclase stimuli has therapeutic benefits.

It is envisioned, therefore, that compounds of formula (I) are useful in the treatment of erectile dysfunction. Furthermore, the compounds can be administered orally, thereby obviating the disadvantages associated with intracavernosal administration. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal, including man.

It also has been observed that human corpus cavernosum contains three distinct PDE enzymes (see A. Taher et al., *J. Urol.*, 149, p. 285A (1993)), one of which is the cGMP-specific PDE5. As a consequence of the selective PDE5 inhibition exhibited by compounds of the present invention, the present compounds sustain cGMP levels, which in turn mediate relaxation of the corpus cavernosum tissue and consequent penile erection.

Although the compounds of the invention are envisioned primarily for the treatment of erectile dysfunction in humans, such as male erectile dysfunction and female sexual dysfunction, including orgasmic dysfunction related to clitoral disturbances, they also can be used for the treatment of premature labor and dysmenorrhea.

It is understood that references herein to treatment extend to prophylaxis, as well as treatment of established conditions.

It also is understood that "a compound of formula (I)," or a physiologically acceptable salt or solvate thereof, can be administered as the neat compound, or as a pharmaceutical composition containing either entity.

A further aspect of the present invention is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™. Oral administration generally is preferred.

With respect to treating sexual dysfunction and particularly erectile dysfunction in humans, oral administration of the compounds of the invention is the preferred route. Oral administration is the most convenient and avoids the disadvantages associated with intracavernosal administration. For patients suffering from a swallowing disorder or from impairment of drug absorption after oral administration, the drug can be administered parenterally, e.g., sublingually or buccally.

For administration to man in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. For example, the compound can be administered orally, buccally, or sublingually in the form of tablets containing excipients such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents (e.g., methylcellulose, a semisynthetic glyceride such as witepsol, or mixtures of glycerides such as a mixture of apricot kernel oil and PEG-6 esters, or mixtures of PEG-8 and caprylic/capric glycerides). A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor.

There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, including man, comprising a compound of formula (I) or a pharmaceutically acceptable salt thereof, together with a pharmaceutically acceptable diluent or carrier.

A compound of formula (I) also can be used in combination with other therapeutic agents which can be useful in the treatment of the above-mentioned and other disease states. The invention thus provides, in another aspect, a combination of a compound of formula (I), together with a second therapeutically active agent.

A compound of formula (I) can be used in the preparation of a medicament for co-administration with the second therapeutically active agent in treatment of conditions where inhibition of a cGMP-specific PDE is beneficial. In addition, a compound of formula (I) can be used in the preparation of a medicament for use as adjunctive therapy with a second therapeutically active compound to treat such conditions. Appropriate doses of known second therapeutic agents for use in combination with a compound of formula (I) are readily appreciated by those skilled in the art.

In particular, because compounds of the present invention maintain cGMP levels, the compounds of formula (I) can provide beneficial antiplatelet, antineutrophil, antivasospastic, vasodilatory, natriuretic, and diuretic activities, as well as potentiate the effects of endothelium-derived relaxing factor (EDRF), gastric NO administration, nitrovasodilators, atrial natriuretic factor (ANF), brain natriuretic peptide (BNP), C-type natriuretic peptide (CNP), and endothelium-dependent relaxing agents such as bradykinin, acetylcholine, and 5-HT$_1$.

The present selective PDE5 inhibitors in combination with vasodilators, including nitric oxide and nitric oxide donators and precursors, such as the organic nitrate vasodilators which act by releasing nitric oxide in vivo, are especially useful in treatment of angina, congestive heart failure, and malignant hypertension (e.g., pheochromocytoma). Related to the capacity of the present PDE5 inhibitors to potentiate nitric oxide donors and precursors is their ability, in spontaneously hypertensive rats, to reverse the desensitization to these agents that occurs with chronic use.

Examples of vasodilators that can be used in conjunction with the compounds of formula (I) include, but are not limited to, (a) organic nitrates, such as nitroglycerin, isosorbide dinitrate, pentaerythrityl tetranitrate, isosorbide-5-mononitrate, propatyl nitrate, trolnitrate, nicroandil, mannitol hexanitrate, inositol hexanitrate, N-[3-nitratopivaloyl]-L-cysteine ethyl ester, (b) organic nitrites, like isoamyl nitrite, (c) thionitrites, (d) thionitrates, (e) S-nitrosothiols, like S-nitroso-N-acetyl-D,L-penicillamine, (f) nitrosoproteins, (g) substituted furoxanes, such as 1,2,5-oxadiazole-2-oxide and furazan-N-oxide, (h) substituted sydnonimines, such as molsidomine and mesocarb, (i) nitrosyl complex compounds, like iron nitrosyl compounds, especially sodium nitroprusside, and (j) nitric oxide (NO) itself.

Other classes of therapeutic agents that can be used in conjunction with the compounds of formula (I), in addition to vasodilators, include, but are not limited to, α-adrenergic blockers, mixed α,β-blockers, prostaglandin EI (PGEI) and prostacyclin (PGI2), angiotensin converting enzyme inhibitors (ACE inhibitors), neutral endopeptidase (NEP) inhibitors, centrally acting dopaminergic agents (such as apomorphine), vasoactive intestinal peptides (VIP), calcium channel blockers, and compounds like thiazides.

Alpha-adrenergic blockers inhibit vasoconstriction in the corpus cavernosum. Because PDE5 inhibitors enhance vasodilation of the same smooth muscle tissue, a PDE5 inhibitor of formula (I) and an 60-adrenergic blocker, like phentolamine or prazocin, or a centrally acting dopaminergic agent, like apomorphine, can be expected to potentiate one another in a treatment for MED or other disorders. Potentiation of mixed α,β-blockers, like carvedilol, which is employed in treatment of hypertension, also is expected. Similarly, α$_2$-adrenergic blockers, like yohimbine, can be potentiated.

Prostaglandin E1 enhances relaxation of the corpus cavernosum by increasing the formation of cyclic AMP. Cyclic AMP can be degraded in the corpus cavernosum by PDE3, which is inhibited by cyclic GMP. By maintaining cyclic GMP levels, a PDE5 inhibitor can indirectly inhibit PDE3 activity, and hence block degradation of cyclic AMP. Therefore, a PDE5 inhibitor of formula (I) can be expected to potentiate the activity of PGE1 in the treatment of MED or compounds having similar activities, such as PGI2, in the treatment of pulmonary hypertension, for example.

Angiotensin converting enzyme (ACE) inhibitors block the conversion of angiotensin I into angiotensin II, which causes systemic vasoconstriction and the retention of sodium and water. PDE5 inhibitors cause vasodilation in hypertensive animals, and stimulate the excretion of sodium and water in normotensive animals. Therefore, a PDE5 inhibitor of formula (I) can be combined with an ACE inhibitor to achieve more powerful vasodilatory and natriuretic effects in, for example, treatment of congestive heart failure or hypertensive states.

Neutral endopeptidase (NEP) inhibitors inhibit the degradation of atrial natriuretic peptide (ANP) by NEP. PDE5 inhibitors can be expected to potentiate the action of ANP by inhibiting degradation of its second messenger, cyclic GMP, and, therefore, a compound of formula (I) can potentiate the effects of agents, like NEP inhibitors, that increase blood levels of ANP.

The combination referred to above can be presented for use in the form of a single pharmaceutical formulation, and, thus, pharmaceutical compositions comprising a combination as defined above together with a pharmaceutically acceptable diluent or carrier comprise a further aspect of the invention.

The individual components of such a combination, therefore, can be administered either sequentially or simultaneously from the same or separate pharmaceutical formulations. As is the case for the PDE5 inhibitors of formula (I), a second therapeutic agent can be administered by any suitable route, for example, by oral, buccal, inhalation, sublingual, rectal, vaginal, transurethral, nasal, topical, percutaneous (i.e., transdermal), or parenteral (including intravenous, intramuscular, subcutaneous, and intracoronary) administration.

In some embodiments, the compound of formula (I) and the second therapeutic agent are administered by the same route, either from the same or from different pharmaceutical compositions. However, in other embodiments, using the same route of administration for the compound of formula (I) and the second therapeutic agent either is impossible or is not preferred. For example, if the second therapeutic agent is nitric oxide, which typically is administered by inhalation, the compound of formula (I) must be administered by a different route. Furthermore, if a compound of formula (I) is used in combination with a nitrate vasodilator, for example, in treatment of an erectile dysfunction, it is preferred that the compound of formula (I) is administered orally and the vasodilator is administered topically, and preferably in a manner which avoids substantial systemic delivery of the nitrate.

The combination of a compound of formula (I) and a second therapeutic agent is envisioned in the treatment of several disease states. Examples of such treatments are the systemic and topical treatment of male and female sexual dysfunction, wherein a compound of formula (I) is used in combination with phentolamine, prazocin, apomorphine, PDE1, or a vasoactive intestinal peptide. The compound of formula (I) can be administered orally or transuretherally, and the second therapeutic agent can be administered orally, topically, or intracavernosally, for example. Persons skilled in the art are aware of the best modes of administration for each therapeutic agent, either alone or in a combination.

Other disease states that can be treated by a combination of a compound of formula (I) and a second therapeutic agent include, but are not limited to:

(a) treatment of hypertension using a compound of formula (I) in combination with an α-adrenergic blocker, a mixed α,β-blocker, like carvedilol, a thiazide, sodium nitroprusside, an ACE inhibitor, or a calcium channel blocker;

(b) treatment of pulmonary hypertension using a compound of formula (I) in combination with inhaled NO on other inhaled vasodilators, or with PGI2 administered via an IV pump; and (c) treatment of chronic obstructive pulmonary disease using a compound of formula (I) in combination with inhaled NO.

Compounds of formula (I) can be prepared by any suitable method known in the art or by the following processes which form part of the present invention. In the methods below $R^0$, $R^1$, $R^2$, $R^3$, and $R^4$ are as defined in formula (I) above unless otherwise indicated.

There is further provided by the present invention a process (A) of preparing a compound of formula (I), said process comprises reacting compounds of formula (II) and (III)

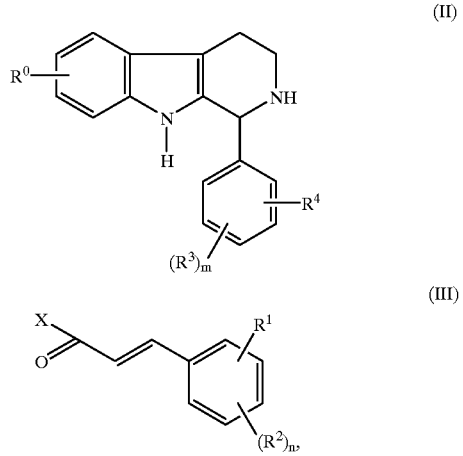

where X represents a hydroxyl or halogen group.

The reaction is carried out in the presence of 1,3-dicyclohexylcarbodiimide (DCC) or 1-(3-dimethylaminopropyl)-3-ethylcarbodiimide (EDCl) and 1-hydroxybenzotriazole (HOBT) in a suitable organic solvent, such as dimethylformamide (DMF) or dichloromethane (DCM), for several hours, e.g., 8 hours to 2 days.

Compounds of formula (I) can be prepared as individual enantiomers from the appropriate enantiomer of formula (II) or as a racemic mixture from the appropriate racemic compound of formula (II). Individual enantiomers of the compounds of the invention can be prepared from racemates by resolution using methods known in the art for the separation of racemic mixtures into their constituent enantiomers, for example using HPLC on a chiral column such as Hypersil naphtyl urea or using separation of salts of diastereoisomers.

A compound of formula (II) can be prepared by Pictet-Spengler cyclization between a tryptamine derivative of formula (IV) and an aldehyde of formula (V).

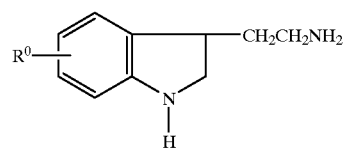

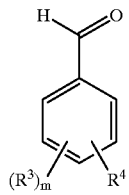

The reaction can be conveniently effected in a suitable solvent such as a halogenated hydrocarbon (e.g., dichloromethane) or an aromatic hydrocarbon (e.g., toluene) in the presence of an acid such as trifluoroacetic acid (TFA). The reaction can conveniently be carried out at a temperature of from 20° C. to reflux to provide a compound of formula (II) in one step. The reaction can also be carried out in a solvent such as an aromatic hydrocarbon (e.g., toluene) under reflux optionally using a Dean-stark apparatus to trap the produced water.

The reaction provides racemic compounds of formula (II). Enantiomers can be obtained from a resolution with N-acetyl leucine using fractional crystallization in EtOAc::MeOH (ethyl/acetate:methanol) as solvent. (R) and (S) enantiomers can be isolated as salts depending upon whether N-acetyl-(D) and (L)-leucine was used as the starting material.

Compounds of formulae (IV) and (V) are commercially available compounds or prepared by standard synthetic techniques as hereinafter described in the Examples.

A compound of formula (III) can be prepared from a corresponding aldehyde of formula (VI)

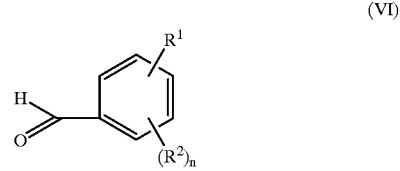

(VI)

by employing a Wittig reaction followed by basic hydrolysis, or by a Wittig-Horner reaction.

Alternatively a compound of formula (III) can be prepared from a compound of formula (VI) by a Knoevenagel reaction employing malonic acid.

Compounds of formula (VI) can be prepared from known corresponding alcohol, nitrile, or halide derivatives, using techniques well known in the art of synthetic organic chemistry.

According to a further general process (B), compounds of formula (I) can be converted to alternative compounds of formula (I), employing suitable interconversion techniques such as hereinafter described in the Examples.

Compounds of this invention can be isolated in association with solvent molecules by crystallization from or evaporation of an appropriate solvent.

The pharmaceutically acceptable acid addition salts of the compounds of formula (I) which contain a basic center may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of a compound of formula (I) with a suitable base. Both types of salt may be formed or inter-converted using ion-exchange resin techniques.

Thus, according to a further aspect of the invention, provide a process for preparing a compound of formula (I) or a salt or solvate (e.g., hydrate) thereof is provided. The process comprises process (A) or (B), as hereinbefore described, followed by
i) salt formation; or
ii) solvate (e.g., hydrate) formation.

The following additional abbreviations are hereinafter used in the accompanying examples: min (minute), g (gram), mmol (millimole), m.p. (melting point), eq (equivalents), mL (milliliter), μL (microliters), DCM or $CH_2Cl_2$ (dichloromethane), TFA (trifluoracetic acid), rt (room temperature), DMSO (dimethylsulfoxide), NBS (N-bromosuccinimide), THF (tetrahydrofuran), PTSA (p-toluenesulfonic acid), ABN (2,2'-azobis isobutyronitrile), MeOH (methanol), $MgSO_4$ (magnesium sulfate), $NaHCO_3$ (sodium bicarbonate), $NaSO_4$ (sodium sulfate), $Na_2CO_3$ (sodium carbonate), $iPr_2O$ (diisopropyl ether), $CDCl_3$ (deuterated chloroform), $MnO_2$ (manganese oxide), $K_2CO_3$ (potassium carbonate), $Et_3N$ (triethylamine), EtOAc (ethyl acetate), $CCl_4$ (carbon tetrachloride), NaOH (sodium hydroxide), EtOH (ethanol), $CH_3CN$ (acetonitrile), $CHCl_3$ (chloroform), and TBDMSCl (tert-butyldimethylsilyl chloride).

Intermediate 1

1-Phenyl-2,3,4,9-tetrahydro-1H-β-carboline

A solution of tryptamine (15 g, 94.0 mmol) and benzaldehyde (10.9 g, 1.1 equiv.) in DCM (800 mL) was treated with TFA (15 mL, 2 equiv.). The resulting mixture was stirred at rt for one day and then neutralized to pH 7 with a saturated aqueous solution of sodium carbonate. After filtration and concentration to dryness the residue was recrystallized from 2-propanol to give the title compound (11.0 g, 47%) as white crystals. MP: 175–177° C.

Intermediate 2

1-(4-Methoxyphenyl)-2,3,4.9-tetrahydro-1H-β-carboline

This product was prepared using the same procedure as for Intermediate 1 with tryptamine (15 g, 94.9 mmol), 4-methoxybenzaldehyde (12.9 g, 1.1 equiv.) and TFA (14.6 mL, 2 equiv.) to give the title compound (20.9 g, 80%) as a brownish powder. MP: 131° C.

Intermediate 3

1-(4-Nitrophenyl)-2,3,4,9-tetrahydro-1H-β-carboline

This product was prepared using the same procedure as for Intermediate 1 with tryptamine (2.0 g, 12.5 mmol), 4-nitrobenzaldehyde (1.88 g, 1 equiv.) and TFA (1.9 mL, 2 equiv.) to give the title compound (3.1 g, 86%) as a yellow powder. MP: 190° C.

Intermediate 4

1-(4-Trifluoromethoxyphenyl)-2,3,4,9-tetrahydro-1H-β-carboline

This product was prepared using the same procedure as for Intermediate 1 with tryptamine (2.0 g, 12.5 mmol), 4-trifluoromethoxybenzaldehyde (2.4 g, 1 equiv.) and TFA (1.9 mL, 2 equiv.) to give the title compound (1.6 g, 38%) as a white powder. MP: 68–69° C.

Intermediate 5

1-(4-Chlorophenyl)-2,3,4,9-tetrahydro-1H-β-carboline

This product was prepared using the same procedure as for Intermediate 1 with tryptamine (5.0 g, 30 mmol), 4-chlorobenzaldehyde (4.6 g, 1 equiv.) and TFA (4.6 mL, 2 equiv.) to give the title compound (4.16 g, 49%) as a white powder. MP: 161° C.

Intermediate 6

1-(4-Methylphenyl)-2,3,4,9-tetrahydro-1H-β-carboline

This product was prepared using the same procedure as for Intermediate 1 with tryptamine (1.0 g, 6.2 mmol), 4-methylbenzaldehyde (0.74 g, 1 equiv.) and TFA (1 mL, 2 equiv.) to give the title compound (1.6 g, 100%) as a white powder. MP: 207–209° C.

Intermediate 7

1-(3,4-Methylenedioxyphenyl)-2,3,4,9-tetrahydro-1H-β-carboline

This product was prepared using the same procedure as for Intermediate 1 with tryptamine (20.0 g, 120 mmol), 3,4-methylenedioxybenzaldehyde (20.6 g, 1.1 equiv.) and TFA (18 mL, 2 equiv.) to give the title compound (22 g, 60%) as white crystals after recrystallization from ethanol. MP: 178° C.

Intermediate 8

4-(2,3,4,9-Tetrahydro-1H-β-carbolin-1-yl)benzoic Acid, Methyl Ester

This product was prepared using the same procedure as for Intermediate 1 with tryptamine (2.8 g, 17.4 mmol), 4-formylbenzoic acid, methyl ester (2.87 g, 1.1 equiv.) and TFA (2.7 mL, 2 equiv.) to give the title compound (0.5 g, 9%) as white crystals after recrystallization from isopropanol:$H_2O$. MP: 179° C.

Intermediate 9

1-Indan-5-yl-2,3,4,9-tetrahydro-1H-β-carboline

This product was prepared using the same procedure as for Intermediate 1 with tryptamine (1.28 g, 8.0 mmol), indan-5-carboxaldehyde (1.3 g, 1.1 equiv.) and TFA (1.2 mL, 2 equiv.) to give the title compound (0.36 g, 14%). $^1$H NMR (CDCl$_3$) δ 7.6 (s, 1H), 7.4 (m, 1H), 6.9–7.2 (m, 6H), 5.1 (s, 1H), 3.3–3.4 (m, 1H), 2.9–3.1 (m, 1H), 2.7–2.9 (m, 6H), 1.9–2.2 (q, 2H).

Intermediate 10

1-(2,3-Dihydrobenzofuran-5-yl)-2,3,4,9-tetrahydro-1H-β-carboline

This product was prepared using a two-step procedure. A solution of tryptamine (32.4 g, 0.2 mol) and 2,3-dihydrobenzofuran-5-carboxaldehyde (30.0 g, 1 equiv.) in toluene (1 L) was heated under reflux for 4 hours. After removal of 4 mL of water and evaporation of toluene the residue was dissolved in DCM (1 L) in the presence of TFA (31 mL, 2 equiv.). The resulting mixture was stirred at rt for 16 hours. Then 1 L of a saturated aqueous solution of NaHCO$_3$ was added. After extraction with DCM and drying over MgSO$_4$, the organic solution was evaporated in vacuo. Recrystallization from DCM:iPr$_2$O (2:30) gave the title compound as white crystals in a 80% yield. $^1$H NMR (CDCl$_3$) δ 7.6 (s, 1H), 7.5–7.6 (m, 1H), 7–7.3 (m, 5H), 6.7–6.75 (d, 1H), 5.1 (s, 1H), 4.5–4.6 (t, 2H), 3.3–3.45 (m, 1H), 3.05–3.2 (t, 3H), 2.7–3 (m, 2H).

Intermediate 11

1-(4-Isopropylphenyl)-2,3,4,9-tetrahydro-1H-β-carboline

This product was prepared using the same procedure as for Intermediate 1 with tryptamine (5.0 g, 31.2 mmol), 4-isopropylbenzaldehyde (5.08 g, 1.1 equiv.) and TFA (4.8 mL, 2 equiv.) to give the title compound (5.9 g, 67%) as white crystals after recrystallization from iPr$_2$O. MP: 146° C.

Intermediate 12

1-(2,3-Benzofuran-5-yl)-2,3,4,9-tetrahydro-1H-β-carboline

This product was prepared using the same procedure as for Intermediate 1 with tryptamine (2.27 g, 14.1 mmol), 2,3-benzofuran-5-carboxaldehyde (2.1 g, 1 equiv., prepared according to the procedure of Dorn et al. EP 481671A1) and TFA (2.2 mL, 2 equiv.) to give the title compound (3.0 g, 74%) as white crystals after recrystallization from cyclohexane. MP: 134–136° C.

Intermediate 13

1-(2,3-Dihydrobenzo[1,4]dioxin-6-yl)-2,3,4,9-tetrahydro-1H-β-carboline

This product was prepared using the same procedure as for Intermediate 1 with tryptamine (4.92 g, 30.7 mmol), 2,3-dihydrobenzo[1,4]dioxin-6-carboxaldehyde (5.05 g, 1.0 equiv.) and TFA (5.0 mL, 2 equiv.) to give the title compound (7.05 g, 75%) as white crystals after recrystallization from iPr$_2$O. MP: 144° C.

Intermediate 14

1-(3-Fluoro-4-methoxyphenyl)-2,3,4,9-tetrahydro-1H-β-carboline

This product was prepared using the same procedure as for Intermediate 1 with tryptamine (4.80 g, 30.0 mmol), 3-fluoro-4-methoxybenzaldehyde (4.86 g, 1.05 equiv.) and TFA (4.6 mL, 2 equiv.) to give the title compound (5.2 g, 59%) as white crystals. MP: 68° C.

Intermediate 15

1-(3,4-Difluorophenyl)-2,3,4,9-tetrahydro-1H-β-carboline

This product was prepared using the same procedure as for Intermediate 1 with tryptamine (5.4 g, 33.5 mmol), 3,4-difluorobenzaldehyde (5.0 g, 1.05 equiv.) and TFA (5.2 mL, 2 equiv.) to give the title compound (7.8 g, 82%) as white crystals. MP: 151° C.

Intermediate 16

1-(3,4-Methylenedioxyphenyl)-6-fluoro-2,3,4,9-tetrahydro-1H-β-carboline

This product was prepared using the same procedure as for Intermediate 1 with 5-fluorotryptamine (1.59 g, 8.9 mmol), 3,4-methylenedioxybenzaldehyde (1.47 g, 1.1 equiv.) and TFA (1.4 mL, 2 equiv.) to give the title compound (2.34 g, 85%) as white crystals. MP: 172° C.

Analysis for $C_{18}H_{15}FN_2O_2$: Calculated: C, 69.67; H, 4.87; N, 6.12. Found: C, 69.47; H, 4.85; N, 6.23%

Intermediate 17

1-(2-Chlorophenyl)-2,3,4,9-tetrahydro-1H-β-carboline

This product was prepared using the same procedure as for Intermediate 1 with tryptamine (1.0 g, 6.2 mmol), 2-chlorobenzaldehyde (0.7 mL, 1.0 equiv.) and TFA (1.0 mL, 2 equiv.) to give the title compound (1.2 g, 69%). $^1$H NMR (CDCl$_3$) δ 7.6 (s, 1H), 7.45 (d, 1H), 7.40 (d, 1H), 6.9–7.2 (m, 6H), 5.6 (s, 1H), 3.2–3.0 (m, 2H), 2.9–2.7 (m, 2H), 2.4 (s, 1H).

Intermediate 18

(S)-1-(3,4-Methylenedioxyphenyl)-2,3,4,9-tetrahydro-1H-β-carboline (S)-1-(3,4-Methylenedioxyphenyl)-2,3,4,9-tetrahydro-1H-β-carboline was obtained from the resolution of the corresponding racemic amine with N-acetyl-(L)-Leucine (Sigma) in MeOH followed by a recrystallization from MeOH. Treatment of the suspension of the recrystallized material in DCM with a saturated aqueous solution of NaHCO$_3$ gave the enantiomerically pure (S)-1-(3,4-methylene-dioxyphenyl)-2,3,4,9-tetrahydro-1H-β-carboline as beige crystals in a 55% yield. MP: 173° C.

Analysis for $C_{18}H_{16}N_2O_2$. 0.35H$_2$O: Calculated: C, 72.39; H, 5.64; N, 9.38. Found: C, 72.35; H, 5.44; N, 9.1%.

$[\alpha]D^{19.6}$=−35 (c=0.53, MeOH).

Intermediate 19

(R)-1-(3,4-Methylenedioxyphenyl)-2,3,4,9-tetrahydro-1H-β-carboline

Following the same protocol as for Intermediate 18 (R)-1-(3,4-methylenedioxyphenyl)-2,3,4,9-tetrahydro-1H-β-carboline was obtained from the resolution of the corresponding racemic amine with N-acetyl-(D)-Leucine (Sigma) in MeOH followed by a recrystallization from MeOH. Treatment of the suspension of the recrystallized material in DCM with a saturated aqueous solution of NaHCO$_3$ gave the enantiomerically pure (R)-1-(3,4-methylene-dioxyphenyl)-2,3,4,9-tetrahydro-1H-β-carboline as white crystals in a 59% yield. MP: 92–94° C.

Analysis for $C_{18}H_{16}N_2O_2$ Calculated: C, 73.95; H, 5.52; N, 9.58. Found: C, 73.72; H, 5.52; N, 9.52%.

$[\alpha]D^{21.}$=34 (c=0.50, MeOH).

Intermediate 20

(R)-1-(2,3-Dihydrobenzofuran-5-yl)-2,3,4,9-tetrahydro-1H-β-carboline

Following the same protocol as for Intermediate 18 (R)-1-(2,3-dihydrobenzofuran-5-yl)-2,3,4,9-tetrahydro-1H-β-carboline was obtained from the resolution of the corresponding racemic amine with N-acetyl-(D)-Leucine (Sigma) in MeOH:EtOAc followed by a recrystallization from MeOH. Treatment of the suspension of the recrystallized material in DCM with a saturated aqueous solution of NaHCO$_3$ gave the enantiomerically pure (R)-1-(2,3-dihydrobenzo-furan- 5-yl)-2,3,4,9-tetrahydro-1H-β-carboline as white crystals in a 55% yield. MP: 98–99° C.

Analysis for $C_{19}H_{18}N_2O$. 0.15H$_2$O: Calculated: C, 77.87; H, 6.29; N, 9.56. Found: C, 77.83; H, 6.33; N, 9.44%

$[\alpha]D^{21}$=42 (c=0.50, MeOH).

Intermediate 21

(S)-1-(4-(2,3-Dihydrobenzo(b)furan)-2,3,4,9-tetrahydro-1H-β-carboline

Following the same protocol as for Intermediate 18 (S)-1-(2,3-dihydrobenzofuran-5-yl)-2,3,4,9-tetrahydro-1H-β-carboline was obtained from the resolution of the corresponding racemic amine with N-acetyl-(L)-Leucine (Sigma) in MeOH/EtOAc followed by a recrystallization from MeOH. Treatment of the suspension of the recrystallized material in DCM with a saturated aqueous solution of NaHCO$_3$ gave the enantiomerically pure (S)-1-(2,3-dihydrobenzo-furan-5-yl)-2,3,4,9-tetrahydro-1H-β-carboline as a pale yellow powder in a 45% yield. MP: 175° C.

Analysis for $C_{19}H_{18}N_2O$. 1.0H$_2$O: Calculated: C, 74.0; H, 6.54; N, 9.08. Found: C, 74.01; H, 5.88; N, 8.92%.

$[\alpha]D^{19.7}$=−49 (c=0.50, MeOH)

Intermediate 22

(E)-3-(4-Ureidophenyl)acrylic acid

A stirred solution of (E)-3-(4-aminophenyl)acrylic acid (1.0 g, 5.0 mmol) and potassium isocyanate (2.0 g, 5 equiv.) in a mixture of water and acetic acid (50 mL) was heated at 100° C. for 12 hours. After cooling, a white solid precipitated out. Filtration, washing of the filter cake with a mixture of water and MeOH, and drying it in vacuo gave the title compound (0.82 g, 80%) as a white solid. MP>350° C.

Intermediate 23

(E)-3-(4-Acetylmethylaminophenyl)acrylic acid

A stirred solution of N-(4-formylphenyl)-N-methylacetamide (1.0 g, 5.64 mmol), malonic acid (1.06 g, 1.8 equiv.) and piperidine (0.1 g, catalytic amount) in pyridine (3.5 mL) was heated at 60° C. for 12 hours. Pouring the resulting mixture into HCl (1N) gave a precipitate. Filtration gave the title compound (1.2 g, 98%) as a white solid. MP: 213–215° C.

Analysis for $C_{12}H_{13}NO_3$. 0.2H$_2$O Calculated: C, 64.68; H, 6.06; N, 6.29. Found: C, 64.43; H, 6.18; N, 6.36%.

N-(4-Formylphenyl)-N-methylacetamide (1.0 g, 46%) was obtained as an oil from N-(4-formylphenyl)acetamide (2.0 g, 12.2 mmol) in THF in the presence of iodomethane (1.2 mL, 1.5 equiv.) and NaH (0.73 g, 1.5 equiv., 60% in mineral oil).

$^1$H NMR (CDCl$_3$, 250 MHz) δ 2.0 (s, 3H), 3.4 (s, 3H), 7.4 (d, 2H), 8.0 (d, 2H).

Intermediate 24

(E)-3-[4-(2-Methoxyethylcarbamoyl)phenyl]acrylic Acid

The same method was employed as in the preparation of Intermediate 23 but starting from 4-formyl-N-(2-methoxyethyl)benzamide to give the title compound as a white powder in a 57% yield. MP: 205° C.

4-Formyl-N-(2-methoxyethyl)benzamide (158 mg, 48%) was obtained by oxidation of 4-hydroxymethyl-N-(2-methoxy-ethyl)benzamide (330 mg, 1.6 mmol) in DCM in the presence of MnO$_2$ (3.0 g, 22 equiv.).

$^1$H NMR (CDCl$_3$, 250 MHz) δ 9.9 (s, 1H), 7.8 (s, 4H), 6.8 (s, 1H), 3.4–3.6 (m, 4H), 3.2 (s, 3H).

4-Hydroxymethyl-N-(2-methoxyethyl)benzamide (330 mg, 14%) was obtained as an oil (Rf=0.7, DCM:MeOH (9:1)) by coupling 4-(hydroxymethyl)benzoic acid (1.0 g, 6.5 mmol) with 2-methoxyethylamine (0.6 mL, 6.5 mmol) in the presence of Et$_3$N (0.95 mL, 1.0 equiv.), EDCl (1.2 g, 1.0 equiv.) and HOBT (0.88 g, 1.0 equiv.).

Intermediate 25

(E)-[4-(2-Dimethylaminoethoxy)phenyl]acrylic acid

The same method was employed as in the preparation of Intermediate 23 but starting from 4-(2-dimethylaminoethoxy)benzaldehyde to give the title compound as a white powder in a 100% yield. MP: 243° C.

4-(2-Dimethylaminoethoxy)benzaldehyde (20.6 g, 65%) was obtained by alklylation of 4-hydroxybenzaldehyde (20 g, 164 mmol) in DMF with dimethylaminoethyl chloride (144 g, 8 equiv.) and $K_2CO_3$ (24.9 g, 1.1 equiv.) for 16 hours at 80° C.

$^1$H NMR (CDCl$_3$, 250 MHz) δ 9.85 (s, 1H), 7.9–7.8 (d, 2H), 7–6.9 (d, 2H), 4.2 (t, 2H), 2.7 (t, 2H), 2.3 (s, 6H).

Intermediate 26

(E)-3-[4-(2-Morpholin-4-yl-ethylcarbamoyl)phenyl] acrylic acid

The same method was employed as in the preparation of Intermediate 23 but starting from 4-formyl-N-(2-morpholin-4-yl-ethyl)benzamide to give the title compound as a gummy solid.

4-Formyl-N-(2-morpholin-4-yl-ethyl)benzamide (0.14 g, 55%) was obtained by oxidation of 4-hydroxymethyl-N-(2-morpholin-4-yl-ethyl)benzamide (0.24 g, 0.9 mmol) and $MnO_2$ (1.73 g, 20 mmol).

$^1$H NMR (CDCl$_3$, 250 MHz) δ 10 (s, 1H), 7.9 (s, 4H), 6.8 (s, 1H), 3.5 (t, 5H), 2.6 (t, 2H), 2.3 (m, 5H).

4-Hydroxymethyl-N-(2-morpholin-4-yl-ethyl)benzamide (240 mg, 14%) was obtained as a colorless oil (Rf=0.6, DCM:MeOH (9:1)) by coupling 4-(hydroxymethyl)benzoic acid (1.0 g, 6.5 mmol) with 2-morpholinethylamine (0.85 g (1.0 equiv.) in the presence of Et$_3$N (0.95 mL, 1.0 equiv.), EDCl (1.2 g, 1.0 equiv.) and HOBT (0.88 g, 1.0 equiv.).

Intermediate 27

(E)-3-(4-Cyclohexylcarbamoylphenyl)acrylic acid

The same method was employed as in the preparation of Intermediate 23 but starting from N-cyclohexyl-4-formylbenzamide to give the title compound as a white powder in a 54% yield. MP: 214° C.

N-Cyclohexyl-4-formylbenzamide (0.6 g, 60%) was obtained by oxidation of N-cyclohexyl-4-(hydroxymethyl) benzamide (1.0 g, 4.29 mol) with $MnO_2$ (0.2 g, 22 equiv.), as a white powder. MP: 163° C.

$^1$H NMR (CDCl$_3$, 250 MHz) δ 10 (s, 1H), 7.95 (s, 4H), 6.6 (s, 1H), 4.1 (m, 1H), 3.9–3.7 (m, 3H), 3.4–3.3 (m, 1H), 2.1–1.9 (m, 2H); 1.8–1.7 (m, 2H).

N-Cyclohexyl-4-(hydroxymethyl)benzamide (1.0 g, 66%) was obtained as white crystals by coupling 4-(hydroxymethyl)benzoic acid with cyclohexylamine (0.75 mL, 1 equiv.) in the presence of Et$_3$N (0.95 mL, 1.0 equiv.), ELCI (1.2 g, 1.0 equiv.) and HOBT (0.88 g, 1.0 equiv.). MP: 185° C.

$^1$H NMR (CDCl$_3$, 250 MHz) δ 7.8–7.7 (d, 2H), 7.5–7.4 (d, 2H), 6.8 (s, 1H), 4.8 (s, 2H), 4.2 (m, 1H), 4.0–3.75 (m, 2H), 3.4–3.3 (m, 1H), 2.7 (m, 1H), 2–1.9 (m, 2H), 1.6 (m, 1H), 1.1 (m, 1H).

Intermediate 28

(E)-3-{4-[(Tetrahydrofuran-2-ylmethyl)carbamoyl]-phenyl}acrylic Acid

The same method was employed as in the preparation of Intermediate 23 but starting from 4-formyl-N-(tetrahydrofuran-2-ylmethyl)benzamide to give the title compound as a white powder in a 49% yield. MP: 215° C.

4-Formyl-N-(tetrahydrofuran-2-ylmethyl)benzamide (0.36 g, 50%) (Rf=0.3, DCM:MeOH) was obtained as an oil by oxidation of 4-hydroxymethyl-N-(tetrahydrofuran-2-ylmethyl)benzamide (0.72 g, 3.0 mmol) with $MnO_2$ (0.36 g, 22 equiv.).

4-Hydroxymethyl-N-(tetrahydrofuran-2-ylmethyl) benzamide (0.72 g, 46%) was obtained as a colorless oil (Rf=0.6, DCM:MeOH (9:1)) by coupling 4-(hydroxymethyl)benzoic acid (1.0 g, 6.5 mmol) with tetrahydrofuran-2-yl-methylamine (0.67 mL, 1.0 equiv.) in the presence of Et$_3$N (0.95 mL, 1.0 equiv.), EDCl (1.2 g, 1.0 equiv.) and HOBT (0.88 g, 1.0 equiv.).

Intermediate 29

(E)-1-[4-(2-Carboxyvinyl)benzoyl]piperidine-4-carboxylic Acid, Ethyl Ester

The same method was employed as in the preparation of Intermediate 23 but starting from 1-(4-formylbenzoyl)-piperidine-4-carboxylic acid, ethyl ester to give the title compound as a white powder in a 46% yield. MP: 165° C.

1-(4-Formylbenzoyl)piperidine-4-carboxylic acid, ethyl ester (960 mg, 49%) (Rf=0.6, DCM:MeOH(95:5)) was obtained as an oil by oxidation of 1-(4-hydroxymethyl-benzoyl)piperidine-4-carboxylic acid, ethyl ester (2.0 g, 6.8 mmol) with $MnO_2$ (13.1 g, 22 equiv.).

$^1$H NMR (CDCl$_3$, 250 MHz) δ 10.0 (s, 1H), 7.9 (d, 2H), 7.5 (d, 2H), 4.5 (d, 1H), 4.1 (q, 2H), 3.6 (d, 1H), 3.1 (br s, 2H), 2.5 (m, 1H), 2.1–1.6 (m, 4H), 1.2 (t, 3H).

1-(4-Hydroxymethylbenzoyl)piperidine-4-carboxylic acid, ethyl ester (1.9 g, 100%) was obtained as a colorless oil (Rf=0.1, DCM:MeOH (95:5)) by coupling 4-(hydroxymethyl)benzoic acid (1.0 g, 6.5 mmol) with 4-piperidine-4-carboxylic acid, ethyl ester (1 mL, 6.5 mmol) in the presence of Et$_3$N (0.95 mL, 1.0 equiv.), EDCl (1.2 g, 1.0 equiv.) and HOBT (0.88 g, 1.0 equiv.).

$^1$H NMR (CDCl$_3$, 250 MHz) δ 7.2 (s, 4H), 4.5 (s, 2H), 4.3 (br s, 1H), 4.1 (q, 2H), 3.6 (br s, 1H), 3 (t, 2H), 2.5 (m, 1H), 2.1–1.6 (m, 4H), 1.2 (t, 3H).

Intermediate 30

(E)-3-(4-Ethoxycarbonylmethylphenyl)acrylic acid

The same method was employed as in the preparation of Intermediate 23 but starting from (4-formylphenyl)acetic acid, ethyl ester gave the title compound as a yellow gum in a 52% yield.

$^1$H NMR (CDCl$_3$, 250 MHz) δ 7.8–7.6 (m, 3H), 7.4–7.3 (d, 2H), 6.9–6.8 (d, 1H), 4.1–3.9 (q, 2H), 3.55 (s, 2H), 1.2 (t, 3H).

4-(4-Formylphenyl)acetic acid, ethyl ester was prepared according to the procedure of Biagi et al., *Farmaco-Ed. Sc.* 1988, 43, 597–611.

Intermediate 31

(E)-1-[4-(2-Carboxyvinyl)phenyl]piperidine-4-carboxylic Acid, Ethyl Ester

The same method was employed as in the preparation of Intermediate 23 but starting from 1-(4-formylphenyl)-piperidine-4-carboxylic acid, ethyl ester to give the title compound as a yellow powder in a 86% yield. MP: 212° C.

Analysis for $C_{17}H_{21}NO_4 \cdot 0.15H_2O$ Calculated: C, 66.71; H, 7.01; N, 4.58. Found: C, 66.77; H, 7.01; N, 4.79%.

1-(4-Formylphenyl)piperidine-4-carboxylic acid, ethyl ester was prepared according to the procedure of Duckworth et al. EP 68669A1.

Intermediate 32

(E)-4-(2-Carboxyvinyl)-3-chlorobenzoic acid, methyl Ester

The same method was employed as in the preparation of Intermediate 23 but starting from 3-chloro-4-formylbenzoic acid, methyl ester to give the title compound as a white powder in a 58% yield. MP: 221° C.

3-Chloro-4-formylbenzoic acid, methyl ester (4.0 g, 81%) was prepared by reaction of 4-bromomethyl-3-chlorobenzoic acid, methyl ester (6.0 g, 26 mmol) with silver p-toluenesulfonate (15.0 g, 2.0 equiv.) in 100 mL of DMSO in the presence of $Et_3N$ (100 mL, 7 equiv.) at rt for 1 hour. Quenching the resulting mixture with 100 mL of water, extraction with 2×100 mL of EtOAc, washing with 50 mL of water, drying over $Na_2SO_4$ and flash chromatography with cyclohexane:EtOAc (95:5) as eluting solvent, gave the title compound (2.3 g, 42%) as an oil.

$^1$H NMR ($CDCl_3$, 250 MHz) δ 10.5 (s, 1H), 8.1 (s, 1H), 7.8–7.7 (d, 1H), 7.4–7.3 (d, 1H), 3.8 (s, 3H).

4-Bromomethyl-3-chlorobenzoic acid, methyl ester (6.0 g, 87%) was obtained as an orange oil by refluxing for 12 hours 4-methyl-3-chlorobenzoic acid, methyl ester (5.7 g, 31 mmol) with NBS (6.4 g, 1.2 equiv.) in the presence of a catalytic amount of AIBN in $CCl_4$.

$^1$H NMR ($CDCl_3$, 250 MHz) δ 8.0 (s, 1H), 7.9–7.8 (d, 1H), 7.45–7.35 (d, 1H), 4.5 (s, 1H), 3.9 (s, 3H).

4-Methyl-3-chlorobenzoic acid, methyl ester (5.7 g, 53%) was obtained as an orange oil by refluxing overnight 4-methyl-3-chlorobenzoic acid (9.9 g, 58 mmol) in MeOH in the presence of PTSA.

$^1$H NMR ($CDCl_3$, 250 MHz) δ 8.0 (d, 1H), 7.85 (dd, 1H), 7.3 (d, 1H), 4.0 (s, 3H), 2.5 (s, 3H).

Intermediate 33

(E)-5-(2-Carboxyvinyl)-2-chlorobenzoic acid, methyl ester

The same method was employed as in the preparation of Intermediate 32 but starting from 2-chloro-5-formylbenzoic acid, methyl ester to give the title compound as a yellow powder in a 76% yield. MP: 194° C.

2-Chloro-5-formylbenzoic acid, methyl ester (0.6 g, 25%) was obtained a gum by reaction of 5-bromomethyl-2-chlorobenzoic acid, methyl ester (3.1 g, 11.7 mmol) with silver p-toluenesulfonate (6.4 g, 1.75 equiv.) in DMSO in the presence of $Et_3N$ (1.2 mL, 7 equiv.) at rt for 1 hour.

$^1$H NMR ($CDCl_3$, 250 MHz) δ 10 (s, 1H), 8.4 (d, 1H), 7.9 (dd, 1H), 7.7–7.6 (d, 1H), 4.0 (s, 3H).

5-Bromomethyl-2-chlorobenzoic acid, methyl ester (3.1 g, 11.7 mmol) was obtained as a gum in a 45% yield by refluxing for 12 hours 5-methyl-2-chlorobenzoic acid, methyl ester (4.78 g, 25.9 mmol) with NBS (5.56, 1.2 equiv.) in the presence of a catalytic amount of AIBN in $CCl_4$.

$^1$H NMR ($CDCl_3$, 250 MHz) δ 7.9 (s, 1H), 7.4 (br s, 2H) 4.5 (s, 2H), 3.9 (s, 3H).

5-Methyl-2-chlorobenzoic acid, methyl ester (4.78 g, 90%) was obtained as a brown oil, by refluxing overnight 3-methyl-4-chlorobenzoic acid (5.0 g, 29 mmol) in MeOH in the presence of a catalytic amount of PTSA.

$^1$H NMR ($CDCl_3$, 250 MHz) δ 7.6 (s, 1H), 7.25–7.2 (d, 1H), 7.15–7.1 (d, 1H), 3.8 (s, 3H), 2.2 (s, 3H).

Intermediate 34

(E)-(3-Hydroxy-4-nitrophenyl)acrylic acid

The same method was employed as in the preparation of Intermediate 23 but starting from 3-hydroxy-4-nitrobenzaldehyde to give the title compound as a white powder in a 88% yield. MP: 237° C.

Intermediate 35

(E)-(3,5-Dimethyl-4-hydroxyphenyl)acrylic acid

The same method was employed as in the preparation of Intermediate 23 but starting from 3,5-dimethyl-4-hydroxybenzaldehyde gave the title compound as a white powder in a 94% yield. MP: 190° C.

Intermediate 36

(E)-(3-Nitro-4-hydroxy-5-methoxphenyl)acrylic acid

The same method was employed as in the preparation of Intermediate 23 but starting from 3-nitro-4-hydroxy-5-methoxybenzaldehyde to give the title compound as a white powder in a 75% yield. MP: 248° C.

Intermediate 37

(E)-3-(3-Nitro-2-piperidin-1-yl-phenyl)acrylic Acid

The same method was employed as in the preparation of Intermediate 23 but starting from 2-chloro-3-nitrobenzaldehyde to give the title compound as a yellow powder in a 100% yield.

$^1$H NMR ($CDCl_3$, 250 MHz) δ 10.3 (br s, 1H), 8.1 (d, 1H), 7.65 (dd, 1H), 7.55 (dd, 1H), 7.05 (t, 41H), 6.3 (d, 1H), 2.9 (m, 2H), 1.6 (m, 6H).

2-Chloro-3-nitrobenzaldehyde (150 mg, 20%) was prepared by reaction of 1-bromomethyl-2-chloro-3-nitrobenzene (1.0 g, 3.9 mmol) with silver p-toluenesulfonate (1.94 g, 1.75 equiv.) in DMSO in the presence of $Et_3N$ (4 mL, 7 equiv.) at rt for 1 hour.

$^1$H NMR ($CDCl_3$, 250 MHz) δ .10.5 (s, 1H), 8.1 (dd, 1H), 8.0 (dd, 1H), 7.5 (t, 1H).

1-Bromomethyl-2-chloro-3-nitrobenzene (13.3 g, 68%) was obtained as a yellow oil by refluxing for 2 hours a mixture of 2-chloro-3-nitrotoluene (10 g, 58 mmol) with NBS (10.3 g, 1 equiv.) in the presence of a catalytic amount of AIBN in $CCl_4$.

$^1$H NMR ($CDCl_3$, 250 MHz) δ 7.75 (dd, 1H), 7.65 (dd, 1H), 7.45 (m, 1H), 4.6 (s, 2H).

Intermediate 38

(E)-3-(4-Methyl-3,4-dihydro-2H-benzo[1,4]oxazin-6-yl)acrylic Acid

The same method was employed as in the preparation of Intermediate 23 but starting from 4-methyl-3,4-dihydro-2H-benzo[1,4]oxazin-6-carboxaldehyde (prepared according to the procedure of Kotha et al., *Heterocyles* 1994, 38, 5–8) to give the title compound as a yellow powder in a 61% yield. MP: 190° C.

Analysis for $C_{12}H_{13}NO_5$ Calculated: C, 65.74; H, 5.98; N, 6.39. Found: C, 65.85; H, 6.04; N, 6.33%.

Intermediate 39

(E)-3-(2-Hydroxy-5-nitrophenyl)acrylic acid

The same method was employed as in the preparation of Intermediate 23 but starting from 2-hydroxy-5-nitro benzaldehyde to give the title compound as a yellow powder in a 11% yield. MP: 265–267° C.

Intermediate 40

(E)-3-[3-(Trifluoromethanesulfonyloxy)phenyl] acrylic acid

The same method was employed as in the preparation of Intermediate 23 but starting from trifluoromethanesulfonic acid, 3-formylphenyl ester (prepared according to the procedure of Kingsbury et al., *J. Med. Chem.* 1993, 36, 3308–3320) to give the title compound as pink crystals in a 36% yield. MP: 107° C.

Intermediate 41

(E)-3-[4-(Trifluoromethanesulfonyloxy)phenyl] acrylic Acid

The same method was employed as in the preparation of Intermediate 23 but starting from trifluoromethanesulfonic acid, 4-formylphenyl ester (prepared according to the procedure of Creary et al., *J. Org. Chem.* 1983, 48(17), 2887–2891) to give the title compound as white crystals in a 61% yield. MP: 194° C.

Intermediate 42

(E)-3-[4-(2-Pyrrolidin-1-ylethoxy)phenyl]acrylic Acid

The same method was employed as in the preparation of Intermediate 23 but starting from 4-(2-pyrrolidin-1-ylethoxy)benzaldehyde (prepared according to the procedure of Sakaguchi et al., *Chem. Pharm. Bull.* 1992, 40, 202–211) to give the title compound as a yellow solid in a 60% yield. MP: 183° C.

Intermediate 43

(E)-3-(4-Pyrrolidin-1-ylphenyl)acrylic acid

The same method was employed as in the preparation of Intermediate 23 but starting from (4-pyrrolidin-1-ylphenyl)benzaldehyde (prepared according to the procedure of Duckworth et al., EP 68669A1) to give the title compound as a yellow solid in a 65% yield. MP: 265° C.

Intermediate 44

(E)-3-(4-Imidazol-1-ylphenyl)acrylic Acid

The same method was employed as in the preparation of Intermediate 23 but starting from 4-imidazol-1-ylbenzaldehyde (prepared according to the procedure of Sircar et al., *J. Med. Chem.* 1987, 30, 1023–1029) to give the title compound as pink crystals in a 55% yield. MP: 326–327° C.

Intermediate 45

(E)-(S)-3-[4-(1-Methylpyrrolidin-2-ylmethoxy)phenyl]acrylic Acid

The same method was employed as in the preparation of Intermediate 23 but starting from (S)-4-(1-methylpyrrolidin-2-ylmethoxy)benzaldehyde to give the title compound as a beige powder in a 66% yield. MP: 251° C.

$[\alpha]_D^{21}$=−9 (c=0.35, pyridine).

(S)-4-(1-Methylpyrrolidin-2-ylmethoxy)benzaldehyde (0.96 g, 44%) was obtained as an orange oil by refluxing for 12 hours at 80° C., 4-hydroxybenzaldehyde (1.22 g, 10 mmol) with (S)-2-chloromethyl-1-methylpyrrolidine, hydrochloride (2.55 g, 1.5 equiv.) in DMF in the presence of $K_2CO_3$ (3.82 g, 2.8 equiv.).

$^1$H NMR (CDCl$_3$, 250 MHz) δ 9.9 (s, 1H), 7.85 (d, 2H), 7.0 (d, 2H), 4.1 (dd, 1H), 4.0 (dd, 1H), 3.1 (d tr, 1H), 2.7 (m, 1H), 2.5 (s, 3H), 2.3 (m, 1H), 2 (m, 1H), 1.8 (m, 3H).

(S)-2-Chloromethyl-1-methylpyrrolidine, hydrochloride was prepared according to the procedure of D'Ambra et al., EP 444451 A2.

Intermediate 46

(E)-3-[4-(2-Dimethylamino-1-methylethoxy)phenyl] acrylic Acid

The same method was employed as in the preparation of Intermediate 23 but starting from 4-(2-dimethylamino-1-methylethoxy)benzaldehyde to give the title compound as a white powder in a 86% yield. MP: 235° C.

Analysis for $C_{14}H_{19}NO_3$.HCl Calculated: C, 58.84; H, 7.05; N, 4.9. Found: C, 58.49; H, 7.08; N, 5.05%.

4-(2-Dimethylamino-1-methylethoxy)benzaldehyde (2.1 g, 18%) was obtained as an orange oil by refluxing for 12 hours, 4-hydroxybenzaldehyde (7 g, 57 mmol), $K_2CO_3$ (8.7 g, 1.1 equiv.) and 2-chloropropyldimethylamine, hydrochloride (13.6 g, 1.5 equiv.) in DMF.

$^1$H NMR (CDCl$_3$, 250 MHz) δ 9.7 (s, 1H), 7.65 (d, 2H), 6.85 (d, 2H), 4.5 (m, 1H), 2.5 (m, 1H), 2.3 (m, 1H), 2.1 (m, 6H), 1.2 (d, 3H).

Intermediate 47

(E)-3-[4-(4-Methylpiperazin-1-yl)phenyl]acrylic Acid

The same method was employed as in the preparation of Intermediate 23 but starting from 4-(4-methylpiperazin-1-yl)benzaldehyde (prepared according to the procedure of Sakai et al., *Chem. Pharm. Bull.* 1980, 28, 2384–2393) to give the title compound as a white powder in a 65% yield. MP: 223–226° C.

Intermediate 48

(E)-3-[4-(2-Dimethylaminopropoxy)phenyl]acrylic acid

The same method was employed as in the preparation of Intermediate 23 but starting from 4-(2-dimethylaminopropoxy)benzaldehyde (prepared according to the procedure of Mizzoni U.S. Pat. No. 3,483,209) to give the title compound as a beige powder in a 100% yield. MP: 231° C.

Intermediate 49

(E)-3-[4-(2-Morpholin-4-ylethoxy)phenyl]acrylic Acid

The same method was employed as in the preparation of Intermediate 23 but starting from 4-(2-morpholin-4-ylethoxy)benzaldehyde (prepared according to the procedure of Naruto et al., *J. Med. Chem.* 1982, 25, 1240–1245) to give the title compound as a white powder in a 96% yield. MP: 228° C.

Intermediate 50

(E)-3-{4-[2-(Ethylmethylamino)ethoxy]phenyl}acrylic Acid

The same method was employed as in the preparation of Intermediate 23 but starting from 4-[2-(ethylmethylamino)

ethoxy]benzaldehyde to give the title compound as a beige powder in a 73% yield. MP: 206° C.

Analysis for $C_{14}H_{19}NO_3 \cdot HCl$ Calculated: C, 58.84; H, 7.05; N, 4.9. Found: C, 59.08; H, 7.07; N, 5.02%.

4-[2-(Ethylmethylamino)ethoxy]benzaldehyde (5.0 g, 59%) was obtained as a brown oil by refluxing for 12 hours 4-hydroxybenzaldehyde (5 g, 41 mmol), $K_2CO_3$ (6.2 g, 1.1 equiv.) and (2-chloroethyl)ethylmethylamine, hydrochloride (9.7 g, 1.5 equiv.) in DMF.

$^1$H NMR (CDCl$_3$, 250 MHz) δ 9.7 (s, 1H), 7.7 (d, 2H), 6.9 (d, 2H), 4.1 (t, 2H), 2.6 (t, 2H), 2. (s, 6H).

Intermediate 51

(E)-3-[4-(3-Dimethylaminopropenyl)phenyl]acrylic Acid

This product was prepared by refluxing for four hours, (E)-3-[4-(3-dimethylaminopropenyl)phenyl]acrylic acid, methyl ester with NaOH (0.16 g, 2 equiv.) in 10 mL of MeOH. After evaporation of the solvent in vacuo, treatment with 5 mL of HCl (1N) gave the title compound (0.4 g, 85%) as a gummy orange solid.

$^1$H NMR (CDCl$_3$, 250 MHz) δ 7.6 (d, 2H), 7.4 (d, 1H), 7.2 (d, 2H), 6.6 (d, 1H), 6.4 (d, 1H), 5.8 (m, 1H), 3.7 (d, 2H), 2.6 (s, 6H).

(E)-3-[4-(3-Dimethylaminopropenyl)phenyl]acrylic acid, methyl ester was prepared by the following way: (2-dimethylaminoethyl)triphenylphosphonium bromide (7.2 g, 17.4 mmol) in 30 mL of DMF was treated with KHMDS (27 mL, 1.01 equiv., 0.5 M in toluene) at −78° C. for one hour. At −40° C., 3-(4-formylphenyl)acrylic acid, methyl ester (2.54 g, 13.3 mmol, prepared according to the procedure of Syper et al., *Synthesis*, 1984, 9, 747–752) was added dropwise. The resulting mixture was stirred for 12 hours at rt and quenched with water. Extraction with EtOAc, drying over MgSO$_4$ and evaporation in vacuo gave a residue that was purified via flash chromatography with DCM:MeOH (90:10) as eluting solvent. The title compound (1.1 g, 34%) was obtained as an orange oil.

$^1$H NMR (CDCl$_3$, 250 MHz) δ 7.6 (d, 1H), 7.4 (d, 2H), 7.2 (d, 2H), 6.5 (d, 1H), 6.4 (d, 1H), 5.8 (m, 1H), 3.2 (dd, 2H), 2.1 (s, 6H).

Intermediate 52

(E)-3-[4-(2-(Tertbutyldimethylsilanyloxy)-3-dimethyl-aminopropenyl)phenyl]acrylic acid This product was prepared by refluxing for four hours (E)-3-[4-(2-(tertbutyldimethylsilanyloxy)-3-dimethyl-aminopropanyl]phenyl]acrylic acid, methyl ester (0.8 g, 2.03 mmol) and NaOH (1N) (4 mL, 2 equiv.) in 10 mL of MeOH. Evaporation of the solvent in vacuo and treatment with 5 mL of HCl (1N) gave the title compound (0.4 g, 60%) as a beige solid. MP: 207° C.

(E)-3-[4-(2-(Tertbutyldimethylsilanyloxy)-3-dimethyl-aminopropoxy)phenyl]acrylic acid, methyl ester (0.8 g, 40%) was obtained as a yellow oil by reaction for 4 hours of (E)-3-[4-(3-dimethylamino-2-hydroxypropoxy)phenyl] acrylic acid, methyl ester (1.35 g, 5.13 mmol) with TBDM-SCl (0.93 g, 6.2 mmol) in 50 mL of DMF in the presence of imidazole (0.84 g, 2.4 equiv.). After evaporation in vacuo, the residue was taken up in DCM, washed with water, dried over MgSO$_4$, evaporated in vacuo and purified via flash chromatography using DCM:MeOH as eluting solvent.

$^1$H NMR (CDCl$_3$, 250 MHz) δ 7.5 (d, 1H), 7.3 (d, 2H), 6.8 (d, 2H), 6.2 (d, 1H), 4.0 (m, 2H), 3.8 (m, 1H), 3.7 (s, 3H), 2.4–2.2 (m, 2H), 2.1 (s, 6H), 0.7 (s, 9H), 0.0 (d, 6H).

(E)-3-[4-(3-Dimethylamino-2-hydroxypropoxy)phenyl] acrylic acid, methyl ester (1.5 g, 60%) was obtained as an oil by reaction of 4-(3-dimethylamino-2-hydroxypropoxy) benzaldehyde (2.0 g, 8.96 mmol) in 80 mL of toluene with triphenylphosphoranylidene methyl acetate (3.6 g, 1.2 equiv.) at 100° C. for one day. After concentration in vacuo, the residue was taken up in DCM, washed with water, dried over Na$_2$SO$_4$, evaporated in vacuo and purified via flash chromatography using DCM:MeOH (95:5) as eluting solvent.

$^1$H NMR (CDCl$_3$, 250 MHz) δ 7.6 (d, 1H), 7.5 (d, 2H), 7.3 (d, 2H), 6.3 (d, 1H), 4.2 (m, 1H), 4.1 (m, 1H), 3.8 (m, 3H), 3.3 (s, 1H), 2.8 (dd, 1H), 2.6 (dd, 1H), 2.4 (s, 6H).

4-(3-Dimethylamino-2-hydroxypropoxy)benzaldehyde (8.2 g, 61%) was obtained as an a yellow oil, by reaction of 4-oxiranylmethoxybenzaldehyde (6 g, 33.6 mmol, prepared according to the procedure of Baldwin et al., *J. Med. Chem.* 1977, 20, 1024–1029) in 100 mL of MeOH with dimethylamine (34 mL, 2 equiv.). The resulting mixture was stirred at reflux for 2 days. Evaporation in vacuo gave a residue that was taken up in DCM, washed with brine and dried over MgSO$_4$ and evaporated in vacuo.

$^1$H NMR (CDCl$_3$, 250 MHz) δ 9.7 (s, 1H), 7.6 (d, 2H), 7.0 (d, 2H), 4. (m, 3H), 3.6 (s, 1H), 2.5 (dd, 1H), 2.3 (dd, 1H), 2.25 (s, 6H).

Intermediate 53

(E)-3-[4-(2-(Dimethylaminoethylamino)phenyl] acrylic Acid

The same method was employed as in the preparation of Intermediate 23 but starting from 4-[2-(dimethylamino-ethyl)amino]benzaldehyde (prepared according to the procedure of Klaus et al., EP 331983 A2) to give the title compound as an oil in a 100% yield.

$^1$H NMR (CDCl$_3$, 250 MHz) δ 7.5 (d, 1H), 7.2 (d, 2H), 6.5 (d, 2H), 6.1 (d, 1H), 4.6 (s, 1H), 3.0 (m, 2H), 2.5 (t, 2H), 2.2 (s, 6H).

Intermediate 54

(E)-3-{4-[2-(1,3-Dioxo-1,3-dihydroisoindol-2-yl) ethoxy]-phenyl}acrylic acid

The same method was employed as in the preparation of Intermediate 23 but starting from 4-[2-(1,3-dioxo-1,3-dihydroisoindol-2-yl)ethoxy]benzaldehyde (prepared from the procedure of Hindley et al. WO 92/07839) to give the title compound as an oil in a 99% yield.

$^1$H NMR (CDCl$_3$, 250 MHz) δ 12.3 (s, 1H), 7.9 (m, 4H), 7.6 (d, 2H), 7.5 (d, 1H), 7.0 (d, 2H), 6.4 (d, 1H), 4.4 (t, 2H), 4.0 (t, 2H).

Intermediate 55

(E)-3-[4-(2-(Piperidin-1-ylethoxy)phenyl]acrylic Acid

The same method was employed as in the preparation of Intermediate 23 but starting from 4-(2-piperidin-1-yl-ethoxy)benzaldehyde (which was prepared according to the procedure of Naruto et al., *J. Med. Chem.* 1982, 25, 1240–1245), to give the title compound as a white powder in a 60% yield. MP: 231° C.

Intermediate 56

(E)-3-[4-(2-(Tertbutoxycarbonylmethylamino) ethoxy)phenyl]acrylic Acid (E)-3-[4-(2-Methylaminoethoxy)phenyl]acrylic acid (0.8 g, 3.6 mmol) in dioxane (100 mL) was treated with NaOH (2N) (22 mL, 12 equiv.). After one hour of stirring at 70° C., ditertbutyldicarbonate (1.6 g, 2 equiv.) was added slowly. The reaction was judged to be complete after 3 hours of stirring at 70° C. After filtration of the white precipitate, the filtrate was acidified to pH=1 with HCl (1N). A new white solid precipitated out. Filtration and drying in vacuo gave the title compound (0.6 g, 50%) as white crystals.

$^1$H NMR (CDCl$_3$, 250 MHz) δ 7.8 (d, 1H), 7.65 (d, 2H), 7.0 (d, 2H), 6.4 (d, 1H), 4.25 (t, 2H), 3.7 (t, 2H), 3.1 (s, 3H), 1.5 (s, 9H).

(E)-3-[4-(2-Methylaminoethoxy)phenyl]acrylic acid (1.1 g, 41%) was obtained as a white solid by hydrolysis of (E)-3-[4-(2-methylaminoethoxy)phenyl]acrylic acid, methyl ester (3.0 g, 12.0 mmol) with NaOH (6.0 g, 12 equiv.) in MeOH/THF at 40° C.
MP: 245° C.

(E)-3-[4-(2-Methylaminoethoxy)phenyl]acrylic acid, methyl ester (3.0 g, 70%) was obtained as a yellow oil by reaction of trimethylphosphonoacetate (4.2 g, 23.0 mmol) and n-butyl lithium (9.0 mL, 18.0 mmol, 2.0 M in cyclohexane) at −78° C., followed by the addition of 4-(2-methylamino-ethoxy)benzaldehyde (3.2 g, 18.0 mmol) at −40° C. The resulting mixture was stirred at rt for 16 hours, quenched with water, extracted with EtOAc, dried over MgSO$_4$ and concentrated in vacuo.

$^1$H NMR (CDCl$_3$, 250 MHz) δ 7.65 (d, 1H), 7.45 (d, 2H), 6.9 (d, 2H), 6.25 (d, 1H), 4.10 (t, 2H), 3.75 (s, 3H), 2.95 (t, 2H), 2.5 (s, 3H).

4-(2-Methylaminoethoxy)benzaldehyde (3.2 g, 51%) was obtained as a yellow oil by reaction of 4-(2-methylaminoethoxy)benzonitrile (7.0 g, 40.0 mmol) with diisobutylaluminum hydride (40 mL, 1.5 equiv., 1.5 M in toluene) in toluene (400 mL) at −78° C. After 4 hours of stirring at −78° C. the resulting mixture was treated with a mixture of water/MeOH (4 mL). At rt an additional 20 mL of water was added. The resulting suspension was filtered on a bed of celite. The celite was washed with Et$_2$O (3×200 mL). The filtrate was concentrated in vacuo and purified via flash chromatography of silica gel using MeOH:DCM (1:9) as eluting solvent.

$^1$H NMR (CDCl$_3$, 250 MHz) δ 9.8 (s, 1H), 7.8 (d, 2H), 7.0 (d, 2H), 4.1 (t, 2H), 2.9 (t, 2H), 2.5 (s, 3H).

4-(2-Methylaminoethoxy)benzonitrile (0.6 g, 15%) was obtained as a yellow oil by reaction of 4-(2-chloroethoxy) benzonitrile (2.0 g, 11.0 mmol, prepared according to the procedure of Mizuno et al., *Synthesis*, 1979, 9, 688) with methylamine (4.3 mL, 5 equiv., 40% in water) at 70° C. for 16 hours. The resulting mixture was extracted with DCM, dried over MgSO$_4$, concentrated in vacuo and purified via flash chromatography of silica gel using MeOH:DCM (2:8) as eluting solvent, to give the title compound.

$^1$H NMR (CDCl$_3$, 250 MHz) δ 7.6 (d, 2H), 7.0 (d, 2H), 4.1 (t, 2H), 3.0 (t, 2H), 2.5 (s, 3H)

EXAMPLE 1

(E)-1-(1-Phenyl-1,3,4,9-tetrahydro-β-carbolin-2-yl)-3-phenylpropene-1-one

To a solution of Intermediate 1 (0.2 g, 0.81 mmol) and NaHCO$_3$ (0.08 g, 1.2 equiv.) in 10 mL of DCM was added (E)-cinnamoyl chloride (0.2 g, 1.5 equiv.). After 4 hours of stirring at rt the reaction was judged to be completed by tlc monitoring (SiO$_2$, DCM:MeOH 98:2) and was quenched with 5 mL of a saturated aqueous solution of NaHCO$_3$. The reaction mixture was extracted with DCM, washed with brine (5 mL), dried over MgSO$_4$ and concentrated in vacuo. Flash chromatography on a 2×20 cm$^2$ column using DCM-:MeOH (98:2) as eluting solvent and removal of the solvent in vacuo gave after recrystallization from 2-propanol, the title compound (0.1 g, 33%) as white crystals. MP: 130–132° C.

Analysis for C$_{26}$H$_{22}$N$_2$O Calculated: C, 82.51; H, 5.86; N, 7.40. Found: C, 82.24; H, 5.93; N, 7.36%.

EXAMPLE 2

(E)-1-(1-Phenyl-1,3,4,9-tetrahydro-β-carbolin-2-yl)-3-(4-nitrophenyl)propene-1-one The same method as employed as in the preparation of Example 1 but starting from (E)-4-nitrocinnamoyl chloride gave after recrystallization from iPr$_2$O:2-propanol (3:1), the title compound as a yellow powder in a 47% yield.
MP: 230–231° C.

Analysis for C$_{26}$H$_{21}$N$_3$O$_3$ Calculated: C, 73.74; H, 5.00; N, 9.92. Found: C, 73.89; H, 5.12; N, 9.86%.

EXAMPLE 3

(E)-1-(1-Phenyl-1,3,4,9-tetrahydro-β-carbolin-2-yl)-3-(4-trifluoromethylphenyl)propene-1-one The same method as employed in the preparation of Example 1 but starting from (E)-4-trifluoromethylcinnamoyl chloride gave after recrystallization from pentane, the title compound as a white powder in a 41% yield. MP: 211° C.

Analysis for C$_{27}$H$_{21}$F$_3$N$_2$O. 0.4H$_2$O: Calculated: C, 71.48; H, 4.84; N, 6.17; Found: C, 71.84; H, 4.81; N, 6.19%.

EXAMPLE 4

(E)-1-(1-Phenyl-1,3,4,9-tetrahydro-β-carbolin-2-yl)-3-(4-methoxy-phenyl)propene-1-one The same method as employed in the preparation of Example 1 but starting from (E)-4-methoxycinnamoyl chloride gave after recrystallization from 2-propanol, the title compound as white crystals in a 61% yield. MP: 160–163° C.

Analysis for C$_{27}$H$_{24}$N$_2$O$_2$. 0.5 (2-propanol): Calculated: C, 78.06; H, 6.44; N, 6.39; Found: C, 78.04; H, 6.02; N, 5.97%.

EXAMPLE 5

(E)-1-[1-(4-Methoxyphenyl)-1,3,4,9-tetrahydro-β-carbolin-2-yl]-3-(4-trifluoromethylphenyl)propene-1-one The same method as employed in the preparation of Example 1 but starting from Intermediate 2 and (E)-4-trifluoromethylcinnamoyl chloride gave after recrystallization from pentane, the title compound as a white powder in a 61% yield. MP: 130–135° C.

Analysis for C$_{28}$H$_{23}$N$_2$O$_2$F$_3$. 0.3H$_2$O: Calculated: C, 69.79; H, 4.94; N, 5.81. Found: C, 69.9; H, 4.84; N, 5.73%.

EXAMPLE 6

(E)-N-[4-[3-Oxo-3-(1-phenyl-1,3,4,9-tetrahydro-β-carbolin-2-yl)propenyl]phenyl]acetamide To a solution of Intermediate 1 (0.2 g, 0.81 mmol) in 40 mL of DCM were added Et$_3$N (0.13 mL, 1.1 equiv.), DCC (0.18 g, 1.1 equiv.), HOBT (0.12 g, 1.1 equiv.) and (E)-3-(4-acetylaminophenyl)acrylic acid (0.18 g, 1.1 equiv.). After 24 hours of stirring at rt the reaction was judged to be completed by tlc monitoring (SiO$_2$, DCM:MeOH 95:5) and was quenched with 150 mL of water. A white solid precipitated out and was filtered off. The filtrate was extracted with DCM, washed with brine (5 mL), dried over MgSO$_4$ and concentrated in vacuo. Flash chromatography on a 2.5×25 cm$^2$ column of silica gel using DCM:MeOH (98:2) as eluting solvent and removal of the solvent in vacuo gave the title compound (0.18 g, 51%) as yellow crystals after recrystallization from 2-propanol:pentane. MP: 177–180° C.

Analysis for C$_{28}$H$_{25}$N$_3$O$_2$.0.7H$_2$O: Calculated: C, 75.05; H, 5.94; N, 9.38. Found: C, 75.01; H, 5.81; N, 9.22%.

EXAMPLE 7

(E)-1-[1-(4-Methoxyphenyl)-1,3,4, 9-tetrahydro-β-carbolin-2-yl]-3-phenylpropene-1-one The same method as employed in the preparation of Example 1 but starting from Intermediate 2 gave the title compound as white crystals in a 56% yield. MP: 127° C.

Analysis for C$_{27}$H$_{24}$N$_2$O$_2$. 0.5H$_2$O: Calculated: C, 77.67; H, 6.04; N, 6.71. Found: C, 77.91; H, 6.0; N, 6.73%.

EXAMPLE 8

(E)-1-[1-(3,4-Methylenedioxyphenyl)-1,3,4,9-tetrahydro-β-carbolin-2-yl]-3-phenyl-propene-1-one The same method as employed in the preparation of Example 1 but starting from Intermediate 7 gave after recrystallization from 2-propanol:iPr$_2$O (2:8), the title compound as white crystals in a 38% yield. MP: 236–238° C.

Analysis for C$_{27}$H$_{24}$N$_2$O$_2$. 0.5H$_2$O. Calculated: C, 76.76; H, 5.25; N, 6.63. Found: C, 76.87; H, 5.35; N, 6.54%.

EXAMPLE 9

(E)-1-(1-Phenyl-1 3,4,9-tetrahydro-β-carbolin-2-yl)-3-(4-formylphenyl)propene-1-one The same method as employed in the preparation of Example 6 but starting from (E)-4-formylcinnamic acid gave after recrystallization from acetone:MeOH (10:3), the title compound as yellow crystals in a 60% yield. MP: 146° C.

Analysis for C$_{27}$H$_{22}$N$_2$O$_2$.0.4H$_2$O: Calculated: C, 78.39; H, 5.55; N, 6.77. Found: C, 78.33; H, 5.54; N, 6.67%.

EXAMPLE 10

(E)-N-[4-[3-Oxo-3-(1-(4-nitrophenyl)-1,3,4,9-tetrahydro-β-carbolin-2-yl)propenyl]phenyl]acetamide The same method as employed in the preparation of Example 6 but starting from Intermediate 3 gave after recrystallization from 2-propanol, the title compound as white crystals in a 51% yield. MP: 185° C.

Analysis for C$_{28}$H$_{24}$N$_4$O$_4$. 0.6H$_2$O: Calculated: C, 68.45; H, 5.17; N, 11.4. Found: C, 68.37; H, 5.06; N, 11.26%.

EXAMPLE 11

(E)-1-[1-(4-Nitrophenyl)-1,3,4,9-tetrahydro-β-carbolin-2-yl]-3-phenylpropene-1-one The same method as employed in the preparation of Example 1 but starting from Intermediate 3 gave after recrystallization from 2-propanol, the title compound as a yellow powder in a 15% yield. MP: 205–206° C.

Analysis for C$_{26}$H$_{21}$N$_3$O$_3$. 0.2H$_2$O: Calculated: C, 73.12; H, 5.05; N, 9.84. Found: C, 72.95; H, 5.15; N, 9.81%.

EXAMPLE 12

(E)-1-[1-(4-Trifluoromethoxyphenyl)-1,3,4,9-tetrahydro-β-carbolin-2-yl]-3-phenyl-propene-1-one The same method as employed in the preparation of Example 1 but starting from Intermediate 4 gave after recrystallization from pentane, the title compound as white crystals in a 44% yield. MP: 119° C.

Analysis for C$_{27}$H$_{21}$N2O$_2$F$_3$: Calculated: C, 70.12; H, 4.58; N, 6.06. Found: C, 70.02; H, 4.58; N, 6.02%.

EXAMPLE 13

(E)-1-[1-(4-Methylphenyl)-1,3,4,9-tetrahydro-β-carbolin-2-yl]-3-phenylpropene-1-one The same method as employed in the preparation of Example 1 but starting from Intermediate 6 gave after recrystallization from pentane, the title compound as white crystals in a 50% yield. MP: 125–127° C.

Analysis for C$_{27}$H$_{24}$N$_2$O. 0.6H$_2$O: Calculated: C, 80.41; H, 6.3; N, 6.95. Found: C, 80.49 ; H, 6.2 ; N, 7.25%.

EXAMPLE 14

(E)-N-[4-[3-Oxo-3-(1-(3,4-methylenedioxyphenyl)-1,3,4,9-tetrahydro-β-carbolin-2-yl)propenyl]phenyl]acetamide The same method as employed in the preparation of Example 6 but starting from Intermediate 7 and (E)-3-(4-acetyl-aminophenyl)acrylic acid gave after recrystallization from 2-propanol:pentane, the title compound as white crystals in a 85% yield. MP: 185° C.

Analysis for C$_{29}$H$_{25}$N$_3$O$_4$. 0.4H$_2$O: Calculated: C, 71.56; H, 5.34; N, 8.63. Found: C, 71.59; H, 5.32; 8.66%.

EXAMPLE 15

(E)-4-[3-Oxo-3-(1-phenyl-1,3,4,9-tetrahydro-β-carbolin-2-yl)propenyl]benzoic acid, methyl ester To a solution of Example 9 (0.2 g, 0.49 mmol) in 20 mL of MeOH was added activated MnO$_2$ (0.59 g, 14 equiv.), sodium cyanide (0.05 g, 2 equiv.) and acetic acid (0.05 g, 1.7 equiv.). The resulting mixture was stirred for 5 hours. Tlc monitoring showed a new compound (SiO$_2$, DCM:MeOH (95:5), Rf=0.82). The mixture was filtered through a short column of celite using 150 mL of a mixture of MeOH:EtOAc:CHCl$_3$ (1:25:25). After evaporation in vacuo the residue was purified via flash chromatography on a 2×20 cm$^2$ column using DCM as eluting solvent. Evaporation and recrystallization from EtOH gave the title compound (0.15 g, 70%) as yellow crystals. MP: 222° C.

Analysis for C$_{28}$H$_{24}$N$_2$O$_3$. 0.03H$_2$O: Calculated: C, 76.1; H, 5.61; N, 6.34. Found: C, 76.05; H, 5.68; N, 6.15%.

EXAMPLE 16

(E)-1-[1-(2-Chlorophenyl)-1,3,4, 9-tetrahydro-β-carbolin-2-yl]-3-phenylpropene-1-one The same method as employed in the preparation of Example 1 but starting from Intermediate 17 gave after recrystallization from EtOH, the title compound as white crystals in a 27% yield. MP: 220–221° C.

Analysis for $C_{26}H_{21}N_2OCl$: Calculated: C, 75.63; H, 5.13; N, 6.78. Found: C, 75.4; H, 5.21; N, 6.79%.

EXAMPLE 17

(E)-1-(1-Phenyl-1 3,4, 9-tetrahydro-β-carbolin-2-yl)-3-(3,4-methylenedioxyphenyl)-propene-1-one The same method as employed in the preparation of Example 1 but starting from (E)-(3,4-methylenedioxy)cinnamoyl chloride gave after recrystallization from EtOH, the title compound as a white powder in a 65% yield. MP: 221° C.

Analysis for $C_{27}H_{22}N_2O_3 \cdot 0.3H_2O$: Calculated: C, 75.79; H, 5.32; N, 6.55. Found: C, 75.76; H, 5.37; N, 6.53%.

EXAMPLE 18

(E)-1-[1-(3,4-Methylenedioxyphenyl)-1,3,4,9-tetrahydro-β-carbolin-2-yl]-3-(4-bromophenyl)propene-1-one The same method as employed in the preparation of Example 1 but starting from Intermediate 7 and (E)-4-bromocinnamoyl chloride gave after recrystallization from EtOH, the title compound as a white powder in a 10% yield. MP: 188–190° C.

Analysis for $C_{27}H_{21}N_2O_3Br \cdot 0.3H_2O$: Calculated: C, 63.99; H, 4.3; N, 5.53. Found: C, 63.53; H, 4.23; N, 5.38%.

EXAMPLE 19

(E)-1-[1-(4-Chlorophenyl)-1,3,4,9-tetrahydro-β-carbolin-2-yl]-3-phenylpropene-1-one The same method as employed in the preparation of Example 1 but starting from Intermediate 5 gave after recrystallization from EtOH, the title compound as white crystals in a 72% yield. MP: 213–214° C.

Analysis for $C_{26}H_{21}N_2OCl$: Calculated: C, 75.63; H, 5.13; N, 6.78. Found: C, 75.55; H, 5.16; N, 6.63%

EXAMPLE 20

(E)-1-[1-(3,4-Methylenedioxyphenyl)-1,3,4,9-tetrahydro-β-carbolin-2-yl]-3-(4-ethoxyphenyl)propene-1-one To a solution of Intermediate 7 (0.2 g, 0.68 mmol) in 40 mL of DCM were added $Et_3N$ (0.1 mL, 1.1 equiv.), EDCl (0.14 g, 1.1 equiv.), HOBT (0.12 g, 1.1 equiv.) and (E)-4-ethoxycinnamic acid (0.14 g, 1.1 equiv.). After 48 hours of stirring at rt the reaction was judged to be completed by tlc monitoring ($SiO_2$, DCM:MeOH (95:5)) and was quenched with 50 mL of water. The reaction mixture was extracted with DCM, washed with brine (5 mL), dried over $MgSO_4$ and concentrated in vacuo. Flash chromatography on a 2.5×25 cm² column of silica gel using DCM:MeOH (98:2) as eluting solvent and removal of the solvent in vacuo gave the title compound (0.21 g, 67%) as white crystals after recrystallization from EtOH. MP: 199–200° C.

Analysis for $C_{29}H_{26}N_2O_4 \cdot 0.3H_2O$: Calculated: C, 73.8; H, 5.68; N, 5.94. Found: C, 73.72; H, 5.68; N, 5.97%.

EXAMPLE 21

(E)-4-[3-Oxo-3-(1-(3,4-methylenedioxyphenyl)-1,3,4,9-tetrahydro-β-carbolin-2-yl)propenyl]acetic Acid, Phenyl Ester The same method as employed in the preparation of Example 20 but starting from (E)-4-acetoxycinnamic acid gave after recrystallization from MeOH, the title compound as white crystals in a 54% yield. MP: 216° C.

Analysis for $C_{29}H_{24}N_2O_5$: Calculated: C, 72.49; H, 5.03; N, 5.83. Found: C, 72.3; H, 5.11; N, 5.84%.

EXAMPLE 22

(E)-1-[1-(3,4-Methylenedioxyphenyl)-1,3,4,9-tetrahydro-β-carbolin-2-yl]-3-(4-hydroxyphenyl)propene-1-one The same method as employed in the preparation of Example 20 but starting from (E)-4-hydroxycinnamic acid gave after recrystallization from EtOH:pentane the title compound as white crystals in a 57% yield. MP: 175° C.

Analysis for $C_{27}H_{22}N_2O_4 \cdot 0.3H_2O$: Calculated: C, 73.06; H, 5.13; N, 6.31. Found: C, 73.14; H, 5.36; N, 6.44%.

EXAMPLE 23

(E)-1-[1-(3,4-Methylenedioxyphenyl)-1,3,4,9-tetrahydro-β-carbolin-2-yl]-3-(4-formylphenyl)propene-1-one The same method as employed in the preparation of Example 20 but starting from (E)-4-formylcinnamic acid gave after recrystallization from MeOH the title compound as white crystals in a 100% yield. MP: 208° C.

Analysis for $C_{28}H_{22}N_2O_4 \cdot 0.3H_2O$: Calculated: C, 73.77; H, 5.00; N, 6.15. Found: C, 73.77; H, 4.96; N, 6.05%.

EXAMPLE 24

(E)-1-[4-[3-Oxo-3-(1-(3,4-methylenedioxyphenyl)-1,3,4,9-tetrahydro-β-carbolin-2-yl)-propenyl]phenyl]-3-phenylurea The same method as employed in the preparation of Example 20 but starting from (E)-3-[4-(3-(phenylureido)phenyl]acrylic acid (which was prepared in situ by reaction of phenylisocyanate (1 equiv.), (E)-4-aminocinnamic acid (1 equiv.) and $Et_3N$ (1 equiv.)), gave after recrystallization from EtOH the title compound as white crystals in a 61% yield. MP: 192° C.

Analysis for $C_{34}H_{28}N_4O_4 \cdot 0.22(EtOH:H_2O)$: Calculated: C, 72.48; H, 5.26; N, 9.82. Found: C, 72.87; H, 5.17; N, 9.42%.

EXAMPLE 25

(E)-1-[1-(3,4-Methylenedioxyphenyl)-1,3,4,9-tetrahydro-β-carbolin-2-yl]-3-(4-aminophenyl)propene-1-one The same method as employed in the preparation of Example 20 but starting from (E)-4-aminocinnamic acid gave after recrystallization from EtOH:DCM:2-propanol (10:2:2) the title compound as white crystals in a 63% yield. MP: 262–265° C.

Analysis for $C_{27}H_{23}N_3O_3 \cdot 0.3H_2O$: Calculated: C, 73.22; H, 5.37; N, 9.49. Found: C, 72.9; H, 5.47; 9.32%.

EXAMPLE 26

(E)-1-[1-(3,4-Methylenedioxyphenyl)-1,3,4,9-tetrahydro-β-carbolin-2-yl]-3-(4-nitrophenyl)propene-1-one The same method as employed in the preparation of Example 20 but starting from (E)-4-nitrocinnamic acid gave after recrystallization from EtOH, the title compound as yellow crystals in a 69% yield. MP: 158° C.

Analysis for $C_{27}H_{21}N_3O_5$: Calculated: C, 69.37; H, 4.53; N, 8.99. Found: C, 69.57; H, 4.61; N, 8.92%.

EXAMPLE 27

(E)-1-[1-(3,4-Methylenedioxyphenyl)-1,3,4,9-tetrahydro-β-carbolin-2-yl]-3-[(4-bis(methylsulfonyl)aminophenyl]propene-1-one This product was prepared by refluxing for two hours a solution of Example 25 (0.2 g, 0.6 mmol), mesyl chloride (0.1 mL, 5 equiv.), $Et_3N$ (0.4 mL, 5 equiv.) in 20 mL of THF. The disappearance of the starting material and the formation of a new compound were confirmed by tlc ($SiO_2$, DCM:MeOH (95:5), Rf=0.84). After evaporation of THF the residue was dissolved in DCM (15 mL) and washed with $H_2O$ (10 mL). The organic solution was dried over $MgSO_4$ and concentrated in vacuo to give a residue which was purified via flash chromatography on a 2.5×25 $cm^2$ column using DCM:MeOH (98:2) as eluting solvent. Recrystallization from EtOH gave the title compound (0.09 g, 25%) as a white powder. MP: 276° C.

Analysis for $C_{29}H_{27}N_3O_7S_2$. $0.3H_2O$: Calculated: C, 58.14; H, 4.64; N, 7.01. Found: C, 57.76; H, 4.69; N, 6.81%.

EXAMPLE 28

(E)-4-[3-Oxo-3-[1-(3,4-methylenedioxyphenyl)-1,3,4,9-tetrahydro-β-carbolin-2-yl]-propenyl]benzoic Acid, Methyl Ester The same method as employed in the preparation of Example 20 but starting from (E)-4-(2-carboxyvinyl)benzoic acid, methyl ester acid (prepared according to the procedure of Taylor et al., *Heterocycles* 1993, 36, 1897–1908), gave after recrystallization from MeOH:$H_2O$ (99:1), the title compound as yellow crystals in a 84% yield. MP: 211° C.

Analysis for $C_{29}H_{24}N_2O_5$. $0.3H_2O$: Calculated: C, 71.68; H, 5.1; N, 5.76. Found: C, 71.76; H, 5.02; N, 5.68%.

EXAMPLE 29

(E)-N-[4-[3-Oxo-3-[1-(3,4-methylenedioxyphenyl)-1,3,4,9-tetrahydro-β-carbolin-2-yl]propenyl]phenyl] methanesulfonamide The same method as employed in the preparation of Example 27 but using 1 equiv. of mesyl chloride gave after recrystallization from EtOH the title compound as an off-white powder in a 10% yield. MP: 203° C.

Analysis for $C_{28}H_{25}N_3O_5S$. $0.2H_2O$: Calculated: C, 64.78; H, 4.93; N, 8.09. Found: C, 64.66; H, 5.15; N, 7.73%.

EXAMPLE 30

(E)-4-[3-Oxo-3-[1-(3,4-methylenedioxyphenyl)-1,3,4,9-tetrahydro-β-carbolin-2-yl]propenyl]benzamide Into a solution of Example 28 (0.2 g, 0.4 mmol) in 50 mL of MeOH was bubbled ammonia and the resulting mixture was stirred at 35° C. for two days. The mixture was concentrated in vacuo to give a residue which was washed with 2×30 mL of water. Extraction, drying over $MgSO_4$ and concentration in vacuo gave a residue that was purified via radial chromatography using DCM:MeOH (90:10) as eluting solvent and via preparative chromatography (20×20- cm plate, 0.5 mm, $SiO_2$) using the same eluant. The title compound (0.025 g, 13%) was isolated as white crystals after recrystallization from MeOH:$H_2O$. MP: 183° C.

Analysis for $C_{28}H_{23}N_3O_4$: Calculated: C, 70.07; H, 5.17; N, 8.76. Found: C, 69.97; H, 5.16; N, 8.84%.

EXAMPLE 31

(E)-4-[3-Oxo-3-[1-(3,4-methylenedioxyphenyl)-1,3,4 9-tetrahydro-β-carbolin-2-yl]-propenyl]benzoic Acid This product was prepared by refluxing for four hours a stirred solution of Example 28 (0.5 g, 1.04 mmol) and NaOH (1N) (5.2 mL, 5 equiv.) in 50 mL of MeOH. After evaporation of the solvent in vacuo, the residue was treated with 10 mL of HCl (1N). A solid precipitated out and was filtered off. Recrystallization from MeOH gave the title compound (0.35 g, 72%) as white crystals. MP: 254–256° C.

Analysis for $C_{28}H_{22}N_2O_5$. $0.2H_2O$: Calculated: C, 72.09; H, 4.75; N, 6.01. Found: C, 71.60; H, 4.84; N, 5.88%.

EXAMPLE 32

(E)-1-[1-(3,4-Methylenedioxyphenyl)-1,3,4,9-tetrahydro-β-carbolin-2-yl]-3-(4-cyanophenyl)propene-1-one The same method as employed in the preparation of Example 20 but starting from (E)-4-cyanocinnamic acid gave after recrystallization from EtOH the title compound as white crystals in a 69% yield. MP: 167° C.

Analysis for $C_{28}H_{21}N_3O_3$. $0.1H_2O$: Calculated: C, 74.85; H, 4.76; N, 9.35. Found: C, 74.72; H, 4.81; N, 9.27%.

EXAMPLE 33

(E)-1-[1-(3,4-Methylenedioxyphenyl)-1,3,4,9-tetrahydro-β-carbolin-2-yl]-3-(4-trifluoromethylphenyl)propene-1-one The same method as employed in the preparation of Example 20 but starting from (E)-4-trifluoromethylcinnamic acid gave after recrystallization from EtOH the title compound as white crystals in a 73% yield. MP: 233° C.

Analysis for $C_{28}H_{21}F_3N_2O_3$. $0.2H_2O$: Calculated: C, 68.07; H, 4.37; N, 5.67. Found: C, 68.04; H, 4.32; N, 5.65%.

EXAMPLE 34

(E)-1-[1-(3,4-Methylenedioxyphenyl)-1,3,4,9-tetrahydro-β-carbolin-2-yl]-3-(3,4-methylenedioxyphenyl)propene-1-one The same method as employed in the preparation of Example 20 but starting from (E)-3,4-methylenedioxycinnamic acid gave after recrystallization from EtOH the title compound as yellow crystals in a 73% yield. MP: 233° C.

Analysis for $C_{28}H_{22}N_2O_5$: Calculated: C,72.09; H,4.75; N,6.01; Found: C,71.79; H,4.76; N,5.93%.

EXAMPLE 35

(E)-1-[1-(3,4-Methylenedioxyphenyl)-1,3,4,9-tetrahydro-β-carbolin-2-yl]-3-(4-chlorophenyl)propene-1-one The same method as employed in the preparation of Example 20 but starting from (E)-4-chlorocinnamic acid gave after recrystallization from EtOH the title compound as white crystals in a 55% yield.

MP: 203° C. Analysis for $C_{27}H_{21}N_2O_3Cl$: Calculated: C,70.97; H,4.63; N,6.13; Found: C,71.04; H,4.76; N,6.04%.

EXAMPLE 36

(E)-1-[1-(3,4-Methylenedioxyphenyl)-1,3,4,9-tetrahydro-β-carbolin-2-yl]-3-(4-trifluoromethoxyphenyl)propene-1-one The same method as employed in the preparation of Example 20 but starting from (E)-4-trifluoromethoxycinnamic acid (prepared according to the procedure of Yagupol'skii et al, *Zhurnal Obshchei Khimii* 1960, 30, 3102–3104) gave after recrystallization from EtOH the title compound as yellow crystals in a 35% yield. MP: 203–205° C.

Analysis for $C_{28}H_{21}F_3N_2O_4$: Calculated: C,66.4; H,4.18; N,5.53; Found: C,66.23; H,4.26; N,5.54.

EXAMPLE 37

(E)-1-[1-(3,4-Methylenedioxyphenyl)-1,3,4,9-tetrahydro-β-carbolin-2-yl]-3-(4-methylphenyl)propene-1-one The same method as employed in the preparation of Example 20 but starting from (E)-4-methylcinnamic acid gave after recrystallization from EtOH:DCM (99:1) the title compound as white crystals in a 67% yield. MP: 240° C.

Analysis for $C_{28}H_{24}N_2O_3 \cdot 0.7H_2O$: Calculated: C,74.88; H,5.7; N,6.24; Found: C,74.83; H,5.45; N,6.35.%.

EXAMPLE 38

(E)-[4-[3-Oxo-3-(1-(3,4-methylenedioxyphenyl)-1,3,4,9-tetrahydro-β-carbolin-2-yl)propenyl]-phenyl]urea The same method as employed in the preparation of Example 20 but starting from Intermediate 22 gave after recrystallization from EtOH the title compound as white crystals in a 49% yield. MP: 208° C.

Analysis for $C_{28}H_{24}N_4O_4 \cdot 0.5H_2O$: Calculated: C,68.7; H,5.15; N,11.44; Found: C,68.51; H,5.14; N,11.35%.

EXAMPLE 39

(E)-1-[1-(3,4-Methylenedioxyphenyl)-1,3,4,9-tetrahydro-β-carbolin-2-yl]-3-(4-hydroxymethylphenyl)-propene-1-one This product was prepared by stirring a solution of Example 23 (0.3 g, 0.66 mmol) in 40 mL of MeOH with $NaBH_4$ (0.1 g, 4 equiv.) at rt for two hours. Evaporation of the solvent gave a residue which was dissolved in DCM (100 mL) and washed twice with water (50 mL). Extraction with DCM, drying over $MgSO_4$ and evaporation in vacuo gave the title compound (0.2 g, 67%) as white crystals after recrystallization from EtOH. MP: 206° C.

Analysis for $C_{28}H_{24}N_2O_4 \cdot 0.3EtOH$: Calculated: C,73.66; H,5.58; N,6.01; Found: C,73.69; H,5.5; N,6.06%.

EXAMPLE 40

(E)-N-Benzyl-4-[3-oxo-3-(1-(3,4-methylenedioxyphenyl)-1,3,4,9-tetrahydro-β-carbolin-2-yl)-propenyl]benzamide This product was prepared by stirring a solution of Example 31 (0.2 g, 0.43 mmol) in 50 mL of THF with benzylamine (0.5 mL, 9 equiv.), $Et_3N$ (1 mL) and diphenylphosphoryl azide (0.5 mL). After two days the reaction mixture was concentrated in vacuo. The residue was taken up in 100 mL of DCM and washed with 3×50 mL of water. Drying over $Na_2SO_4$ and evaporation of the solvent gave a residue which was purified via flash chromatography with cyclohexane and $Et_2O$. Evaporation in vacuo and recrystallization from EtOH gave the title compound (0.03 g, 13%) as white crystals. MP: 203° C.

Analysis for $C_{35}H_{29}N_3O_4$; Calculated: C,75.66; H,5.26; N,7.56; Found: C,75.5; H,5.22; N,7.55%.

EXAMPLE 41

(E)-1-[1-(3,4-Methylenedioxyphenyl)-1,3,4,9-tetrahydro-3-carbolin-β-yl]-3-(2,4-dichlorophenyl)-propene-1-one The same method as employed in the preparation of Example 20 but starting from (E)-2,4-dichlorocinnamic acid gave after recrystallization from EtOH:$H_2O$ the title compound as a white powder in a 66% yield. MP: 194° C.

Analysis for $C_{27}H_{20}N_2O_3Cl_2$: Calculated: C,66.00; H,4.10; N,5.70; Found: C,65.85; H,4.13; N,5.78%.

EXAMPLE 42

(E)-1-[1-(3,4-Methylenedioxyphenyl)-1,3,4,9-tetrahydro-β-carbolin-2-yl]-3-(3-methoxy-4-hydroxyphenyl)propene-1-one The same method as employed in the preparation of Example 20 but starting from (E)-3-methoxy-4-hydroxycinnamic acid gave after recrystallization from EtOH:$H_2O$ (10:1) the title compound as an off-white powder in a 62% yield.

MP: 155° C. Analysis for $C_{28}H_{24}N_{24}O_5$: Calculated: C,71.78; H,5.16; N,5.98; Found: C,71.44; H,5.16; N,5.76%.

EXAMPLE 43

(E)-1-[1-(3,4-Methylenedioxyphenyl)-1,3,4,9-tetrahydro-β-carbolin-2-yl]-3-(3-hydroxy-4-methoxyphenyl)propene-1-one The same method as employed in the preparation of Example 20 but starting from (E)-3-hydroxy-4-methoxycinnamic acid gave after recrystallization from EtOH:$H_2O$ the title compound as an off-white powder in a 47% yield. MP: 213° C.

Analysis for $C_{28}H_{24}N_2O_5 \cdot 0.3H_2O$: Calculated: C,70.96; H,5.23; N,5.91; Found: C,71.09; H,5.60; N,5.66%.

EXAMPLE 44

(E)-1-[1-(3,4-Methylenedioxyphenyl)-1,3,4,9-tetrahydro-β-carbolin-2-yl]-3-(4-fluorophenyl) propene-1-one The same method as employed in the preparation of Example 20 but starting from (E)-4-fluorocinnamic acid gave after recrystallization from EtOH the title compound as white crystals in a 74% yield.

MP: 138–139° C. Analysis for $C_{27}H_{21}F_3N_2O_3$: Calculated: C,73.62; H,4.81; N,6.36; Found: C,73.78; H,4.81; N,5.97%.

EXAMPLE 45

(E)-1-[1-(3,4-Methylenedioxyphenyl)-1,3,4,9-tetrahydro-β-carbolin-2-yl]-3-indan-5-yl-1-propene-1-one The same method as employed in the preparation of Example 20 but starting from (E)-3-indane-5-yl-acrylic acid gave, after precipitation, the title compound as a yellow powder in a 22% yield. MP: 115° C.

Analysis for $C_{20}H_{26}N_2O_3 \cdot 0.6H_2O$: Calculated: C,76.12; H,5.79; N,5.92; Found: C,76.13; H,5.79; N,5.72%.

EXAMPLE 46

(E)-N-[4-[3-Oxo-3-(1-(3,4-methylenedioxyphenyl)-1,3,4,9-tetrahydro-β-carbolin-2-yl)propenyl]-benzoyl]benzenesulfonamide The same method as employed in the preparation of Example 20 but starting from Example 31 and benzenesulfonamide gave after recrystallization from EtOH:H$_2$O the title compound as white crytals in a 20% yield. MP: 134° C.

Analysis for $C_{20}H_{26}N_2O_3 \cdot 0.6H_2O$: Calculated: C,56.13; H,6.67; N,10.91; Found: C,55.97; H,6.75; N,10.82%.

EXAMPLE 47

(E)-1-[1-(3,4-Methylenedioxyohenyl)-1,3,4,9-tetrahydro-β-carbolin-2-yl]-3-(3,4-dichlorophenyl)-propene-1-one The same method as employed in the preparation of Example 20 but starting from (E)-3,4-dichlorocinnamic acid gave after recrystallization from EtOH:H$_2$O (99:1) the title compound as a white powder in a 45% yield. MP: 212° C.

Analysis for $C_{27}H_{20}Cl_2N_2O_3$: Calculated: C,66.00; H,4.10; N,5.70; Found: C,65.68; H,4.12; N, 5.68%.

EXAMPLE 48

(E)-1-[1-(3,4-Methylenedioxyphenyl)-1,3,4,9-tetrahydro-β-carbolin-2-yl]-3-(3,4-dimethoxyphenyl)-propene-1-one The same method as employed in the preparation of Example 20 but starting from (E)-3,4-dimethoxycinnamic acid gave after recrystallization from EtOH:DCM the title compound as a white powder in a 61% yield. MP: 233° C.

Analysis for $C_{29}H_{26}N_2O_5 \cdot 0.5\ H_2O$: Calculated: C,70.86; H,5.54; N,5.70; Found: C,70.66; H,5.44; N,5.70%.

EXAMPLE 49

(E)-1-[1-(3,4-Methylenedioxyphenyl)-1,3,4,9-tetrahydro-3-carbolin-2-yl]-3-(3,4-dihydroxyphenyl)-propene-1-one The same method as employed in the preparation of Example 20 but starting from (E)-3,4-dihydroxycinnamic acid gave after recrystallization from EtOH:DMF the title compound as a white powder in a 41% yield. MP: 163–165° C.

Analysis for $C_{27}H_{22}N_2O_5 \cdot 0.3DMF$: Calculated: C,70.34; H,5.10; N,6.76; Found: C,70.38; H,5.13; N,6.66%.

EXAMPLE 50

(E)-N-Methyl-N-[4-(3-oxo-3-(1-(3,4-methylenedioxyphenyl)-13,4,9-tetrahydro-β-carbolin-2-yl)-propenyl)phenyl]acetamide The same method as employed in the preparation of Example 20 but starting from Intermediate 23 gave after recrystallization from EtOH:H$_2$O (10:0.6) the title compound as an off-white powder in a 86% yield EtOH:H$_2$O. MP: 165° C.

Analysis for $C_{30}H_{27}N_3O_4 \cdot 0.4H_2O$: Calculated: C,71.96; H,5.6; N,8.39; Found: C,71.8; H,5.57; N,8.28%.

EXAMPLE 51

(E)-2,2-Dimethyl-N-[4-[3-Oxo-3-(1-(3,4-methylenedioxyphenyl)-1,3,4,9-tetrahydro-β-carbolin-2-yl)-propenyl]propionamide This product was prepared by condensation of Example 25 (0.2 g, 0.46 mmol) with 2,2-dimethylpropionyl chloride (0.09 mL, 1.5 equiv.) and NaOH (1N) (0.7 mL, 1.5 equiv.) in a mixture of EtOAc:DCM (6:1). When starting material had disappeared, 40 mL of a mixture of DCM:H$_2$O (2:1) was added. Extraction with DCM, washing with a saturated aqueous solution of NH$_4$Cl and brine, drying over MgSO$_4$ and evaporation of the solvent in vacuo gave the title compound (0.2 g, 83%) after recrystallization from EtOH:H$_2$O (1:1).

MP: 172–174° C. Analysis for $C_{32}H_{31}N_3O_4 \cdot 0.1H_2O$: Calculated: C,71.23; H,6.16; N,7.79; Found: C,70.99; H,6.02 ; N,7.84%.

EXAMPLE 52

(E)-1-[1-(3,4-Methylenedioxyphenyl)-1,3,4,9-tetrahydro-3-carbolin-2-yl]-3-(3,5-dimethoxyphenyl)-propene-1-one The same method as employed in the preparation of Example 20 but starting from (E)-3,5-dimethoxycinnamic acid gave after recrystallization from EtOH the title compound as a white powder in a 61% yield.

MP: 178° C. Analysis for $C_{29}H_{26}N_2O_5$: Calculated: C,72.19; H,5.43; N,5.81; Found: C,72.3; H,5.48; N,5.63%.

EXAMPLE 53

(E)-(N)-f4-[3-[1-(3,4-Methylenedioxyphenyl)-6-fluoro-1,3,4,9-tetrahydro-3-carbolin-2-yl]-3-oxoprolpenyl]-phenyl]-acetamide The same method as employed in the preparation of Example 20 but starting from Intermediate 16 and and (E)-3-(4-acetylaminophenyl)acrylic acid gave after recrystallization from MeOH the title compound as a white crystals in a 72% yield. MP: 179–181° C.

Analysis for $C_{29}H_{24}N_3O_4F \cdot 0.4H_2O$: Calculated: C,69.01; H,4.95; N,8.33; Found: C,68.97; H,4.91; N,8.34%.

EXAMPLE 54

(E)-1-[1-(3 4-Methylenedioxyphenyl)-1,3,4,9-tetrahydro-β-carbolin-2-y11-3-(3,4, 5-trimethoxyphenyl)-propene-1-one The same method as employed in the preparation of Example 20 but starting from (E)-3,4,5-trimethoxycinnamic acid gave after recrystallization from MeOH the title compound as a white powder in a 49% yield.

MP: 211° C. Analysis for $C_{30}H_{28}N_2O_6$: Calculated: C,70.3 ; H,5.51; N,5.47; Found: C,70.49; H,5.59; N,5.34.%.

EXAMPLE 55

(E)-N-[4-[3-Oxo-3-(1-(3,4-methylenedioxyphenyl)-1,3,4,9-tetrahydro-β-carbolin-2-yl)Dropenyl]phenyl]-isobutyramide The same method as employed in the preparation of Example 51 but starting from isobutyryl chloride gave after recrystallization from EtOH the title compound as a white powder in a 85% yield. MP: 171° C.

Analysis for $C_{31}H_{29}N_3O_4 \cdot 0.4$ ($H_2O$:MeOH) Calculated: C,72.61; H,6.02; N,7.99; Found: C,72.33; H,5.77; N,8.33%.

EXAMPLE 56

(E)-1-[1-(3,4-Methylenedioxyphenyl)-6-fluoro-1,3,4, 9-tetrahydro-β-carbolin-2-yl]-3-phenylpropene-1-one The same method as employed in the preparation of Example 1 but starting from Intermediate 16 gave after recrystallization from EtOH the title compound as white crystals in a 71% yield. MP: 227–228° C.

Analysis for $C_{27}H_{21}N_2O_3F$: Calculated: C,73.63; H,4.81; N,6.36; Found: C,73.72; H,4.77; N,6.43%.

EXAMPLE 57

(E)-N-(2-Methoxyethyl)-4-[3-oxo-3-(1-(3,4-methylenedioxyphenyl)-1,3,4,9-tetrahydro-A-carbolin-2-yl)-propenyl]benzamide The same method as employed in the preparation of Example 20 but starting from Intermediate 24 gave after recrystallization from EtOH the title compound as white crystals in a 43% yield. MP: 170° C.

Analysis for $C_{27}H_{21}N_2O_3F \cdot 1.3H_2O$: Calculated: C,68.07; H,5.82; N,7.68; Found: C,67.98; H,5.8; N,7.7%.

EXAMPLE 58

(E)-1-[1-(3,4-Methylenedioxyphenyl)-1,3,4,9-tetrahydro-β-carbolin-2-yl]-3-(3-hydroxyphenyl) propene-1-one The same method as employed in the preparation of Example 20 but starting from (E)-3-hydroxycinnamic acid gave after recrystallization from EtOH:$H_2O$ the title compound as white crystals in a 54% yield.

MP: 248° C. Analysis for $C_{27}H_{22}N_2O_4$: Calculated: C,73.96; H,5.06; N,6.39; Found: C,74.04; H,5.1; N,6.37%.

EXAMPLE 59

(E)-1-[1-(3,4-Methylenedioxyphenyl)-1,3,4,9-tetrahydro-β-carbolin-2-yl]-3-(3-methoxyphenyl) propene-1-one The same method as employed in the preparation of Example 20 but starting from (E)-3-methoxycinnamic acid gave after recrystallization from EtOH the title compound as white crystals in a 49% yield.

MP: 218° C. Analysis for $C_{28}H_{24}N_2O_4$: Calculated: C,74.32; H,5.35; N,6.19; Found: C,74.37; H,5.61; N,6.32%.

EXAMPLE 60

(E)-1-1-(3,4-Methylenedioxyphenyl)-1,3,4,9-tetrahydro-β-carbolin-2-yl]-3-(3-nitrophenyl) propene-1-one The same method as employed in the preparation of Example 20 but starting from (E)-3-nitrocinnamic acid gave after recrystallization from EtOH:$H_2O$ (20:1) the title compound as white crystals in a 91% yield. MP: 156–158° C.

Analysis for $C_{28}H_{24}N_2O_4$: Calculated: C,69.37; H,4.54; N,8.99; Found: C,69.12; H,4.77; N,8.81%.

EXAMPLE 61

(E)-1-[1-(3,4-Methylenedioxyphenyl)-1,3,4,9-tetrahydro-3-carbolin-β-yl]-3-[4-(2-dimethylaminoethoxy)-phenyl]propene-1-one The same method as employed in the preparation of Example 20 but starting from Intermediate 25 gave after recrystallization from EtOH:$H_2O$ the title compound as white crystals in a 45% yield. MP: 157° C.

Analysis for $C_{31}H_{31}N_3O_4$: Calculated: C,73.07; H,6.13; N,8.25; Found: C,72.7; H,6.17; N,8.12%.

EXAMPLE 62

(E)-N-(2-Morpholin-4-ylethyl)-4-[3-oxo-3-(1-(3,4-methylenedioxyphenyl)-1,3,4,9-tetrahydro-β-carbolin-2-yl)propenyl]benzamide The same method as employed in the preparation of Example 20 but starting from Intermediate 26 gave after recrystallization from EtOH:$H_2O$ the title compound as white crystals in a 13% yield. MP: 145° C.

Analysis for $C_{34}H_{34}N_4O_5 \cdot 0.7H_2O$: Calculated: C,69.07; H,6.03; N9.48; Found: C,69.08; H, 6.03; N,9.45%.

EXAMPLE 63

(E)-1-[1-(3,4-Methylenedioxyphenyl)-1,3,4,9-tetrahydro-β-carbolin-2-yl]-3-[4-(1H-tetrazol-5-yl)-phenyl]1propene-1-one To a solution of Example 32 (0.25 g, 0.56 mmol) in 10 mL of toluene were added successively trimethylsilylazide (0.30 mL, 4 equiv.) and dibutyltinoxide (0.06 g, 0.4 equiv.). The resulting mixture was stirred at reflux for two days. Tlc monitoring showed formation of a new compound (DCM:MeOH (80:20), Rf=0.35). The reaction mixture was concentrated in vacuo. The resulting yellow gum was dissolved in MeOH and concentrated in vacuo. The residue was partitioned between EtOAc (25 mL) and an aqueous saturated solution of $NaHCO_3$ (25 mL). The organic phase was extracted with an additional portion of an aqueous saturated solution of $NaHCO_3$ (25 mL). The combined aqueous extracts were acidified to pH=2 with HCl (1N) and then extracted with EtOAc (2×25 mL). The combined organic extracts were dried over $MgSO_4$, filtered and concentrated to give a yellow powder that was purified via flash chromatography ($SiO_2$, DCM:MeOH (90:10)). Recrystallization from 2-propanol:$iPr_2O$ (1:1) gave the title compound (0.19 g, 70%) as white crystals. MP: 232–233° C.

Analysis for $C_2,H_{22}N_6O_3 \cdot 0.4H_2O$: Calculated: C,67.02; H,4.92; N,16.28; Found: C,66.83; H,4.53; N,15.96%.

EXAMPLE 64

(E)-1-[1-(3,4-Methylenedioxyphenyl)-1,3,4,9-tetrahydro-β-carbolin-2-yl]-3-(3-aminophenyl) propene-1-one A solution of Example 60 (1,36 g, 2.9 mmol), $SnCl_2 \cdot H_2O$ (2.8 g, 5 equiv.) in EtOH was refluxed overnight. After evaporation of the solvent, the residue was taken up in 50 mL of NaOH (1N). The aqueous phase was extracted with 2×100 mL of DCM and 2×50 mL of EtOAc. The combined organic layers were dried over $Na_2SO_4$ and concentrated in vacuo. Flash chromatography ($SiO_2$, DCM:MeOH (95:5) and recrystallization from EtOH:DCM gave the title compound (0.27 g, 21%) as a pale yellow powder. MP: 139–141° C.

Analysis for C$_{27}$H$_{23}$N$_3$O$_3$: Calculated: C,74.13; H,5.30; N,9.60; Found: C,73.93; H,5.35; N,9.43%.

EXAMPLE 65

(E)-N-Cyclohexyl-4-[3-oxo-3-(1-(3,4-methylenedioxyphenyl)-1,3,4,9-tetrahydro-β-carbolin-2-yl)-propenyl]benzamide The same method as employed in the preparation of Example 20 but starting from Intermediate 27 gave after recrystallization from EtOH:H$_2$O the title compound as white crystals in a 6% yield. MP: 214° C.

Analysis for C$_{28}$H$_{21}$N$_3$O$_3$.0.1H$_2$O: Calculated: C,72.19; H,6.24; N,7.43; Found: C,72.28; H,6.19; N,6.93%.

EXAMPLE 66

(E)-N-(Tetrahydrofuran-2-ylmethyl)-4-[3-oxo-3-(1-(3,4-methylenedioxyphenyl)-1,3,4,9-tetrahydro-β-carbolin-2-yl)propenyl]benzamide The same method as employed in the preparation of Example 20 but starting from Intermediate 28 gave after recrystallization from EtOH:H$_2$O (8:2) the title compound as white crystals in a 61% yield. MP: 168° C.

Analysis for C$_{32}$H$_{29}$N$_3$O$_5$.0.8H$_2$O: Calculated: C,69.88; H,5.61; N,7.64; Found: C,69.74; H,5.78; N,7.22%.

EXAMPLE 67

(E)-1-[1-(3,4-Methylenedioxyphenyl)-1,3,4,9-tetrahydro-β-carbolin-2-yl]-3-(3-cyanophenyl) propene-1-one The same method as employed in the preparation of Example 20 but starting from (E)-cyanocinnamic acid gave after recrystallization from EtOH:H$_2$O (8:2) the title compound as white crystals in a 46% yield.

MP: 228–230° C. Analysis for C$_{28}$H$_{21}$N$_3$O$_3$.0.8H$_2$O: Calculated: C,72.81; H,4.93; N,9.10; Found: C,72.74; H,4.69; N,8.99%.

EXAMPLE 68

(E)-N-(4-Piperidine-4-carboxylic acid, ethyl ester)-4-[3-oxo-3-(1-(3,4-methylenedioxyphenyl)-1,3,4,9-tetrahydro-β-carbolin-2-yl)propenyl]benzamide The same method as employed in the preparation of Example 20 but starting from Intermediate 29 gave after recrystallization from iPr$_2$O the title compound as white crystals in a 28% yield. MP: 144–145° C.

Analysis for C$_{36}$H$_{35}$N$_3$O$_6$.0.7H$_2$O: Calculated: C, 69.93; H,5.93; N,6.8; Found: C,69.84; H,5.83; N,6.81%.

EXAMPLE 69

(E)-N-(4-Piperidine-4-carboxylic acid)-4-[3-oxo-3-(1-(3,4-methylenedioxyphenyl)-1,3,4,9-tetrahydro-β-carbolin-2-yl)propenyl]benzamide This product was prepared by refluxing a solution of Example 68 (0.21 g, 0.36 mmol) with NaOH (1 N) (0.72 mL, 2 equiv.) in 20 mL of MeOH for 12 hours. After cooling the mixture was poured into H$_2$O (100 mL) and acidified with HCl (1 N). Extraction with 2×50 mL of DCM, drying over Na$_2$SO$_4$ and concentration in vacuo gave a residue which was recrystallized from MeOH:H$_2$O to give the title compound (0.05 g, 24%) as white crystals. MP: 204–205° C.

Analysis for C$_{34}$H$_{31}$N$_3$O$_6$.0.4H$_2$O: Calculated: C,68.56; H,5.58; N,7.05; Found: C,68.58; H,5.12; N,7.06%.

EXAMPLE 70

(E)-3-[3-Oxo-3-[1-(3,4-methylenedioxyphenyl)-1,3,4,9-tetrahydro-β-carbolin-2-yl]-propenyl] benzoic acid The same method as employed in the preparation of Example 20 but starting from (E)-3-(2-carboxyvinyl) benzoic acid gave after recrystallization from MeOH, the title compound as a white powder in a 21% yield. MP: 156–158° C.

Analysis for C$_{28}$H$_{22}$N$_2$O$_5$.0.8H$_2$O: Calculated: C,69.93; H,4.95; N,5.83; Found: C,69.94; H,4.62; N,5.65%.

EXAMPLE 71

(E)-1-[1-(3,4-Methylenedioxyphenyl)-1,3,4,9-tetrahydro-β-carbolin-2-yl]-3-(3-(4-methylpiperazine-1-carbonyl)rphenyl) propene-1-one The same method as employed in the preparation of Example 20 but starting from Example 70 and 4-methylpiperazine gave after recrystallization from MeOH:H$_2$O, the title compound as a white powder in a 30% yield. MP: 151° C.

Analysis for C$_{33}$H$_{32}$N$_4$O$_4$. H$_2$O: Calculated: C,69.95; H,6.05; N,9.89; Found: C,69.63; H,5.93; N,9.99%.

EXAMPLE 72

(E)-N-(2-Piperazin-1-ylethyl)-3-[3-oxo-3-(1-(3,4-methylenedioxyphenyl)-1,3,4,9-tetrahydro-β-carbolin-2-yl)propenyl]benzamide The same method as employed in the preparation of Example 20 but starting from Example 70 and 1-(2-aminoethyl)piperazine gave after recrystallization from iPr$_2$O, the title compound as a white powder in a 23% yield. MP: 138–140° C.

Analysis for C$_{34}$H$_{35}$N$_5$O$_4$.3.1H$_2$O: Calculated: C,64.46; H,6.55; N,11.05; Found: C,64.46; H,6.25; N,11.00%.

EXAMPLE 73

(E)-4-[3-Oxo-3-(1-(3,4-methylenedioxyphenyl)-1,3,4,9-tetrahydro-β-carbolin-2-yl)-propenyl]acetic acid ethyl ester The same method as employed in the preparation of Example 20 but starting from Intermediate 30 gave after recrystallization from DCM:pentane, the title compound as a white powder in a 17% yield. MP: 92–950° C.

Analysis for C$_{31}$H$_{28}$N$_2$O$_5$. 0.9H$_2$O: Calculated: C,70.95; H,5.72; N,5.34; Found: C,71,32; H,6.0; N,4.93%.

EXAMPLE 74

(E)-1-[1-(3,4-Methylenedioxyphenyl)-1,3,4,9-tetrahydro-β-carbolin-2-yl]-3-(3-tetrazolophenyl) propene-1-one The same method as employed in the preparation of Example 63 but starting from Example 67 gave after recrystallization from MeOH:H$_2$O, the title compound as a white powder in a 5% yield. MP: 260–2640C.

Analysis for C$_{28}$H$_{22}$N$_6$O$_3$.2.2H$_2$O: Calculated: C,63,43; H,5.02; N,15.85; Found: C,63.31; H,4.37; N,15.47%.

EXAMPLE 75

(E)-2-[3-Oxo-3-[1-(3,4-methylenedioxyphenyl)-1,3,
4,9-tetrahydro-β-carbolin-2-yl]-propenyl]-
benzoicacid, methyl ester The same method as employed in the preparation of Example 20 but starting from (E)-2-(2-carboxyvinyl) benzoic acid, methyl ester (prepared according to the procedure of Alabaster et al., *Synthesis* 1989, 8, 598–603), gave after recrystallization from MeOH, the title compound as white crystals in a 46% yield. MP: 203–204° C.

Analysis for $C_{27}H_{21}N_3O$; Calculated: C,72.49; H,5.03; N,5.83; Found: C,72.59; H,5.1; N,5.67%.

EXAMPLE 76

(E)-3-[3-Oxo-3-[1-(3,4-methylenedioxynhenyl)-1,3,
4 9-tetrahydro-β-carbolin-2-yl]-propenyl]benzoic
acid, methyl ester The same method as employed in the preparation of Example 20 but starting from (E)-3-(2-carboxyvinyl) benzoicacid, methyl ester (prepared according to the procedure of Baker et al., EP 134111 A1), gave after recrystallization from MeOH, the title compound as yellow crystals in a 61% yield. MP: 165–167° C.

Analysis for $C_{29}H_{24}N_2O_5$: Calculated: C,72.49; H,5.03; N,5.83; Found: C,72.53; H,5.02; N,5.93%.

EXAMPLE 77

(E)-1-(4-[3-Oxo-3-(1-(3,4-methylenedioxyphenyl)-1,
3,4,9-tetrahydro-β-carbolin-2-yl)-propenyl]-phenyl)
piperidine-4-carboxylic acid, ethyl ester The same method as employed in the preparation of Example 20 but starting from Intermediate 31 gave after recrystallization from MeOH, the title compound as yellow crystals in a 45% yield. MP: 175° C.

Analysis for $C_3,H_3,N_3O_5$: Calculated: C,72.77; H,6.11; N,7.27; Found: C,72.99; H,6.16; N,7.03%.

EXAMPLE 78

(E)-N-(1-Ethylpyrrolidin-2-yl-methyl)-3-[3-oxo-3-
(1-(3,4-methylenedioxyphenyl)-1,3,4,9-tetrahydro-β-
carbolin-2-yl propenyl]benzamide The same method as employed in the preparation of Example 20 but starting from Example 70 and 2-pyrrolidin-1-ylethylamine gave after recrystallization from iPr$_2$O, the title compound as a white powder in a 53% yield. MP: 128–130° C.

Analysis for $C_{35}H_{36}N_4O_4$: Calculated: C,72.9; H,6.29; N,9.72; Found: C,72.9; H,6.42; N,10.01%.

EXAMPLE 79

(E)-1-[1-(3,4-Methylenedioxyohenyl)-1,3,4 9-
tetrahydro-β-carbolin-2-yl]-3-(3-(2-
dimethylaminoethoxy)-phenyl)rpropene-1-one To a solution of Example 58 (0.25 g, 0.57 mmol) in 50 mL of DMF was added $K_2CO_3$ (0.24 g, 3 equiv.) and an excess of dimethylaminodiethyl chloride (about 15 equiv.). The resulting mixture was heated at 60° C. for four hours until disappearance of the starting material (tlc monitoring, DCM:MeOH (90:10). A new compound was formed (Rf= 0.20). After evaporation of DMF, the residue was taken up in 150 mL of DCM, washed with 2×50 mL of water, dried over $Na_2SO_4$ and recrystallized from EtOH:H$_2$O.to give the title compound (0.06 g, 22%) as yellow crystals. MP: 76–78° C.

Analysis for $C_{31}H_{31}N_3O_4$. 0.6H$_2$O: Calculated: C,71.55; H,6.24; N,8.07; Found: C,71,34; H,6.45; N,7.8%.

EXAMPLE 80

(E)-1-[1-(3,4-Methylenedioxyphenyl)-1,3,4,9-
tetrahydro-β-carbolin-2-yl]-3-(3,5-diterbutyl-4-
hydroxyphenyl)propene-1-one The same method as employed in the preparation of Example 20 but starting from (E)-3,5-ditertbutyl-4-hydroxycinnamic acid gave after recrystallization from cyclohexane, the title compound as yellow crystals in a 45% yield. MP: 137° C.

EXAMPLE 81

(E)-3-[3-Oxo-3-[1-(4-methoxycarbonylphenyl)-1,3,
4,9-tetrahydro-β-carbolin-2-yl]propenyl]benzoic
acid, methyl ester The same method as employed in the preparation of Example 20 but starting from Intermediate 8 and (E)-3-(2-carboxyvinyl)benzoic acid, methyl ester (prepared according to the procedure of Baker et al., EP 134111 A1), gave after recrystallization from 2-propanol, the title compound as white crystals in a 70% yield. MP: 182° C.

Analysis for $C_{30}H_{26}N_2O_5$: Calculated: C,72.86; H,5.3; N,5.66; Found: C,72.49 ; H,5.31 ; N,5.68%.

EXAMPLE 82

(E)-2-[3-Oxo-3-[1-(3,4-methylenedioxyphenyl)-1,3,
4,9-tetrahydro-β-carbolin-2-yl]propenyl]benzoic
acid The same method as employed in the preparation of Example 31 but starting from Example 75 gave after recrystallization from MeOH the title compound as off-white crystals in a 78% yield. MP: 174° C.

Analysis for $C_{28}H_{22}N_2O_5$: Calculated: C,72.09; H,4.75; N,6.01; Found: C,72.53; H,4.72; N,5.76%.

EXAMPLE 83

(E)-(4-[3-Oxo-3-(1-(3,4-methylenedioxyphenyl)-1,3,
4,9-tetrahydro-β-carbolin-2-yl)propenyl]-phenoxy)
acetic acid, ethyl ester The same method as employed in the preparation of Example 79 but starting from Example 22 and bromoacetic acid, ethyl ester, gave after recrystallization from EtOH:2-propanol the title compound as yellow crystals in a 28% yield. MP: 99–98° C.

Analysis for $C_{31}H_{28}N_2O_6$.2.4H$_2$O: Calculated: C,65.57; H,5.82; N,4.93; Found: C,65.34; H,5.4; N,5.09%.

EXAMPLE 84

(E)-(4-[3-Oxo-3-(1-(3,4-methylenedioxyphenyl)-1,3,
4,9-tetrahydro-β-carbolin-2-yl)propenyl]-phenyl)
acetic acid The same method as employed in the preparation of Example 31 but starting from a solution of Example 73 in EtOH gave after recrystallization from iPr$_2$O:2-propanol the title compound as white crystals in a 51% yield. MP: 231° C.

EXAMPLE 85

(E)-(4-[3-Oxo-3-(1-(3,4-methylenedioxyphenyl)-1,3, 4,9-tetrahydro-β-carbolin-2-yl)propenyl]-phenoxy) acetic acid The same method as employed in the preparation of Example 31 but starting from Example 83 gave after recrystallization from iPr$_2$O:2-propanol the title compound as yellow crystals in a 45% yield. MP: 158–160° C.

Analysis for $C_{29}H_{24}N_2O_6.0.9H_2O$: Calculated: C,67.93; H,5.07; N,5.46; Found: C,68.0; H,4.86; N,5.21%.

EXAMPLE 86

(E)-1-[1-(3,4-Methylenedioxyphenyl)-1,3,4,9-tetrahydro-β-carbolin-2-yl]-3-(3-nitro-4-chlorophenyl)-propene-1-one The same method as employed in the preparation of Example 20 but starting from (E)-3-nitro-4-chlorocinnamic acid gave after recrystallization from EtOH the title compound as yellow crystals in a 56% yield. MP: 240° C.

Analysis for $C_{27}H_{20}N_3O_5Cl$: Calculated: C,64.61; H,4.02; N,8.37; Found: C,64.5; H,3.97; N,8.28%.

EXAMPLE 87

(E)-1-[1-(3,4-Methylenedioxyphenyl)-1,3,4,9-tetrahydro-β-carbolin-2-yl]-3-(5-nitro-2-chlorophenyl)-propene-1-one The same method as employed in the preparation of Example 20 but starting from (E)-5-nitro-2-chlorocinnamic acid gave after recrystallization from EtOH:H$_2$O the title compound as yellow crystals in a 44% yield. MP: 146° C.

Analysis for $C_{27}H_{20}N_3O_5Cl$. $0.1H_2O$: Calculated: C,64.38; H,4.04; N,8.34; Found: C,64.12; H,3.81; N,8.35%.

EXAMPLE 88

(E)-3-Chloro-4-[3-oxo-3-1-(3,4-methylenedioxyphenyl)-1,3,4,9-tetrahydro-β-carbolin-2-yl]propenylbenzoic acid, methyl ester The same method as employed in the preparation of Example 20 but starting from Intermediate 32 gave after recrystallization from EtOH the title compound as a white powder in a 57% yield. MP: 166° C.

Analysis for $C_{29}H_{23}N_2O_5Cl$. 0.15EtOH: Calculated: C,67.43; H,4.62; N,5.37; Found: C,67.09; H,4.56; N,5.51%.

EXAMPLE 89

(E)-(4-[3-Oxo-3-(1-(3,4-methylenedioxyphenyl)-1,3, 4,9-tetrahydro-β-carbolin-2-yl)propenyl]-benzyloxy) acetic acid The same method as employed in the preparation of Example 79 but starting from a solution of (E)-(4-[3-oxo-3-(1-(3,4-methylenedioxyphenyl)-1,3,4,9-tetrahydro-β-carbolin-2-yl)propenyl]benzyloxy)acetic acid, ethyl ester in EtOH gave after recrystallization from MeOH:H$_2$O the title compound as an off-white solid in a 40% yield. MP: 162–163° C.

Analysis for $C_{30}H_{26}N_2O_6.0.1H_2O$: Calculated: C,68.17; H,5.13; N,5.49; Found: C,68.16; H,5.46; N,5.51%.

(E)-(4-[3-Oxo-3-(1-(3,4-methylenedioxyphenyl)-1,3, 4,9-tetrahydro-β-carbolin-2-yl)propenyl]-benzyloxy) acetic acid, ethyl ester To a solution of Example 39 (0.7 g, 1.5 mmol) in 50 mL of DMF was added K$_2$CO$_3$ (0.25 g, 1.2 equiv.) and ethyl-bromoacetate (0.2 mL, 1.1 equiv.). The resulting mixture was heated at 60° C. for 16 hours until disappearance of the starting material (tlc monitoring, DCM:MeOH (95:5)). A new compound was formed (Rf=0.8). After evaporation of DMF, the residue was taken up in 150 mL of DCM, washed with 2×50 mL of water, dried over Na$_2$SO$_4$ and purified via radial chromatography with DCM to give the title compound (0.85 g, 11%) as a white powder.

$^1$H NMR (CDCl$_3$) δ7.8–6.65 (m, 14H), 5.9 (s, 2H), 4.7 (s, 2H), 4.6–4.3 (q, 2H), 4.2–4.0 (m, 4H), 3.6–3.5 (m, 1H), 3.2–2.9 (m, 2H), 1,3–1.2 (t, 3H).

EXAMPLE 90

(E)-1-[1-(3,4-Methylenedioxyphenyl)-1,3,4,9-tetrahydro-β-carbolin-2-yl]-3-(5-amino-2-chlorophenyl)-propene-1-one The same method as employed in the preparation of Example 64 but starting from Example 87 gave after recrystallization from EtOH:DCM, the title compound as a white powder in a 17% yield. MP: 251–252δC.

Analysis for $C_{27}H_{22}ClN_3O_3.0.4H_2O$: Calculated: C,67.68; H,4.8; N,8.77; Found: C,67.71; H,4.73; N,8.65%.

EXAMPLE 91

(E)-3-Chloro-4-[3-oxo-3-[1-(3,4-methylenedioxyphenyl)-1,3,4,9-tetrahydro-β-carbolin-2-yl]-propenyl]benzoic acid The same method as employed in the preparation of Example 31 but starting from Example 88 gave after recrystallization from 2-propanol the title compound as a yellow powder in a 40% yield. MP: 169δC.

Analysis for $C_{28}H_{21}N_2O_5$. $H_2O$: Calculated: C,64.8; H,4.47; N,5.40; Found: C,64.47; H,4.13; N,5.60%.

EXAMPLE 92

(E)-1-[1-(3,4-Methylenedioxyphenyl)-1,3,4,9-tetrahydro-β-carbolin-2-yl]-3-(3, 5-dibromo-4-hydroxyphenyl)propene-1-one The same method as employed in the preparation of Example 20 but starting from (E)-3,5-dibromo-4-hydroxy cinnamic acid gave after recrystallization from EtOH:H$_2$O the title compound as white crystals in a 13% yield. MP: 148–150° C.

Analysis for $C_{27}H_{20}N_2O_4Br_2.1.6EtOH$: Calculated: C,54.14; H,4.45; N,4.18; Found: C,54.1; H,4.15; N,3.77%.

EXAMPLE 93

(E)-1-[1-(3,4-Methylenedioxyphenyl)-1,3,4,9-tetrahydro-β-carbolin-2-yl]-3-(4-(2-diinethylaminopropoxy)phenyl)propene-1-one The same method as employed in the preparation of Example 79 but starting from Example 22 and dimethylaminopropyl chloride gave after recrystallization from cyclohexane:DCM:pentane the title compound as white crystals in a 16% yield. MP: 106° C.

Analysis for $C_{32}H_{33}N_3O_4 \cdot 0.3H_2O$: Calculated: C,72.65; H,6.40; N,7.94; Found: C,72.74; H,6.56; N,7.63%.

EXAMPLE 94

(E)-2-Chloro-5-[3-oxo-3-[1-(3,4-methylenedioxyphenyl)-1,3,4,9-tetrahydro-β-carbolin-2-yl]-propenyl]benzoic acid, methyl ester The same method as employed in the preparation of Example 20 but starting from Intermediate 33 gave after recrystallization from MeOH:DCM the title compound as a white powder in a 59% yield. MP: 228° C.

Analysis for $C_{29}H_{23}ClN_2O_5 \cdot 1.05H_2O$: Calculated: C,65.24; H,4.74; N,5.25; Found: C,64.91; H,4.27; N,5.13%.

EXAMPLE 95

(E)-1-[1-(3,4-Methylenedioxyphenyl)-1,3,4,9-tetrahydro-β-carbolin-2-yl]-3-(4-(2-diisopropylaminoethoxy)phenyl)propene-1-one The same method as employed in the preparation of Example 79 but starting from Example 22 and diisopropylaminodiethyl chloride gave after recrystallization from MeOH:H₂O the title compound as pale yellow crystals in a 12% yield. MP: 92–93° C.

Analysis for $C_{35}H_{39}N_3O_4$: Calculated: C,74.31; H,6.95; N,7.43; Found: C,74.34; H,7.16; N,7.10%.

EXAMPLE 96

(E)-2-Chloro-5-[3-oxo-3-[1-(3,4-methylenedioxyphenyl)-1,3,4,9-tetrahydro-β-carbolin-2-yl]-propenyl]benzoic acid The same method as employed in the preparation of Example 31 but starting from Example 94 gave after recrystallization from MeOH the title compound as white crystals in a 78% yield. MP: 178° C.

Analysis for $C_{28}H_{21}N_2O_5 \cdot 0.7MeOH$: Calculated: C,65.86; H,4.58; N,5.35; Found: C, 65.73; H, 4.44; N, 5.51%.

EXAMPLE 97

(E)-1-[1-(3,4-Methylenedioxyohenyl)-1,3,4,9-tetrahydro-β-carbolin-2-yl]-3-(3-hydroxy-4-nitrophenyl)propene-1-one The same method as employed in the preparation of Example 20 but starting from Intermediate 34 gave after recrystallization from EtOH the title compound as yellow crystals in a 77% yield. MP: 172° C.

EXAMPLE 98

(E)-1-[1-(3,4-Methylenedioxyphenyl)-1,3,4,9-tetrahydro-β-carbolin-2-yl]-3-(3,5-dimethyl-4-hydroxyphenyl) propene-1-one The same method as employed in the preparation of Example 20 but starting from Intermediate 35 gave after recrystallization from MeOH:H₂O the title compound as a white powder in a 71% yield. MP: 151–152° C.

Analysis for $C_{29}H_{26}N_2O_4 \cdot 0.4H_2O$: Calculated: C,73.52; H,5.7; N,5.91; Found: C,73.56; H,5.59; N 6.29%0.

EXAMPLE 99

(E)-1-[1-(3,4-Methylenedioxyohenyl)-1,3,4,9-tetrahydro-β-carbolin-2-yl]-3-(3-(2-dimethylaminoethoxy)-4-nitro-phenyl) ipropene-1-one The same method as employed in the preparation of Example 79 but starting from Example 97 and dimethylaminodiethyl chloride gave after recrystallization from MeOH the title compound as a pale yellow powder in a 18% yield. MP: 189° C.

Analysis for $C_{31}H_{30}N_4O_6 \cdot 1.5H_2O$: Calculated: C,64.02; H,5.72; N,9.63; Found: C,64.18; H,5.41; N,9.21%.

EXAMPLE 100

(E)-1-[1-(3,4-Methylenedioxyphenyl)-1,3,4,9-tetrahydro-β-carbolin-2-yl]-3-(3-(2-dimethylaminoethoxy)-4-amino-phenyl) propene-1-one The same method as employed in the preparation of Example 64 but starting from Example 99 gave after recrystallization from iPr₂O the title compound as a pale yellow powder in a 17% yield. MP: 143° C.

Analysis for $C_{31}H_{32}N_4O_4 \cdot 0.5H_2O$: Calculated: C,69.78; H,6.23; N,10.5; Found: C,69.87; H,5.98; N,10.42%.

EXAMPLE 101

(E)-1-[-(3,4-Methylenedioxyphenyl)-1,3,4,9-tetrahydro-β-carbolin-2-yl]-3-(3-nitro-4-hydroxy-5-methoxyphenyl) propene-1-one The same method as employed in the preparation of Example 20 but starting from Intermediate 36 gave after recrystallization from EtOH:DCM the title compound as pale yellow crystals in a 45% yield.

MP: 172° C. Analysis for $C_{28}H_{23}N_3O_7 \cdot 0.8H_2O$: Calculated: C,63.7; H,4.7; N,7.96; Found: C,63.71; H,4.31; N,7.98%.

EXAMPLE 102

(E)-1-[-(3,4-Methylenedioxyphenyl)-1,34,9-tetrahydro-β-carbolin-2-yl]-3-(3-chlorophenyl) propene-1-one The same method as employed in the preparation of Example 20 but starting from (E)-3-chlorocinnamic acid, gave after recrystallization from EtOH the title compound as white crystals in a 48% yield.

MP: 212–213° C. Analysis for $C_{27}H_{21}ClN_2O$: Calculated: C,70.97; H,4.63; N,6.13 Found: C,70.65; H,4.63; N,6.16%.

EXAMPLE 103

(E)-1-[1-(4-Methoxy-phenyl)-1,3,4,9-tetrahydro-β-carbolin-2-yl]-3-(2-chloro-5-nitrophenyl) propene-1-one The same method as employed in the preparation of Example 20 but starting from Intermediate 2 and (E)-2-chloro-5-nitrocinnamic acid gave after recrystallization from 2-propanol the title compound as a yellow powder white in a 18% yield. MP: 136–1380C.

Analysis for $C_{27}H_{22}ClN_3O_4 \cdot 0.2H_2O$: Calculated: C,65.98; H,4.59; N,8.55; Found: C,65.91; H,4.4; N,8.42%.

EXAMPLE 104

(E)-1-[1-(3,4-Methylenedioxyphenyl)-1,3,4,9-tetrahydro-β-carbolin-2-yl]-3-(2,6-dichlorophenyl)-propene-1-one The same method as employed in the preparation of Example 20 but starting from (E)-2,6-dichlorocinnamic acid gave after recrystallization from cyclohexane the title compound as a white powder in a 41% yield. MP: 118–120° C.

Analysis for $C_{27}H_{20}Cl_2N_2O_3 \cdot 0.2H_2O$: Calculated: C,65.52; H,4.15; N,5.66; Found: C,65.74; H,4.62; N,5.29%0.

EXAMPLE 105

(E)-1-[1-(3,4-Methylenedioxyphenyl)-1,3,4,9-tetrahydro-β-carbolin-2-yl]-3-(4-methylaminomethyl-phenyl)-propene-1-one A solution of (E)-1-[1-(3,4-methylenedioxyphenyl)-1,3,4,9-tetrahydro-β-carbolin-2-yl]-3-(4-methyliminomethylphenyl)propene-1-one (0.46 g, 1.1 mmol), $NaBH_3CN$ (0.14 g, 2.3 mmol) and acetic acid (0.11 mL) in 20 mL of MeOH was stirred at rt for one hour. The reaction mixture was quenched with 50 rL of an aqueous saturated solution of $NaHCO_3$. Extraction with 2×30 mL of DCM, washing with brine, drying over $Na_2SO_4$ and concentration in vacuo gave a residue that was purified via flash chromatography of silica gel using DCM:MeOH (97:3) as eluting solvent. Recrystallization from DCM:cyclohexane gave the title compound (0.05 g, 10%) as a white powder. MP: 201° C.

Analysis for $C_{29}H_{27}Cl_2N_3O_3 \cdot 0.5H_2O$: Calculated: C,73, 4; H,5.95; N,8.85; Found: C,73.66; H,5.82; N,8.57%.

A stirred solution of Example 23 (0.5 g, 1.0 mmol) in MeOH was refluxed with methylamine (1.6 mL, 1.5 equiv., 33% in EtOH) for one hour. Evaporation in vacuo gave (E)-1-[1-(3,4-methylenedioxyphenyl)-1,3,4,9-tetrahydro-β-carbolin-2-yl]-3-(4-methyliminomethylphenyl)propene-1-one (0.46 g, 90%).

$^1H$ NMR ($CDCl_3$, 250 MHz) δ 8.2 (d, 1H), 8.1 (s, 1H), 7.8–7.65 (m, 3H), 7.55–7.5 (m, 3H), 7.4–7.1 (m, 3H), 7.0–6.85 (m, 2H), 6.8–6.6 (dd, 2H), 5.9 (s, 2H), 4.2–4.1 (br d, 1H), 3.5 (s+m, 4H), 3.05–2.85 (m, 2H).

EXAMPLE 106

(E)-1-[1-(3,4-Methylenedioxyphenyl)-1,3,4,9-tetrahydro-β-carbolin-2-yl]-3-(3-methylphenyl)propene-1-one The same method as employed in the preparation of Example 20 but starting from (E)-3-methylcinnamic acid gave after recrystallization from MeOH the title compound as a white powder in a 67% yield.

MP: 196° C. Analysis for $C_{28}H_{24}N_2O_3$: Calculated: C,77.04; H,5.54; N,6.62; Found: C,76.76; H,5.56; N,6.33%.

EXAMPLE 107

(E)-N-Methyl-(4-[3-oxo-3-(1-(3,4-methylenedioxyphenyl)-1,3,4,9-tetrahydro-β-carbolin-2-yl)-propenyl]benzenesulfonamide The same method as employed in the preparation of Example 20 but starting from (E)-4-(N-methylsulfonamide) cinnamic acid gave after recrystallization from EtOH:$H_2O$ the title compound as white crystals in a 79% yield. MP: 162° C.

Analysis for $C_2,H_2QN3O_5$ 0.4EtOH: Calculated: C,64.78; H,5.17; N,7.87; Found: C,64.46; H,4.82; N,7.76%.

EXAMPLE 108

(E)-1-[1-(3,4-Methylenedioxyphenyl)-1,3,4,9-tetrahydro-β-carbolin-2-yl]-3-(3-hydroxy-4-acetylphenyl)-propene-1-one The same method as employed in the preparation of Example 20 but starting from (E)-3-hydroxy-4-acetylcinnamic acid gave after recrystallization from EtOH the title compound as yellow crystals in a 87% yield. MP: 217–218° C.

Analysis for $C_{29}H_{24}N_2O_5$: Calculated: C,72.49; H,5.03; N,5.83; Found: C,72.24; H,5.25; N,5.53%.

EXAMPLE 109

(E)-1-[-(2,3-Dihydrobenzofuran-5-yl)-1,3,4,9-tetrahydro-β-carbolin-2-yl]-3-(2-chloro-5-nitrophenyl)-propene-1-one The same method as employed in the preparation of Example 20 but starting from Intermediate 10 and (E)-2-chloro-5-nitrocinnamic acid gave after recrystallization from EtOH:$H_2O$ (95:5) the title compound as yellow crystals in a 62% yield. MP: 154° C.

Analysis for $C_{27}H_{22}ClN_3O_4 \cdot 0.5$ ($H_2O$:MeOH) Calculated: C,66.08; H,4.55; N,8.36; Found: C,66.3; H,4.52; N,7.94%.

EXAMPLE 110

(E)-1-[1-(3,4-Methylenedioxyphenyl)-1,3,4,9-tetrahydro-β-carbolin-2-yl]-3-(2-hydroxyohenyl) propene-1-one The same method as employed in the preparation of Example 20 but starting from (E)-2-hydroxy cinnamic acid gave after recrystallization from EtOH:$H_2O$, the title compound as white crystals in a 47% yield.

MP: 154° C. Analysis for $C_{27}H_{22}N_2O_4 \cdot 0.6H_2O$: Calculated: C,72.18; H,5.2; N,6.24; Found: C,72.19; H,4,93; N,6.13%.

EXAMPLE 111

(E)-1-[1-(3,4-Methylenedioxyrhenyl)-1,3,4,9-tetrahydro-β-carbolin-2-yl]-3-(3-nitro-2-piperidin-1-yl-phenyl)propene-1-one The same method as employed in the preparation of Example 20 but starting from Intermediate 37 gave after recrystallization from MeOH the title compound as yellow crystals in a 31% yield. MP: 162–163° C.

Analysis for $C_{32}H_{30}N_4O_5 \cdot 0.2H_2O$: Calculated: C,65.52; H,5.84; N,9.55; Found: C,65.9; H,5.49; N,9.59%.

EXAMPLE 112

(E)-1-[1-(2,3-Dihydrobenzofuran-5-yl)-1,3,4,9-tetrahydro-8-carbolin-2-yl]-3-phenylpropene-1-one The same method as employed in the preparation of Example 1 but starting from Intermediate 10 gave after recrystallization from EtOH the title compound as white crystals in a 52% yield. MP: 190° C.

Analysis for $C_{28}H_{24}N_2O_2$: Calculated: C,79.98; H,5.75; N,6.66; Found: C,79.94; H,5.86; N,6.62%.

EXAMPLE 113

(E)-1-[1-(4-Isopropylphenyl)-1,3,4,9-tetrahydro-β-carbolin-2-yl]-3-(3-nitrophenyl)propene-1-one The same method as employed in the preparation of Example 20 but starting from Intermediate 11 and (E)-3-nitrocinnamic acid gave after recrystallization from EtOH the title compound as yellow crystals in a 54% yield. MP: 195° C.

Analysis for $C_{29}H_{27}N_3O_3$: Calculated: C,74.82; H,5.85; N,9.03; Found: C,74.43; H,5.84; N,9.17%.

EXAMPLE 114

(E)-1-[1-(2,3-Dihydrobenzofuran-5-yl)-1,3,4,9-tetrahydro-β-carbolin-2-yl]-3-(3-nitrophenyl)propene-1-one The same method as employed in the preparation of Example 20 but starting from Intermediate 10 and (E)-3-nitrocinnamic acid gave after recrystallization from EtOH the title compound as white crystals in a 35% yield. MP: 174–176° C.

Analysis for $C_{28}H_{23}N_3O_4.0.1H_2O$: Calculated: C,71.97; H,5.0; N,8.99; Found: C,71.78; H,4.89; N,8.83%.

EXAMPLE 115

(E)-(R)-1-[1-(3,4-Methylenedioxyphenyl)-1,3,4,9-tetrahydro-β-carbolin-2-yl]-3-phenylpropene-1-one The same method as employed in the preparation of Example 1 but starting from Intermediate 19 gave after recrystallization from EtOH the title compound as white crystals in a 60% yield. MP: 232–233° C.

Analysis for $C_{27}H_{22}N_2O_3.0.2H_2O$: Calculated: C,76.11; H,5.3; N,6.57; Found: C,76.2; H,5.27; N,6.77%

$[\alpha]D^{21}=-336$ (c=0.50, MeOH).

EXAMPLE 116

(E))-(S)-1-[1-(3,4-Methylenedioxyphenyl)-1,3,4,9-tetrahydro-β-carbolin-2-yl]-3-phenylpropene-1-one The same method as employed in the preparation of Example 1 but starting from Intermediate 18 gave after recrystallization from iPrOH the title compound as white crystals in a 32% yield. MP: 235–236° C.

Analysis for $C_{27}H_{22}N_2O_3$. $0.1H_2O$: Calculated: C,76.43; H,5.27; N,6.6; Found: C,76.26; H,5.21; N,6.61%.

$[\alpha]D^{21}=378$ (c=0.5, MeOH)

EXAMPLE 117

(E)-1-[1-(4-Methoxyphenyl)-1,3,4,9-tetrahydro-β-carbolin-2-yl]-3(3-nitrophenyl)propene-1-one The same method as employed in the preparation of Example 20 but starting from Intermediate 2 and (E)-3-nitrocinnamic acid gave after recrystallization from EtOH the title compound as yellow crystals in a 63% yield. MP: 227° C.

Analysis for $C_{27}H_{23}N_3O_4$. 0.1EtOH: Calculated: C,71,32; H,5.19; N,9.17; Found: C,70.96; H,5.14; N,9.23%.

EXAMPLE 118

(E)-1-[1-(4-Methylphenyl)-1,3,4,9-tetrahydro-β-carbolin-2-yl]-3-(2-chloro-5-nitrophenyl)propene-1-one The same method as employed in the preparation of Example 20 but starting from Intermediate 6 and (E)-2-chloro-5-nitrocinnamic acid gave after recrystallization from EtOH the title compound as a yellow powder in a 57% yield. MP: 211–213° C.

Analysis for $C_{27}H_{23}ClN_3O_3$: Calculated: C,68.72; H,4.7; N,8.9; Found: C,68.42; H,4.73; N,8.91%.

EXAMPLE 119

(E)-N-(Tetrahydrofuran-2-ylmethyl)-3-[3-oxo-3-(1-(3,4-methylenedioxy)-1,3,4,9-tetrahydro-β-carbolin-2-yl)-propenyl]benzamide The same method as employed in the preparation of Example 20 but starting from Example 70 and tetrahydro-furfurylamine gave after recrystallization from EtOH the title compound as a white powder in a 30% yield. MP: 172–1730C.

Analysis for $C_{33}H_{31}N_3O_5$. $0.4H_2O$: Calculated: C,71.18; H,5.76; N,7.55; Found: C,71.1; H,5.88; N,7.45%.

EXAMPLE 120

(E)-1-[1-(Indan-5-yl)-1,3,4,9-tetrahydro-β-carbolin-2-yl]-3-phenylpropene-1-one

The same method as employed in the preparation of Example 1 but starting from Intermediate 9 and tetrahydro-furfurylamine gave after recrystallization from EtOH the title compound as white crystals in a 51% yield. MP: 223° C.

Analysis for $C_{29}H_{26}N_2O$. $0.4H_2O$: Calculated: C,81.81; H,6.3,4; N,6.58; Found: C,81.87; H,6.3,4; N,6.5%.

EXAMPLE 121

(E)-1-[1-(3,4-Methylenedioxyphenyl)-1,3,4,9-tetrahydro-β-carbolin-2-yl]-3-(3-acetylphenyl)propene-1-one The same method as employed in the preparation of Example 20 but starting from 3-acetylcinnamic acid (prepared according to the procedure of Cleland, *J. Org. Chem.* 1969, 3,4, 744–747) gave after recrystallization from EtOH the title compound as a yellow powder in a 42% yield. MP: 191° C.

Analysis for $C_{29}H_{24}ClN_2O_4$: Calculated: C,74,98; H,5.21; N,6.03; Found: C,74.85; H,5.28; N,6.1%.

EXAMPLE 122

(E)-1-[1-(2,3-Dihydrobenzofuran-5-yl)-1,3,4,9-tetrahydro-β-carbolin-2-yl)]3-(4-(2-dimethylaminoethoxy)phenyl)propene-1-one The same method as employed in the preparation of Example 20 but starting from Intermediate 10 and Intermediate 25 gave after recrystallization from $CH_3CN$ the title compound as white crystals in a 37% yield. MP: 146° C.

Analysis for $C_{32}H_{33}N_3O_3$. $1.5H_2O$: Calculated: C,71.89; H,6.79; N,7.86; Found: C,72.04; H,7.09; N,7.93%.

EXAMPLE 123

(E)-4-[3-Oxo-3-[1-(4-methoxyphenyl)-1,3,49-tetrahydro-β-carbolin-2-yl]propenyl]benzoic acid, methyl ester The same method as employed in the preparation of Example 20 but starting from Intermediate 2 and (E)-4-(2-carboxy-vinyl)benzoic acid, methyl ester gave after recrystallization from EtOH the title compound as yellow crystals in a 73% yield. MP: 189° C.

Analysis for $C_{29}H_{26}N_2O_4$. 0.1EtOH: Calculated: C,74.44; H,5.69; N,5.95; Found: C,74.1; H, 5.65; N,6.01%.

EXAMPLE 124

(E)-1-[1-(3,4-Methylenedioxyphenyl)-1,3,4,9-tetrahydro-β-carbolin-2-yl]-3-(4-methyl-3,4-dihydro-2H-benzo[1,4]-oxazin-6-yl)propene-1-one The same method as employed in the preparation of Example 20 but starting from Intermediate 38 gave after recrystallization from EtOH the title compound as yellow crystals in a 69% yield. MP: 231–232° C.

Analysis for $C_{29}H_{26}N_2O_4$. 0.1EtOH: Calculated: C,73.01; H,5.51; N, 8.51; Found: C,72.54; H,5.58; N,8.44%.

EXAMPLE 125

(E)-1-[1-(3,4-Methylenedioxyphenyl)-1,3,4,9-tetrahydro-β-carbolin-2-yl]-3-(2-hydroxy-5-nitrophenyl)-propene-1-one The same method as employed in the preparation of Example 20 but starting from Intermediate 39 gave after recrystallization from EtOH the title compound as yellow crystals in a 30% yield. MP: 205° C.

Analysis for $C_{27}H_{21}N_3O_6$. 0.6EtOH: Calculated: C,65.78; H,5.14; N,7.94; Found: C,65.52; H,4,98; N,8.04%.

EXAMPLE 126

(E)-4-[3-Oxo-3-[1-(2,3-dihydrobenzofuran-5-yl)-1,3,4,9-tetrahydro-β-carbolin-2-yl]propenyl]benzoic acid, methyl ester The same method as employed in the preparation of Example 20 but starting from Intermediate 10 and (E)-4-(2-carboxyvinyl)benzoic acid, methyl ester gave after recrystallization from EtOH the title compound as white needles in a 88% yield. MP: 186° C.

Analysis for $C_{30}H_{26}N_2O_4$. 0.2H$_2$O: Calculated: C,74.73; H,5.52; N,5.81; Found: C,75.45; H, 5.38; N,6.07%.

EXAMPLE 127

(E)-4-[3-Oxo-3-[1-(4-methoxyphenyl)-1,3,4,9-tetrahydro-β-carbolin-2-yl]propenyl]benzoic acid The same method as employed in the preparation of Example 31 but starting from Example 123 gave after recrystallization from MeOH:H$_2$O the title compound as a grey powder in a 43% yield. MP: 147–149° C.

Analysis for $C_{28}H_{24}N_2O_4$: Calculated: C,74.32; H,5.35; N,6.19; Found: C,74.3; H,5.37; N,6.07%.

EXAMPLE 128

(E)-4-[3-Oxo-3-[1-(2,3-dihydrobenzofuran-5-yl)-1,3,4,9-tetrahydro-β-carbolin-2-yl]propenyl] benzoic acid The same method as employed in the preparation of Example 31 but starting from Example 126 gave after recrystallization from MeOH the title compound as white crystals in a 53% yield. MP: 222–224° C.

Analysis for $C_{29}H_{24}N_2O_4$: Calculated: C,74.98; H,5.21; N,6.03; Found: C,75.21; H,5.3; N,6.21%.

EXAMPLE 129

(E)-1-[1-(Benzofuran-5-yl)-1,3,4,9-tetrahydro-β-carbolin-2-yl]-3-phenylpropene-1-one The same method as employed in the preparation of Example 1 but starting from Intermediate 12 gave after recrystallization from EtOH the title compound as white crystals in a 35% yield. MP: 241–242° C.

Analysis for $C_{28}H_{22}N_2O_2$: Calculated: C,80.36; H,5.3; N,6.69; Found: C,80.44; H,5.3; N,6.89%.

EXAMPLE 130

(E)-3-[3-Oxo-3-(1-(3,4-methylenedioxyohenyl)-1,3,4,9-tetrahydro-β-carbolin-2-yl)propenyl]-phenyl) trifluoromethanesulfonic acid, phenyl ester The same method as employed in the preparation of Example 20 but starting from Intermediate 40 gave after recrystallization from EtOH the title compound as white crystals in a 38% yield. MP: 169° C.

Analysis for $C_{28}H_{21}F_3N_2O_6S$. 0.2H$_2$O: Calculated: C,58.58; H,3.76; N,4.88; Found: C,58.84; H,3.71; N,4.3%.

EXAMPLE 131

(E)-1-[1-(3,4-Methylenedioxyphenyl)-1,3,4,9-tetrahydro-β-carbolin-2-yl]-3-[4-(2-hydroxyethoxy)-phenyl]propene-1-one The same method as employed in the preparation of Example 20 but starting from (E)-4-(2-hydroxyethoxy) phenyl (prepared according to the procedure of Oku et al., EP β2361) gave after recrystallization from EtOH the title compound as white crystals in a 57% yield. MP: 136° C.

Analysis for $C_{29}H_{26}N_2O_5$. 1.2EtOH: Calculated: C,58.58; H,3.76; N,4.88; Found: C,58.84; H,3.71; N,4.3%.

EXAMPLE 132

(E)-1-[1-(Benzofuran-5-yl-1,3,4,9-tetrahydro-β-carbolin-2-yl)1-3-(4-(2-dimethylaminoethoxy) phenyl)-propene-1-one The same method as employed in the preparation of Example 20 but starting from Intermediate 12 and Intermediate 25 gave after recrystallization from CH$_3$CN the title compound as white crystals in a 23% yield. MP: 159° C.

Analysis for $C_{32}H_{31}N_3O_3$. 0.1H$_2$O: Calculated: C,75.75; H,6.2; N,8.28; Found: C,75.58; H,5.97; N,8.35%.

EXAMPLE 133

(E)-1-[1-(3,4-Methylenedioxy-henyl)-1,3,4,9-tetrahydro-β-carbolin-2-yl]-3-(2-dimethylaminophenyl)-propene-1-one The same method as employed in the preparation of Example 20 but starting from (E)-2-dimethylaminocinnamic acid (prepared according to the procedure of Suschitzky et al., *Synthesis* 1982, 662–665) gave after recrystallization from MeOH:H$_2$O the title compound as a yellow powder in a 51% yield. MP: 172° C.

Analysis for $C_{29}H_{27}N_3O_3$: Calculated: C,74.82; H,5.85; N,9.03; Found: C,74.75; H,5.85; N,8.9%.

EXAMPLE 134

(E)-1-[1-(3,4-Methylenedioxyphenyl)-1,3,4,9-tetrahydro-β-carbolin-2-yl]-3-(2-piperidin-1-ylhenyl)-propene-1-one The same method as employed in the preparation of Example 20 but starting from (E)-2-piperidin-1-ylcinnamic acid (prepared according to the procedure of Suschitzky et al., *Synthesis* 1982, 662–665) gave after recrystallization from MeOH:H$_2$O the title compound as a yellow powder in a 37% yield. MP: 129° C.

Analysis for $C_{32}H_{31}N_3O_3$: Calculated: C,76.02; H,6.18; N,8.31; Found: C,75.66; H,6.18; N,8.29%.

EXAMPLE 135

(E)-4-[3-Oxo-3-[1-(benzofuran-5-yl-1,3,4,9-tetrahydro-β-carbolin-2-yl]propenyl]benzoic acid, methyl ester The same method as employed in the preparation of Example 20 but starting from Intermediate 12 and (E)-4-(2- carboxyvinyl)benzoic acid methyl ester gave after recrystallization from EtOH the title compound as yellow crystals in a 76% yield. MP: 221° C.

Analysis for $C_{30}H_{24}N_2O_4$: Calculated: C,75.62; H,5.08; N,5.88; Found: C,75.75; H,5.31; N,5.86%.

EXAMPLE 136

(E)-4-[3-(1-Benzofuran-5-yl-1,3,4,9-tetrahydro-β-carbolin-2-yl)-3-oxo-propenyl]benzoic acid The same method as employed in the preparation of Example 31 but starting from Example 135 gave after recrystallization from $CH_3CN$ the title compound as yellow crystals in a 66% yield. MP: 283° C.

Analysis for $C_{29}H_{22}N_2O_4$. $0.6H_2O$: Calculated: C,73.59; H,4,94; N,5.92; Found: C,73,48; H,4.78; N,5.93%.

EXAMPLE 137

(E)-4-[3-Oxo-3-(1-(3,4-methylenedioxyphenyl)-1,3,4,9-tetrahydro-g-carbolin-2-yl)propenyl]phenyl)-trifluoromethanesulfonic acid, phenyl ester The same method as employed in the preparation of Example 20 but starting from Intermediate 41 gave after recrystallization from EtOH the title compound as white crystals in a 51% yield. MP: 254° C.

Analysis for $C_{28}H_{21}F_3N_2O_6S$: Calculated: C,58.95; H,3.71; N,4,91; Found: C,58.79; H,3.8; N,4.77%.

EXAMPLE 138

(E)-1-[1-(3,4-Methylenedioxyrhenyl)-1,3,4,9-tetrahydro-β-carbolin-2-yl]-3-(2-(2-dimethylaminoethoxy)-phenyl)propene-1-one The same method as employed in the preparation of Example 79 but starting from Example 110 and dimethylaminodiethyl chloride gave after recrystallization from $CH_3CN$:pentane the title compound as yellow crystals in a 70% yield.

MP: 131° C. Analysis for $C_{31}H_{31}N_3O_4$. $1.3H_2O$: Calculated: C,68.95; H,6.35; N,7.88; Found: C,69.; H,6.28; N,7.84%.

EXAMPLE 139

(E)-1-[1-(3-Fluoro-4-methoxyphenyl)-1,3,4,9-tetrahydro-β-carbolin-2-yl]-3-phenylpropene-1-one The same method as employed in the preparation of Example 1 but starting from Intermediate 14 gave after recrystallization from DCM:cyclohexane the title compound as white crystals in a 66% yield.

MP: 122° C. Analysis for $C_{27}H_{23}FN_2O_2$. $0.4CH_2Cl_2$: Calculated: C,71.47; H,5.21; N,6.08; Found: C,71.46; H,5.27; N,6.12%.

EXAMPLE 140

(E)-(R)-1-[1-(2 3-Dihydrobenzofuran-5-yl)-1,3,4,9-tetrahydro-β-carbolin-2-yl)1-3-(4-(2-dimethylaminoethoxy)iphenyl)propene-1-one The same method as employed in the preparation of Example 20 but starting from Intermediate 20 and Intermediate 25 gave after recrystallization from $CH_3CN$ the title compound as white crystals in a 85% yield. MP: 187–189° C.

Analysis for $C_{32}H_{33}N_3O_3$: Calculated: C,75.71; H,6.55; N,8.20; Found: C,75.60; H,6.76; N,8.10%.

$[a]D^{21}=-310$ (c=0.40, $CHCl_3$).

EXAMPLE 141

(E)-1-(2,3-Dihydrobenzo[1,4]dioxin-6-yl)-1,3,4,9-tetrahydro-β-carbolin-2-yl]-3-phenylpropene-1-one The same method as employed in the preparation of Example 1 but starting from Intermediate 13 gave after recrystallization from EtOH the title compound as white crystals in a 39% yield. MP: 216° C.

Analysis for $C_{28}H_{24}N_2O_3$. $0.6H_2O$: Calculated: C,75.18; H,5.68; N,6.26; Found: C,75.17; H,5.41; N,6.4%.

EXAMPLE 142

(E)-1-[1-(2,3-Dihydrobenzofuran-5-yl)-1,3,4,9-tetrahydro-β-carbolin-2-yl)]-3-(4-(2-pvrrolidin-1-yl-ethoxy)phenyl)propene-1-one The same method as employed in the preparation of Example 20 but starting from Intermediate 10 and Intermediate 42 gave after recrystallization from 2-propanol:$iPr_2O$ the title compound as white crystals in a 26% yield. MP: 152° C.

Analysis for $C_{34}H_{35}N_3O_3$. $0.5H_2O$: Calculated: C,75.25; H,6.69; N,7.74; Found: C,75.31; H,6.6; N,7.69%.

EXAMPLE 143

(E)-1-[1-(3,4-Methylenedioxyphenyl)-1,3,4,9-tetrahydro-β-carbolin-2-yl]-3-[4-pyrrolidin-1-ylphenyl]-propene-1-one The same method as employed in the preparation of Example 20 but starting from Intermediate 43 gave after recrystallization from EtOH:$H_2O$ the title compound as white crystals in a 73% yield. MP: 154° C.

Analysis for $C_{31}H_{29}N_3O_3$. $0.6H_2O$: Calculated: C,74.11; H,6.06; N,8.36; Found: C,74.22; H,5.97; N,7.97%.

EXAMPLE 144

(E)-(R)-1-1-(2.3-Dihydrobenzofuran-5-yl)-1,3,4,9-tetrahydro-β-carbolin-2-yl]-3-(3-nitrophenyl)-propene-1-one The same method as employed in the preparation of Example 20 but starting from Intermediate 20 and (E)-3-nitrocinnamic acid gave after recrystallization from EtOH the title compound as yellow crystals in a 51% yield. MP: 155° C.

Analysis for $C_{28}H_{23}N_3O_4$: Calculated: C,72.25; H,4,98; N,9.03; Found: C,72.2; H,5.0; N,9.01%.

$[a]D^{19}=-347$ (c=0.33, MeOH).

EXAMPLE 145

(E)-1-[1-(3,4-Methylenedioxyphenyl)-1,3,4,9-tetrahydro-β-carbolin-2-yl]-3-[4-imidazol-1-ylphenyl]-propene-1-one The same method as employed in the preparation of Example 20 but starting from Intermediate 44 gave after recrystallization from EtOH the title compound as white crystals in a 69% yield. MP: 204° C.

Analysis for $C_{30}H_{24}N_4O_3$. $0.6H_2O$: Calculated: C,72.68; H,5.04; N,11,3; Found: C,72.67; H,4.85; N,11,3,4%.

EXAMPLE 146

(E)-4-[3-[1-(2,3-Dihydrobenzo[1,4]dioxin-6-yl)-1,3,4,9-tetrahydro-β-carbolin-2-yl]-3-oxopropenyl]-benzoic acid, methyl ester The same method as employed in the preparation of Example 20 but starting from Intermediate 13 and (E)-4-(2-carboxyvinyl)benzoic acid, methyl ester gave after recrystallization from MeOH the title compound as a white powder in a 35% yield. MP: 136° C.

Analysis for $C_{30}H_{26}N_2O_5$. $0.1H_2O$: Calculated: C,72.6; H,5.32; N, 5.64; Found: C,72.31; H,5.26; N,5.74%.

EXAMPLE 147

(E)-1-[1-(2,3-Dihydrobenzo[1,4]dioxin-6-yl)-1,3,4,9-tetrahydro-β-carbolin-2-yl]-3-(3-nitroohenyl)-propene-1-one The same method as employed in the preparation of Example 20 but starting from Intermediate 13 and (E)-3-nitrocinnamic acid gave after recrystallization from EtOH the title compound as a pale yellow powder in a 93% yield. MP: 154° C.

Analysis for $C_{28}H_{23}N_3O_5$. $0.6H_2O$: Calculated: C,68.31; H,4.95; N,8.54; Found: C,68.41; H,4.87; N,8.61%.

EXAMPLE 148

(E)-1-[1-(2,3-Dihydrobenzo-1,4]dioxin-6-yl)-1,3,4,9-tetrahydro-β-carbolin-2-yl)1-3-(4-(2-dimethylaminoethoxy)phenyl)propene-1-one The same method as employed in the preparation of Example 20 but starting from Intermediate 13 and Intermediate 25 gave after recrystallization from $CH_3CN$ the title compound as a white powder in a 65% yield. MP: 145° C.

EXAMPLE 149

(E)-1-[1-(3-Fluoro-4-methoxyohenyl)-1,3,4,9-tetrahydro-β-carbolin-2-yl)1-3-(4-(2-dimethylaminoethoxy)phenyl)propene-1-one The same method as employed in the preparation of Example 20 but starting from Intermediate 14 and Intermediate 25 gave after recrystallization from $iPr_2O$ the title compound as a white powder in a 60% yield. MP: 103° C.

Analysis for $C_{31}H_{32}FN_3O_3$. $0.4H_2O$: Calculated: C,71.49; H,6.35; N,8.07; Found: C,71.4; H,6.51; N,8.04%.

EXAMPLE 150

(E)-4-[3-[1-(2, 3-Dihydrobenzo[1,4]dioxin-6-yl)-1,3,4,9-tetrahydro-3-carbolin-2-yl]-3-oxopropenyl]-benzoic acid The same method as employed in the preparation of Example 31 but starting from Example 146 gave after recrystallization from MeOH the title compound as a white powder in a 93% yield. MP: 253° C.

Analysis for $C_{29}H_{24}N_2O_5$. $0.7H_2O$: Calculated: C,70.63; H,5.19; N,5.68; Found: C,70.78; H,5.09; N,5.72%.

EXAMPLE 151

(E)-(R)-1-[1-(2 3-Dihydrobenzofuran-5-yl)-1,3,4,9-tetrahydro-β-carbolin-2-yl]-3-phenylpropene-1-one The same method as employed in the preparation of Example 1 but starting from Intermediate 20 gave after recrystallization from MeOH the title compound as white crystals in a 100% yield. MP: 267° C.

Analysis for $C_{28}H_{24}N_2O_2$: Calculated: C,79.98; H,5.75; N,6.66; Found: C,79.86; H,5.89; N,6.72%.

$[a]D^{22}$=−362 (c=0.35, $CHCl_3$)

EXAMPLE 152

(E)-(S)-1-[1-(2,3-Dihydrobenzofuran-5-yl)-1,3,4,9-tetrahydro-β-carbolin-2-yl)1-3-(4-(2-dimethylaminoethoxy)phenyl)ipropene-1-one The same method as employed in the preparation of Example 20 but starting from Intermediate 21 and Intermediate 25 gave after recrystallization from $CH_3CN$ the title compound as beige crystals in a 79% yield. MP: 153° C.

Analysis for $C_{32}H_{33}N_3O_3$. $0.5H_2O$: Calculated: C,74.39; H,6.63; N,8.13; Found: C,74.36; H,6.69; N,8.44%.

$[a]D^{21}$=314 (c=0.40, $CHCl_3$)

EXAMPLE 153

(E)-1-[1-(2,3-Dihydrobenzofuran-5-yl)-1,3,4,9-tetrahydro-β-carbolin-2-yl]-3-(4-aminophenyl)propene-1-one The same method as employed in the preparation of Example 20 but starting from Intermediate 10 and (E)-4-aminocinnamic acid gave after recrystallization from iPrOH the title compound as white crystals in a 43% yield. MP: 183° C.

Analysis for $C_{30}H_{31}N_3O_2$. $1.6H_2O$: Calculated: C,76.59; H,5.83; 9.57; Found: C,76.62; H,5.82; N,9.59%.

EXAMPLE 154

(E)-(S)-1-[1-(2,3-Dihydrobenzofuran-5-yl)-1,3,4,9-tetrahydro-g-carbolin-2-yl]-3-phenylpropene-1-one The same method as employed in the preparation of Example 1 but starting from Intermediate 21 gave after recrystallization from EtOH the title compound as white crystals in a 98% yield. MP: 266° C.

Analysis for $C_{28}H_{24}N_2O_2$. $0.2H_2O$: Calculated: C,79.30; H,5.80; N,6.61; Found: C,79.24; H,5.92; N,6.48%.

$[a]D^{20}$=356 (c=0.35, $CHCl_3$)

EXAMPLE 155

(E)-(S)-1-[1-(2,3-Dihydrobenzofuran-5-yl)-1,3,4,9-tetrahydro-β-carbolin-2-yl]-3-(3-nitrophenyl)-propene-1-one The same method as employed in the preparation of Example 20 but starting from Intermediate 21 and (E)-3-nitrocinnamic acid gave after recrystallization from 2-propanol the title compound as yellow crystals in a 77% yield. MP: 143° C.

Analysis for $C_{28}H_{23}N_3O_4$. $0.3H_2O$: Calculated: C,71.42; H,5.05; N,8.92; Found: C,71.51; H,4,98; N,9.23%.

$[a]D^{19}$=294 (c=0.30, $CHCl_3$)

EXAMPLE 156

(E)-(R)-1-[1-(2,3-Dihydrobenzofuran-5-yl)-1,3,4,9-tetrahydro-β-carbolin-2-yl)1-3-(4-(1-(S)-methyl-pyrrolidin-2-yl-methoxy)rphenyl)propene-1-one The same method as employed in the preparation of Example 20 but starting from Intermediate 20 and Intermediate 45 gave after recrystallization from 2-propanol the title compound as white crystals in a 73% yield. MP: 167° C.

Analysis for $C_{34}H_{35}N_3O_3$: Calculated: C,76.52; H,6.61; N,7.87; Found: C,76.13; H, 6.71; N,7.96%.

$[a]D^{20}=-344$ (c=0.30, $CHCl_3$)

EXAMPLE 157

(E)-(R)-1-[1-(2,3-Dihydrobenzofuran-5-yl)-1,3,4,9-tetrahydro-β-carbolin-2-yl]-3-(3-hydroxyphenyl)-propene-1-one The same method as employed in the preparation of Example 20 but starting from Intermediate 20 and (E)-3-hydroxycinnamic acid gave after recrystallization from EtOH the title compound as white crystals in a 93% yield. MP: 251° C.

Analysis for $C_{28}H_{24}N_2O_3$. $0.8H_2O$: Calculated: C,74.58; H,5.72; N,6.21; Found: C,74.58; H,5.65; N,6.17%.

$[a]D^{21}=-342$ (c=0.53, $CHCl_3$).

EXAMPLE 158

(E)-(R)-1-[1-(2,3-Dihydrobenzofuran-5-yl)-1,3,4,9-tetrahydro-β-carbolin-2-yl)1-3-(4-(2-dimethylamino-1-methylethoxy)pDhenyl)-propene-1-one The same method as employed in the preparation of Example 20 but starting from Intermediate 20 and Intermediate 46 gave after recrystallization from $CH_3CN$ the title compound as white crystals in a 100% yield. MP: 193° C.

Analysis for $C_{33}H_{35}N_3O_3$. $0.45H_2O$: Calculated: C,74.82; H,6.83; N,7.93; Found: C,74.85; H, 6.76; N,8.21%.

EXAMPLE 159

(E)-1-(1-Phenyl-1,3,4,9-tetrahydro-β-carbolin-2-yl)-3-(4-(4-methylpyperazin-1-yl)-phenyl)propene-1-one The same method as employed in the preparation of Example 20 but starting from Intermediate 1 and Intermediate 47 gave after recrystallization from EtOH the title compound as pale yellow crystals in a 26% yield. MP: 223–226° C.

Analysis for $C_{32}H_{32}N_4O_3$. $0.4H_2O$: Calculated: C,72.82; H,6.26; N,10.61; Found C,72.77; H,6.31; N,10.52%.

EXAMPLE 160

(E)-(R)-1-[1-(3,4-Methylenedioxyphenyl)-1,3,4,9-tetrahydro-β-carbolin-2-yl)1-3-(4-(1-(S)-methyl-pyrrolidin-2-yl-methoxy)phenyl)ppropene-1-one The same method as employed in the preparation of Example 20 but starting from Intermediate 19 and Intermediate 45 gave after recrystallization from $iPr_2O$ the title compound as white crystals in a 83% yield. MP: 164° C.

Analysis for $C_{33}H_{33}N_3O_4$. $0.9H_2O$: Calculated: C,71.82; H,6.36; N,7.61; Found C,72.05; H,6.57; N,7.24%.

$[\alpha]D^{21}=-285$ (c=0.40, $CHCl_3$)

EXAMPLE 161

(E)-(R)-1-[1-(3,4-Methylenedioxyphenyl)-1,3,4,9-tetrahydro-β-carbolin-2-yl)]-3-(4-(2-dimethylamino-1-methylethoxy)phenyl)propene-1-one The same method as employed in the preparation of Example 20 but starting from Intermediate 19 and Intermediate 46 gave after recrystallization from $iPr_2O$ the title compound as white crystals in a 56% yield. MP: 107° C.

Analysis for $C_{32}H_{33}N_3O_4$. $0.7H_2O$: Calculated: C,71.67; H,6.47; N,7.84; Found: C,71.6; H, 6.53; N,7.97 %.

EXAMPLE 162

(E)-(R)-1-[1-(3,4-Methylenedioxyphenyl)-1,3,4,9-tetrahydro-β-carbolin-2-yl)1-3-(4-(2-dimethylamino-propoxy)phenyl)propene-1-one The same method as employed in the preparation of Example 20 but starting from Intermediate 19 and Intermediate 48 gave after recrystallization from $iPr_2O$ the title compound as white crystals in a 78% yield. MP: 193° C.

Analysis for $C_{32}H_{33}N_3O_4$. $1.6H_2O$: Calculated: C,69.57; H,6.6; N,7.61; Found: C,69.46; H, 6.59; N,7.33%.

$[a]D^{21}=-266$ (c=0.40, $CHCl_3$).

EXAMPLE 163

(E)-4-[3-Oxo-3-[1-(3,4-fluorophenyl)-1,3,4,9-tetrahydro-β-carbolin-2-yl]-propenyl]benzoic acid, methyl ester The same method as employed in the preparation of Example 20 but starting from Intermediate 15 and (E)-4-(2-carboxyvinyl)benzoic acid, methyl ester gave after recrystallization from $EtOH:H_2O$ the title compound as a yellow powder in a 100% yield. MP: 200° C.

Analysis for $C_{28}H_{22}F_2N_2O_3$: Calculated: C,71.18; H,4.69; N,5.93; Found: C,71.21; H,4.77; N,6.03%.

EXAMPLE 164

(E)-(R)-[1-(2,3-Dihydrobenzofuran-5-yl)-1,3,4,9-tetrahydro-β-carbolin-2-yl)1-3-(4-(2-diethylaminoethoxyy)phenyl)propene-1-one The same method as employed in the preparation of Example 20 but starting from Intermediate 20 and (E)-3-(4-(2-diethylaminoethoxy)phenyl)acrylic acid (prepared according to the procedure of Sharpe et al., *J. Med. Chem.* 1971, 14, 836–842), gave after recrystallization from $CH_3CN$ the title compound as white crystals in a 80% yield. MP: 193° C. Analysis for $C_{34}H_{37}N_3O_3$. $0.6H_2O$: Calculated: C,74.73; H,7.05; N,7.69; Found: C,74.53; H, 6.91; N,7.68%.

$[a]D^{20}=-311$ (c=0.30, $CHCl_3$).

EXAMPLE 165

(E)-(R)-1-[1-(2,3-Dihydrobenzofuran-5-yl)-1,3,4,9-tetra-hydro-β-carbolin-2-yl)1-3-(4-(2-dimethylaminopropoxy)phenyl)propene-1-one The same method as employed in the preparation of Example 20 but starting from Intermediate 20 and Intermediate 48 gave after recrystallization from $CH_3CN$ the title compound as white crystals in a 79% yield. MP: 193° C.

Analysis for $C_{33}H_{35}N_3O_3$: Calculated: C,75.98; H,6.76; N,8.06; Found: C,76.24; H, 6.76; N,8.21%.

$[\alpha]D^{20}=-293$ (c=0.40, $CHCl_3$)

EXAMPLE 166

(E)-4-[3-Oxo-3-[1-(3,4-difluorophenyl)-1,3,4,9-tetrahydro-β-carbolin-2-yl]propenyl]benzoic acid The same method as employed in the preparation of Example 31 but starting from Example 163 gave after recrystallization from MeOH:H$_2$O the title compound as a white powder in a 100% yield. MP: 172° C.

Analysis for C$_{27}$H$_{20}$F$_2$N$_2$O$_3$: Calculated: C,68.06; H,4.65; N,5.88; Found: C,68.15; H,4.55; N,5.99%.

EXAMPLE 167

(E)-(R)-1-[1-(2,3-Dihydrobenzofuran-5-yl)-1,3,4,9-tetrahydro-β-carbolin-2-yl1-3-(4-aminophenyl)-propene-1-one The same method as employed in the preparation of Example 20 but starting from Intermediate 20 and (E)-4-aminocinnamic acid gave after recrystallization from 2-propanol the title compound as white crystals in a 80% yield. MP: 176° C.

Analysis for C$_{28}$H$_{25}$N$_3$O$_2$. 0.23H$_2$O: Calculated: C,76.49; H,5.84; N,9.56; Found: C,76.21; H, 5.61; N,9.96%.

[α]$D^{21}$=−375.3 (c=0.0.35, CHCl$_3$).

EXAMPLE 168

(E)-(R)-1-[1-(3,4-Methylenedioxyphenyl)-1,3,4,9-tetrahydro-β-carbolin-2-yl]-3-(4-aminophenyl)-propene-1-one The same method as employed in the preparation of Example 20 but starting from Intermediate 19 and (E)-4-aminocinnamic acid gave after recrystallization from 2-propanol:H$_2$O the title compound as white crystals in a 63% yield. MP: 264° C.

Analysis for C$_{27}$H$_{23}$N$_3$O$_3$. 0.6H$_2$O: Calculated: C,72.3,4; H,5.44; N,9.37; Found: C,72.06; H,5.48; 9.55%.

[α]$D^{21}$=−266 (c=0.3, MeOH).

EXAMPLE 169

(R)-(E)-1-[1-(3,4-Methylenedioxyphenyl)-1,3,4,9-tetrahydro-β-carbolin-2-yl)]-3-(4-(2-pyrrolidin-1-ylethoxy)phenyl)propene-1-one The same method as employed in the preparation of Example 20 but starting from Intermediate 19 and Intermediate 42 gave after recrystallization from iPr$_2$O the title compound as brown crystals in a 4% yield. MP: 116° C.

Analysis for C$_{33}$H$_{33}$N$_3$O$_4$. 1.7H$_2$O: Calculated: C,69.99; H,6.48; N,7.42; Found: C,70.02; H, 6.47; N,7.59%.

EXAMPLE 170

(E)-(R)-1-8-(3,4-Methylenedioxyrhenyl)-1,3,4,9-tetra-hydro-β-carbolin-2-yl)1-3-(4-(2-diethylaminoethoxy)phenylpropene-1-one The same method as employed in the preparation of Example 20 but starting from 1 Intermediate 19 and (E)-3-(4-(2-diethylaminoethoxy)phenyl)acrylic acid (prepared according to the procedure of Sharpe et al., *J. Med. Chem.* 1971, 14(9), 836–842) gave after recrystallization from iPr$_2$O the title compound as white crystals in a 67% yield. MP: 94° C.

Analysis for C$_{33}$H$_{35}$N$_3$O$_4$. 0.5H$_2$O: Calculated: C,72.5; H,6.64; N,7.69; Found: C,72.48; H,6.64; N,7.58%.

[α]$D^{21}$=−287 (c=0.3, CHCl$_3$).

EXAMPLE 171

(E)-1-[1-(3-Fluoro-4-methoxyohenyl)-1,3,4,9-tetrahydro-β-carbolin-2-yl)]-3-(3-nitrophenyl)propene-1-one The same method as employed in the preparation of Example 20 but starting from Intermediate 14 and (E)-3-nitrocinnamic acid gave after recrytallization from DCM:2-propanol the title compound as a yellow powder in a 90% yield. MP: 141° C.

Analysis for C$_{27}$H$_{22}$FN3O$_4$. 0.9CH$_2$Cl$_2$: Calculated: C,61.16; H,4.38; N,7.67; Found: C,61.1; H,4.39; N,7.56%.

EXAMPLE 172

(E)-(R)-1-[1-(2,3-Dihydrobenzofuran-5-yl)-1,3,4,9-tetra-hydro-β-carbolin-2-yl1-3-(4-trifluoromethyl-phenyl)propene-1-one The same method as employed in the preparation of Example 20 but starting from Intermediate 20 and (E)-4-trifluoromethylcinnamic acid gave after recrystallization from 2-propanol the title compound as white crystals in a 91% yield. MP: 141° C.

Analysis for C$_{29}$H$_{23}$F$_3$N$_2$O$_2$: Calculated: C,71,3; H,4.75; N,5.73; Found: C,71,37; H,4.79; N,5.86%.

[α]$D^{20}$=−326 (c=0.3, CHCl$_3$).

EXAMPLE 173

(E)-(R)-1-[1-(2,3-Dihydrobenzofuran-5-yl)-1,3,4,9-tetrahydro-β-carbolin-2-yl]-3-(3-trifluoromethylphenyl)propene-1-one The same method as employed in the preparation of Example 20 but starting from Intermediate 20 and (E)-3-trifluoromethylcinnamic acid gave after recrystallization from 2-propanol:H$_2$O the title compound as white crystals in a 80% yield. MP: 223° C.

Analysis for C$_{29}$H$_{23}$F$_3$N$_2$O$_2$: Calculated: C,71,3; H,4.75; N,5.73; Found: C,71.44; H,4.73; N,5.85%.

[a]$D^{20}$=−326 (c=0.3, CHCl$_3$)

EXAMPLE 174

(E)-(R)-1-[1-(2,3-Dihydrobenzofuran-5-yl)-1,3,4,9-tetra-hydro-β-carbolin-2-yl]-3-(4-(2-morpholin-4-ylethoxy)rphenyl)propene-1-one The same method as employed in the preparation of Example 20 but starting from Intermediate 20 and Intermediate 49 gave after recrystallization from 2-propanol:H$_2$O the title compound as white crystals in a 66% yield. MP: 148° C.

Analysis for C$_{34}$H$_{35}$N$_3$O$_4$: Calculated: C,71,3; H,4.75; N,5.73; Found: C,71.44; H,4.73; N,5.85%.

[α]$D^{19}$=−288 (c=0.3, CHCl$_3$)

EXAMPLE 175

(E)-(R)-1-[1-(2,3-Dihydrobenzofuran-5-yl)-1,3,4,9-tetrahydro-β-carbolin-2-yl]-3-(4-(2-(ethylmethylamino)ethoxy)phenyl)propene-1-one The same method as employed in the preparation of Example 20 but starting from Intermediate 20 and Intermediate 50 gave after recrystallization from iPr$_2$O the title compound as a white powder in a 66% yield. MP: 107° C.

Analysis for C$_{33}$H$_{35}$N$_3$O$_3$. 0.8H$_2$O: Calculated: C,73.94; H,6.88; N,7.84; Found: C,74.09; H,7.15; N,7.48%.

[α]$D^{21}$=−253 (c=0.3, CHCl$_3$)

EXAMPLE 176

(E)-1-[1-(2 3-Dihydrobenzofuran-5-yl)-1,3,4,9-tetrahydro-β-carbolin-2-yl]-3-(4-(3-(dimethylamino) propenyl)phenyl)propene-1-one The same method as employed in the preparation of Example 20 but starting from Intermediate 20 and Intermediate 51 gave after recrystallization from EtOH the title compound as a white powder in a 45% yield. MP: 216° C.

Analysis for $C_{33}H_{33}N_3O_2 \cdot 0.2H_2O$: Calculated: C,78.14; H,6.88; N,7.84; Found: C,78.03; H,6.74; N,8.21%.

$[\alpha]D^{19.8}=-312$ (c=0.29, $CHCl_3$).

EXAMPLE 177

(E)-(R)-)1-[1(2,3-Dihydrobenzofuran-5-yl)-1,3,4,9-tetra-hydro-β-carbolin-2-yl]-3-(4-(3-dimethylamino-2-hydroxypropoxy)Tphenyl)propene-1-one At 0° C. to a solution (E)-(R)-1-[1-(2,3-dihydrobenzofuran-5-yl)-1,3,4,9-tetrahydro-β-carbolin-2-yl]-3-(4-(2-(tert-butyldimethylsilanyloxy)-3-dimethylamino-2-hydroxy-propoxy)phenyl)propene-1-one (0.4 g, 0.6 mmol) in 50 mL of anhydrous THF was added tetrabutylammonium fluoride (0.6 mL, 1 equiv., 1 M in THF). The resulting mixture was stirred at rt for one day. Quenching with water, extraction with DCM, washing with brine, drying over $MgSO_4$ and concentration in vacuo gave an oil. Recrystallization from $iPrOH:H_2O$ gave the title compound (0.2 g, 62%) as an off-white powder. MP: 138° C.

Analysis for $C_{33}H_{35}N_3O_4 \cdot 0.5H_2O$: Calculated: C,72.5; H,6.64; N,7.69; Found: C,72.21; H,6.75; N,7.48%.

$[\alpha]D^{20}=-283$ (c=0.6, $CHCl_3$) (E)-(R)-1-[1-(2,3-Dihydrobenzofuran-5-yl)-1,3,4,9-tetra-hydro-β-carbolin-2-yl]-3-(4-(2-(tertbutyl-dimethylsilanyloxy)-3-dimethylamino-2-hydroxypropoxy)phenyl)propene-1-one was obtained in a 89% yield as a yellow oil from the same method as employed in the preparation of Example 20 but starting from Intermediate 20 and Intermediate 52.

$^1$H NMR ($CDCl_3$,250 MHz) δ 8.1 (s, 1H), 7.5–7.3 (m, 2H), 6.9–7.2 (m, 7H), 6.8–6.5 (m, 3H), 4.5 (t, 2H), 4.2 (m, 1H), 4.0 (m, 3H), 3.8 (m, 1H), 3.3 (m, 1H), 3.0 (t, 2H), 2.7–2.9 (m, 3H), 2.3–2.15 (m, 2H), 2.1 (s, 6H), 0.8 (s,9H), 0.05 (d, 6H).

EXAMPLE 178

(E)-(R)-1-(1-(2,3-Dihydrobenzofuran-5-yl)-1,3,4,9-tetrahydro-β-carbolin-2-yl)-3-(4-formylphenyl)-propene-1-one The same method as employed in the preparation of Example 20 but starting from Intermediate 20 and (E)-4-formylcinnamic acid gave after recrystallization from EtOH the title compound as a white powder in a 53% yield. MP: 175° C.

Analysis for $C_{29}H_{24}N_2O_3 \cdot 0.8H_2O$: Calculated: C,75.24; H,5.57; N,6.05; Found: C,75.54; H,5.78; N,6.11%.

$[\alpha]D^{20}=-3,40$ (c=0.33, $CHCl_3$).

EXAMPLE 179

(E)-(R)-1-[1-(2,3-Dihydrobenzofuran-5-yl)-1,3,4,9-tetra-hydro-β-carbolin-2-yl]-3-(4-propylamino-methyl)phenyl) propene-1-one To a solution of a solution of Example 178 (0.5 g, 1.1 mmol) in 50 mL of MeOH was added propylamine (14 mL, 1.5 equiv.). The resulting mixture was stirred at 50° C. for 4 hours. At rt polymer-supported borohydride (1.2 g, 1.2 equiv., 2.5 mmol/g) was added and the resulting mixture was stirred at 50° C. for 6 hours. After evaporation in vacuo, the residue was washed with 2×50 mL of DCM. After filtration, the filtrate was washed with 2×50 mL of water. Drying over $Na_2SO_4$, evaporation in vacuo and recrystallization from MeOH gave the title compound (0.4 g, 81%) as a pale yellow powder. MP: 170° C.

Analysis for $C_{32}H_{33}N_3O_2 \cdot 0.4H_2O$: Calculated: C,77.05; H,6.83; N,8.42; Found: C,77.04; H,6.78; N,8.29%.

$[\alpha]D^9=-330$ (c=0.4, MeOH)

EXAMPLE 180

(E)-(R)-1-[1-(2,3-Dihydrobenzofuran-5-yl)-1,3,4,9-tetra-hydro-β-carbolin-2-y11-3-f4-(2-dimethylamino-ethylamino)phenylpropene-1-one The same method as employed in the preparation of Example 20 but starting from Intermediate 20 and Intermediate 53 gave after recrystallization from EtOH the title compound as yellow crystals in a 12% yield. MP: 160° C.

Analysis for $C_{32}H_{34}N_4O_2 \cdot 0.2H_2O$: Calculated: C,75.33; H,6.8; N,10.98; Found C,75.06; H,6.83; N,10.98%.

$[\alpha]D^{20}=-214$ (c=0.1, MeOH).

EXAMPLE 181

(E)-(R)-1-[1-(2,3-Dihydrobenzofuran-5-yl)-1,3,4,9-tetrahydro-β-carbolin-2-yl]-3-(4-(2-aminoethoxy)-phenyl)propene-1-one To a solution of (E)-(R)-2-[2-(4-{3-[1-(2,3-dihydrobenzofuran-5-yl)-1,3,4,9-tetrahydro-β-carbolin-2-yl]-3-oxo-propenyl}-phenoxy)ethyl]isoindole-1,3-dione (0.85 g, 1.4 mmol) in 50 mL of MeOH:THF was added hydrazine (0.38 mL, 3 equiv., 35% in water). The resulting mixture was stirred at 45° C. for 4 hours. Evaporation in vacuo and flash chromatography with DCM:MeOH (80:20) as eluting solvent gave the title compound (0.17 g, 26%) as yellow powder. MP: 186° C.

Analysis for $C_{30}H_{29}N_3O_3 \cdot 0.3CH_2Cl_2$: Calculated: C,72.06; H,5.91; N,8.32; Found C,72.12; H,6.08; N,8.67%.

$[\alpha]D^{20}==285$ (c=0.29, MeOH) (E)-(R)-2-[2-(4-{3-[1-(2,3-Dihydrobenzofuran-5-yl)-1,3,4,9-tetrahydro-β-carbolin-2-yl]-3-oxo-propenyl}-phenoxy)ethyl]isoindole-1,3-dione was obtained after recrystallization from EtOH, as a gummy solid in a 90% yield using the same method as employed in the preparation of Example 20 but starting from Intermediate 20 and Intermediate 54.

$^1$H NMR ($CDCl_3$ 250 MHz) δ 8.0–6.7 (m, 19H), 4.5 (t, 2H), 4.2–4.0 (m, 5H), 3,4 (m, 1H), 3.0 (t, 2H), 2.9 (m, 2H).

EXAMPLE 182

(E)-(R)-1-1-(2,3-Dihydrobenzofuran-5-yl)-1,3,4,9-tetrahydro-β-carbolin-2-yl]-3-(4-hydroxyphenyl)-propene-1-one The same method as employed in the preparation of Example 20 but starting from Intermediate 20 and (E)-4-hydroxycinnamic acid gave after recrystallization from DMF:MeOH the title compound as a white powder in a 90% yield. MP: 189° C.

Analysis for $C_{28}H_{24}N_2O_3 \cdot 0.5DMF$: Calculated: C,75.51; H,5.77; N,7.12; Found: C,75.31; H,5.84; N,6.81%.

$[\alpha]D^{20}=-310$ (c=0.32, MeOH).

EXAMPLE 183

(E)-(R)-1-[1-(2.3-Dihydrobenzofuran-5-yl)-1,3,4,9-tetrahydro-β-carbolin-2-yl]-3-(4-(4-methylpiperazin-1-yl)phenylpropene-1-one The same method as employed in the preparation of Example 20 but starting from Intermediate 20 and Intermediate 47 gave after recrystallization from DMF:EtOH the title compound as pale yellow crystals in a 48% yield. MP: 193° C.

Analysis for $C_{33}H_{34}N_4O_2$. 1.0DMF: Calculated: C,73.07; H,6.98; N,11.83; Found C,72.67; H,7.05; N,11.55%.

$[\alpha]D^{20}$=−330 (c=0.3, CHCl$_3$)

EXAMPLE 184

(E)-(R)-1-[1-(2,3-Dihydrobenzofuran-5-yl)-1,3,4,9-tetrahydro-β-carbolin-2-yl]-3-(4-methylaminomethyl)-phenyl)propene-1-one The same method as employed in the preparation of Example 179 but starting from methylamine gave after recrystallization from MeOH:H$_2$O the title compound as a white powder in a 52% yield. MP: 129° C.

Analysis for $C_{30}H_{29}N_3O_2$. 1.1H$_2$O: Calculated: C,74.54; H,6.51; N,8.69; Found: C,74.68; H,6.57; N,8.59%.

$[\alpha\ D^{21}$=−288 (c=0.4, CHCl$_3$).

EXAMPLE 185

(E)-(R)-1-[1-(2,3-Dihydrobenzofuran-5-yl)-1,3,4,9-tetrahydro-g-carbolin-2-yl]-3-(4-isopropylamino-methyl)iphenyl)propene-1-one The same method as employed in the preparation of Example 179 but starting from isopropylamine gave after recrystallization from MeOH:H$_2$O the title compound as a white powder in a 47% yield. MP: 158° C.

Analysis for $C_{32}H_{33}N_3O_2$. 0.3H$_2$O: Calculated: C,77.33; H,6.81; N,8.45; Found: C,77.42; H,6.74; N,8.26%.

$[\alpha]D^{21}$=−319 (c=0.3, MeOH)

EXAMPLE 186

(E)-(R)-1-[1-(2 3-Dihydrobenzofuran-5-yl)-1,3,4,9-tetrahydro-3-carbolin-2-yl]-3-(4-dimethylamino-methyl)phenyl)propene-1-one The same method as employed in the preparation of Example 179 but using dimethylamine gave after recrystallization from iPrOH:H$_2$O the title compound as a white powder in a 34% yield. MP: 153–154° C.

Analysis for $C_{31}H_{31}N_3O_2$.0.2H$_2$O: Calculated: C,77.38; H,6.58; N,8.73; Found: C,77.4; H,6.49; N,8.61%.

$[\alpha]D^{21}$=−336 (c=0.3, MeOH).

EXAMPLE 187

(E)-(R)-1-[1-(2,3-Dihydrobenzofuran-5-yl)-1,3,4,9-tetrahydro-β-carbolin-2-yl]-3-[4-(3-dimethylamino-propoxy) phenyl]propene-1-one The same method as employed in the preparation of Example 79 but starting from Example 182 and dimethylaminopropyl chloride gave after recrystallization from CH$_3$CN the title compound as a white powder in a 53% yield. MP: 186° C.

Analysis for $C_{33}H_{35}N_3O_2$. 0.6H$_2$O: Calculated: C,74.44; H,6.85; N,7.89; Found: C,74.36; H,6.63; N,7.98%.

$[\alpha]D^{20}$=−326 (c=0.3, MeOH).

EXAMPLE 188

(E)-(R)-1-[1-(2,3-Dihydrobenzofuran-5-yl)-1,3,4,9-tetrahydro-β-carbolin-2-yl]-3-(4-(2-piperidin-1-ylethoxy)Tphenyl)ppropene-1-one The same method as employed in the preparation of Example 20 but starting from Intermediate 20 and Intermediate 55 gave after recrystallization from CH$_3$CN the title compound as white crystals in a 50% yield. MP: 210° C.

Analysis for $C_{35}H_{37}N_3O_3$: Calculated: C,76.75; H,6.81; N,7.67; Found: C,76.68; H,7.11; N,7.93%.

$[\alpha]D^{18.9}$=−290 (c=0.4, CHCl$_3$)

EXAMPLE 189

(E)-1-[1-(3,4-Methylenedioxyhepny)-1,3,4,9-tetrahydro-β-carbolin-2-yl)-3-(4-(2-piperidin-1-yl-ethoxy)phenyl]propene-1-one The same method as employed in the preparation of Example 20 but starting from Intermediate 55 gave after recrystallization from MeOH:H$_2$O the title compound as a beige solid in a 32% yield. MP: 102° C.

Analysis for $C_{34}H_{35}N_3O_4$. 0.6MeOH: Calculated: C,73.05; H,6.63; N,7.39; Found: C,73.24; H,6.87; N,7.02%.

EXAMPLE 190

(E)-(R)-[2-(4-{3-[1-(2,3-Dihydrobenzofuran-5-yl)-1,3,4,9-tetrahydro-β-carbolin-2-yl]-3-oxopropenyl}-phenoxy)ethyl]methylcarbamic acid, tertbutyl ester The same method as employed in the preparation of Example 20 but starting from Intermediate 20 and Intermediate 56 gave the title compound as a yellow powder in a 95% yield. MP: 110° C.

Analysis for $C_{36}H_{39}N_3O_5$. 0.3H$_2$O: Calculated: C,72.17; H,6.66; N,7.01; Found: C,71.9; H,6.86; N,7.17%.

EXAMPLE 191

(E)-(R)-1-[1-(2,3-Dihydrobenzofuran-5-yl)-1,3,4,9-tetrahdro-β-carbolin-2-yl1-3-[4-(2-methylaminoethoxy)phenyl]propene-1-one A solution of Example 190 (0.33 g, 0.55 mmol) in DCM (30 mL) w as treat ed with zinc bromide (0.63 g, 5 equiv.) for 16 hours at 30° C. A gumnmy solid was formed. Extraction with DCM:MeOH, washing with wa ter, drying over Na$_2$SO$_4$ and recrystallization from iPrOH gave the title compound as whit e crystals in a 98% yield. MP: 145° C.

Analysis for $C_{31}H_{31}N_3O_3$. 0.2H$_2$O: Calculated: C,74.89; H,6.37; N,8.45; Found: C,74,90; H,6.70; N,8.49%.

$[\alpha]D^{20}$=−337 (c=0.4, MeOH).

EXAMPLE 192

(E)-1-[1-(3,4-Methylenedioxyrphenyl)-1,3,4,9-tetrahydro-β-carbolin-2-yl)-3-(4-(2-piperidin-1-yl-ethoxy)-phenyl]propene-1-one The same method as employed in the preparation of Example 1, but starting from Intermediate 13 gave after recrysatllization from MeOH:H$_2$O the title compound as a beige solid in a 32% yield. MP: 102° C.

Analysis for $C_{34}H_{35}N_3O_4$. 0.6MeOH: Calculated: C,73, 05; H,6.63; N,7.39; Found: C,73.24; H,6.87; N,7.02%.

TABLETS FOR ORAL ADMINISTRATION
A. Direct Compression

| 1. | mg/tablet |
|---|---|
| Active Ingredient | 50.0 |
| Crospovidone USNF | 8.0 |
| Magnesium Stearate Ph Eur | 1.0 |
| Anhydrous Lactose | 141.0 |

The active ingredient was sieved and blended with the excipients. The resultant mix was compressed into tablets.

| 2. | mg/tablet |
|---|---|
| Active Ingredient | 50.0 |
| Colloidal Silicon Dioxide | 0.5 |
| Crospovidone | 8.0 |
| Sodium Lauryl Sulfate | 1.0 |
| Magnesium Stearate Ph Eur | 1.0 |
| Microcrystalline Cellulose USNF | 139.5 |

The active ingredient was sieved and blended with the excipients. The resultant mix was compressed into tablets.

B. Wet Granulation

| 1. | mg/tablet |
|---|---|
| Active Ingredient | 50.0 |
| Polyvinylpyrrolidone | 150.0 |
| Polyethylene glycol | 50.0 |
| Polysorbate 80 | 10.0 |
| Magnesium Stearate Ph Eur | 2.5 |
| Croscarmellose Sodium | 25.0 |
| Colloidal Silicon Dioxide | 2.5 |
| Microcrystalline Cellulose USNF | 210.0 |

The polyvinylpyrrolidone, polyethylene glycol, and polysorbate 80 were dissolved in water. The resultant solution was used to granulate the active ingredient. After drying, the granules were screened, then extruded at elevated temperatures and pressures. The extrudate was milled and/or screened, then was blended with the microcrystalline cellulose, croscarmellose sodium, colloidal silicon dioxide, and magnesium stearate. The resultant mix was compressed into tablets.

| 2. | mg/tablet |
|---|---|
| Active Ingredient | 50.0 |
| Polysorbate 80 | 3.0 |
| Lactose Ph Eur | 178.0 |
| Starch BP | 45.0 |
| Pregelatinized Maize Starch BP | 22.5 |
| Magnesium Stearate BP | 1.5 |

The active ingredient was sieved and blended with the lactose, starch, and pregelatinized maize starch. The polysorbate 80 was dissolved in purified water. Suitable volumes of the polysorbate 80 solution were added and the powders were granulated. After drying, the granules were screened and blended with the magnesium stearate. The granules were then compressed into tablets.

Tablets of other strengths can be prepared by altering the ratio of active ingredient to the other excipients.

FILM COATED TABLETS

The aforementioned tablet formulations were film coated.

| Coating Suspension | % w/w |
|---|---|
| Opadry White † | 13.2 |
| Purified Water Ph Eur | to100.0* |

*The water did not appear in the final product. The maximum theoretical weight of solids applied during coating was 20 mg/tablet.
† Opadry white is a proprietary material obtainable from Colorcon Limited, UK, which contains hydroxypropyl methylcellulose, titanium dioxide, and triacetin.

The tablets were film coated using the coating suspension in conventional film coating equipment.

CAPSULES

| 1. | mg/capsule |
|---|---|
| Active Ingredient | 50.0 |
| Lactose | 148.5 |
| Polyvinylpyrrolidone | 100.0 |
| Magnesium Stearate | 1.5 |

The active ingredient was sieved and blended with the excipients. The mix was filled into size No. 1 hard gelatin capsules using suitable equipment.

| 2. | mg/capsule |
|---|---|
| Active Ingredient | 50.0 |
| Microcrystalline Cellulose | 233.5 |
| Sodium Lauryl Sulphate | 3.0 |
| Crospovidone | 12.0 |
| Magnesium Stearate | 1.5 |

The active ingredient was sieved and blended with the excipients. The mix was filled into size No. 1 hard gelatin capsules using suitable equipment.

Other doses can be prepared by altering the ratio of active ingredient to excipient, the fill weight, and, if necessary, changing the capsule size.

| 3. | mg/capsule |
|---|---|
| Active Ingredient | 50.0 |
| Labrafil M1944CS | to1.0 ml |

The active ingredient was sieved and blended with the Labrafil. The suspension was filled into soft gelatin capsules using appropriate equipment.

Inhibitory Effect on cGMP-PDE

CGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 pg/ml 51-Nucleotidase, 1 mM EGTA, and 0.15 $\mu$M 8-[$H^3$]-cGMP. The enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 PM. Tests against other PDE enzymes using standard methodology also showed that compounds of the invention are highly selective for the cGMP-specific PDE enzyme.

cGMP Level Measurements

Rat aortic smooth muscle cells (RSMC), prepared according to Chamley et al., *Cell Tissue Res.*, 177, 503–522 (1977), were used between the 10th and 25th passage at confluence in 24-well culture dishes. Culture media was aspirated and replaced with PBS (0.5 ml) containing the compound tested at the appropriate concentration. After 30 minutes at 37° C., particulates guanylate cyclase was stimulated by addition of ANF (100 nM) for 10 minutes. At the end of incubation, the medium was withdrawn, and two extractions were performed by addition of 65% ethanol (0.25 ml). The two ethanolic extracts were pooled and evaporated until dryness, using a Speed-vac system. CGMP was measured after acetylation by scintillation proximity immunoassay (AMERSHAM). The $EC_{50}$ values are expressed as the dose-giving half of the stimulation at saturating concentrations.

Biological Data

The compounds according to the present invention were typically found to exhibit an $IC_5$. value of less than 500 nM and an ECso value of less than 5 $\mu$M. In vitro test data for representative compounds of the invention is given in the following table:

TABLE 1

In vitro results

| Example No. | $IC_{50}$ nM | $EC_{50}$ $\mu$M |
|---|---|---|
| 14 | 5 | 0.45 |
| 25 | 72 | 0.3 |
| 28 | 55 | 0.3 |
| 31 | 4 | 1 |
| 55 | 40 | 0.4 |
| 61 | 20 | 1.8 |
| 140 | 2 | 0.1 |
| 142 | 18 | 1.5 |
| 156 | 15 | <1 |
| 164 | 11 | 1.5 |
| 165 | 9 | <1 |
| 177 | 12 | <1 |
| 184 | 44 | 3 |
| 180 | 25 | 3.5 |
| 181 | 9 | 2 |
| 183 | 24 | 2 |
| 182 | 2 | <1 |
| 188 | 24 | <1 |
| 191 | 8 | <1 |

The hypotensive effects of compounds according to the invention as identified in Table 2 were studied in conscious spontaneously hypertensive rats (SHRs). The compounds were administered orally at a dose of 5 mg/kg in a mixture of 5% DMF and 95% olive oil. Blood pressure was measured from a catheter inserted in the carotid artery and recorded for five hours after administration. The results are expressed as Area Under the Curve (AUC from 0 to 5 hours, mmhg.hour) of the fall in blood pressure over time.

TABLE 2

In vivo results

| Example No. | SHR AUC PO (mmHG · h) |
|---|---|
| 14 | 128 |
| 25 | 72 |
| 26 | 102 |
| 28 | 114 |
| 31 | 86 |
| 55 | 97 |
| 61 | 95 |
| 112 | 71 |
| 122 | 76 |
| 140 | 105 |
| 142 | 74 |
| 156 | 57 |
| 175 | 52 |
| 177 | 100 |
| 181 | 77 |
| 188 | 86 |
| 191 | 84 |

What is claimed is:

1. A combination comprising:

(a) a compound of formula

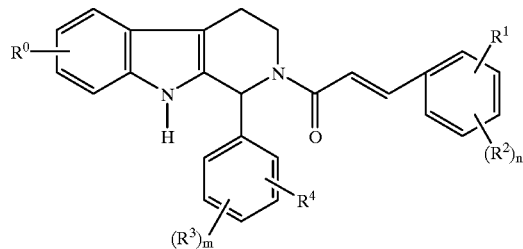

wherein $R^0$ represents hydrogen or halogen;

$R^1$ is selected from the group consisting of:
hydrogen,
$NO^2$
trifluoromethyl,
trifluoromethoxy,
halogen,
cyano,
a 5- or 6-membered heterocyclic group containing at least one heteroatom selected from oxygen, nitrogen and sulphur, and is optionally substituted by —C(=O)OR$^a$ or $C_{1-4}$ alkyl, $C_{1-6}$ alkyl optionally substituted by —OR$^a$, $C_{1-3}$alkoxy, C(=O) R$^a$, O—C (=O) R$^a$, C(=O) OR$^a$, $C_{1-4}$alkylene-C (=O)OR$^a$, O—$C_{1-4}$alkylene —C (=O) OR$^a$, $C_{1-4}$alkylene— O—$C_{1-4}$alkylene-C(=O)OR$^a$, C(=O)NR$^a$SO$_2$R$^c$, C(=O)$C_{1-4}$alkylene-Het, $C_{1-4}$alkylene-NR$^a$R$^b$, $C_{2-6}$alkenylene-NR$^a$R$^b$, C(=O)NR$^a$R$^b$, C(=O) NR$^a$R$^c$, C(=O)NR$^a$C$_{1-4}$alkylene-OR$^b$ C(=O) NR$^a$C$_{1-4}$alkylene-Het, OR$^a$ OC$_{2-4}$alkylene-NR$^a$R$^b$, OC$_{1-4}$alkylene-CH (OR$^a$) CH$_2$NR$^a$R$^b$, O—C$_{1-4}$ alkylene-Het, O—C$_{2-4}$alkylene-OR$^a$, O—C$_{2-4}$ alkylene-NRa—C(=O)—OR$^b$, NR$^a$R$^b$, NR$^a$C$_{1-4}$ alkylene-NR$^a$R$^b$, NR$^a$C(=O)R$^b$, NR$^a$C(=O) NR$^a$R$^b$, N(SO$_2$C$_{1-4}$alkyl)$_2$, NR$^a$(SO$_2$C$_{1-4}$alkyl), SO$_2$NR$^a$R$^b$, and OSO$_2$trifluoromethyl;

$R^2$ is selected from the group consisting of:
hydrogen,
halogen,

OR$^a$,
C$_{1-6}$alkyl,
NO$_2$, and
NR$^a$R$^b$, or R$^1$ and R$^2$ are taken together to form a 3- or 4-membered alkylene or alkenylene chain component of a 5- or 6-membered ring, optionally containing at least one heteroatom selected from the group consisting of oxygen, nitrogen and sulfur;

R$^3$ is selected from the group consisting of:
hydrogen,
halogen,
NO$_2$,
trifluoromethoxy,
C$_{1-6}$alkyl, and
C(=O)OR$^a$;

R$^4$ is hydrogen, or R$^3$ and R$^4$ are taken together to form a 3- or 4-membered alkylene or alkenylene chain component of a 5- or 6-membered ring, optionally containing at least one heteroatom;

Het represents a 5- or 6-membered heterocyclic group containing at least one heteroatom selected from the group consisting of oxygen, nitrogen, and sulfur, and is optionally substituted with C$_{1-4}$alkyl;

R$^a$ and R$^b$ can be the same or different, and are independently selected from hydrogen and C$_{1-6}$alkyl;

R$^c$ represents phenyl or C$_{4-6}$cycloalkyl, wherein the phenyl or C$_{4-6}$cycloalkyl can be optionally substituted by one or more halogen atoms, one or more —C(=O)OR$^a$, or one or more —OR$^a$;

n is an integer selected from 1, 2 and 3;

m is an integer selected from 1 and 2;

and pharmaceutically acceptable salts and solvates thereof; and (b) a second therapeutically active agent, for simultaneous, separate, or sequential use in the treatment of a condition where inhibition of a cGMP-specific PDE is of a therapeutic benefit.

2. A pharmaceutical formulation comprising a combination according to claim 1, together with a pharmaceutically acceptable diluent or carrier.

3. The combination of claim 1 wherein the condition is stable angina, unstable angina, variant angina, hypertension, pulmonary hypertension, chronic obstructive pulmonary disease, malignant hypertension, pheochromocytoma, congestive heart failure, acute respiratory distress syndrome, acute renal failure, chronic renal failure, atherosclerosis, a condition of reduced blood vessel patency, postpercutaneous transluminal coronary angioplasty, carotid angioplasty, myocardial infarction, post-bypass surgery graft stenosis, a peripheral vascular disease, a vascular disorder, Raynaud's disease, thrombocythemia, an inflammatory disease, stroke, bronchitis, chronic asthma, allergic asthma, allergic rhinitis, glaucoma, peptic ulcer, osteoporosis, preterm labor, benign prostatic hypertrophy, a gut motility disorder, or irritable bowel syndrome.

4. The combination of claim 1 wherein the condition is erectile dysfunction in a male or female animal.

5. The combination of claim 1 wherein the second therapeutically active agent comprises a vasodilator, prostaglandin E1, prostacyclin, α-adrenergic blocker, a mixed, α,β-blocker, an α$_2$-adrenergic blocker, an ACE inhibitor, an NEP inhibitor, a centrally acting dopaminergic agent, a vasoactive intestinal peptide, a calcium channel blocker, a thiazide, or a mixture thereof.

6. The combination of claim 5 wherein the vasodilator is selected from the group consisting of an organic nitrate, an organic nitrite, a thionitrite, a thionitrate, an S-nitrosothiol, a nitrosoprotein, a substituted furoxane, a substituted sydnonimine, a nitrosyl complex compound, nitric oxide, and mixtures thereof.

7. The combination of claim 5 wherein the vasodilator agent is selected from the group consisting of nitroglycerin, isosorbide dinitrate, pentaerythrityl tetranitrate, isosorbide-5-mono-nitrate, propatyl nitrate, trolnitrate, nicroandil, mannitol hexanitrate, inositol hexanitrate, N-[3-nitratopivaloyl]-6-cysteine ethyl ester, isoamyl nitrite, S-nitroso-N-acetyl-D, L-pencillamine, 1,2,5-oxadiazole-2-oxide, furazan-N-oxide, molsidomine, mesocarb, an iron nitrosyl compound, sodium nitroprusside, nitric oxide, and mixtures thereof.

8. The combination of claim 1 wherein the second therapeutically active compound is selected from the group consisting of prostaglandin E1, prostacyclin, apomorphine, yohimibine, phentolamine, prazocin, carvedilol, and mixtures thereof.

9. A method of treating a condition where inhibition of a cGMP-specific PDE is of therapeutic benefit, in a human or a nonhuman animal body, comprising administering to said body a therapeutically effective amount of a combination of claim 1.

10. The method of claim 9 wherein the cGMP-specific PDE is PDE5.

11. The method of claim 9 wherein the human animal is a human male or female.

12. The method of claim 9 wherein the treatment is an oral treatment.

13. A method of treating stable angina, unstable angina, variant angina, hypertension, pulmonary hypertension, chronic obstructive pulmonary disease, acute respiratory distress syndrome, chronic obstructive pulmonary disease, malignant hypertension, pheochromacytoma, congestive heart failure, acute renal failure, chronic renal failure, atherosclerosis, a condition of reduced blood vessel patency, a peripheral vascular disease, a vascular disorder, thrombocythemia, an inflammatory disease, myocardial infarction, stroke, bronchitis, chronic asthma, allergic asthma, allergic rhinitis, glaucoma, peptic ulcer, a gut motility disorder, pospercutaneous transluminal coronary angioplasty, carotid angioplasty, post-bypass surgery graft stenosis, osteoporosis, preterm labor, benign prostatic hypertrophy, or irritable bowel syndrome, in a human or nonhuman animal body, said method comprising administering to said body a therapeutically effective amount of a combination of claim 1.

14. The method of claim 13 wherein the compound is administered orally.

* * * * *

UNITED STATES PATENT AND TRADEMARK OFFICE
CERTIFICATE OF CORRECTION

PATENT NO. : 6,043,252
DATED : March 28, 2000
INVENTOR(S) : Agnes Bombrun

It is certified that error appears in the above-identified patent and that said Letters Patent is hereby corrected as shown below:

Column 3,
Line 26, after "$R^4$" and before "together" insert a blank space.

Column 7,
Line 12, replace "benzoicacid" with "benzoic acid".

Column 25,
Line 62, replace "Acid" with "acid".

Column 26,
Line 16, replace "Acid, Ethyl Ester" with "acid, ethyl ester".
Line 57, replace "Acid, Ethyl Ester" with "acic, ethyl ester".

Column 16,
Line 37, replace "60-adrenergic" with "α-adrenergic".

Column 21,
Line 19, replace "Acid, Methyl Ester" with "acid, methyl ester".

Column 27,
Line 4, replace "ester" with "ester".

Column 28,
Line 22, replace "Acid" with "acid".
Line 50, replace "Acid" with "acid".
Line 55, replace "Heterocyles" with "Heterocycles".

Column 29,
Line 15, replace "Acid" with "acid".
Line 26, replace "Acid" with "acid".
Line 46, replace "Acid" with "acid".
Line 57, replace "Acid" with "acid".

Column 30,
Line 13, replace "Acid" with "acid".
Line 53, replace "Acid" with "acid".

Column 31,
Line 15, replace "Acid" with "acid".

UNITED STATES PATENT AND TRADEMARK OFFICE
CERTIFICATE OF CORRECTION

PATENT NO. : 6,043,252
DATED : March 28, 2000
INVENTOR(S) : Agnes Bombrun

Page 2 of 5

It is certified that error appears in the above-identified patent and that said Letters Patent is hereby corrected as shown below:

Column 32,
Line 30, replace "Acid" with "acid".
Line 55, replace "Acid" with "acid".
Line 65, replace "Acid" with "acid".

Column 35,
Line 16, replace "1,3,4, 9" with "1,3,4,9" (delete blank space).

Column 36,
Line 15, replace "$C_{27}H_{21}N2O_2F_3$" with "$C_{27}H_{21}N_2O_2F_3$".
Line 64, replace "1,3,4,9" with "1,3,4,9" (delete blank space).

Column 37,
Line 7, replace "1,3,4, 9" with "1,3,4,9" (delete blank space).
Line 64, replace "acid" with "acid".

Column 39,
Line 32, replace "Acid, Methyl Ester" with "acid, methyl ester".

Column 40,
Line 10, replace "4 9" with "4,9".

Column 41,
Line 19, after "N.5.54" and before "." insert "%".

Column 42,
Line 15, replace "tetrahydro-3-carbolin-β-yl]" with "tetrahydro-β-carbolin 2-yl]".

Column 43,
Line 14, replace "crytals" with "crystals".
Line 20, replace "Methylenedioxyohenyl" with "Methylenedioxyphenyl".
Line 54, replace "$C2_7H_{22}N_2O_5$" with "$C_{27}H_{22}N_2O_5$".
Line 60, replace "1 3,4,9" with "1,3,4,9".

Column 44,
Line 37, replace "f4" with "{4".
Line 42, delete [and] (first occurrence).
Line 44, after "as" and before "white" delete [a].

UNITED STATES PATENT AND TRADEMARK OFFICE
CERTIFICATE OF CORRECTION

PATENT NO. : 6,043,252
DATED : March 28, 2000
INVENTOR(S) : Agnes Bombrun

It is certified that error appears in the above-identified patent and that said Letters Patent is hereby corrected as shown below:

Column 45,
Line 22, replace "A" with "B".

Column 46,
Line 30, af ter "phenyl" and before "propene" delete [1].
Line 4, replace "tetrahydro-3-carbolin-β-yl]" with "tetrahydro-β-carbolin-2-yl]".

Column 48,
Line 21, after "carbonyl)" and before "phenyl)" delete [r].
Line 65, replace "260-2640C." with 260-264°C."

Column 49,
Line 23, replace "benzoicacid" with "benzoic acid".
Line 5, replace "benzoicacid" with "benzoic acid".
Line 57, rplace "1,3,4 9" with "1,3,4,9".
Line 59, after "phenyl)" and before "propene" delete [r].
Line 65, replace "tic" with "tlc".

Column 52,
Line 27, replace "251-252δC." with "251-252°C".
Line 40, replace ""169δC." with "169°C."

Column 53,
Line 65, replace "ipropene-1-one" with "propene-1-one".

Column 54,
Line 36, replace "1,34,9" with "1,3,4,9".
Line 57, replace "136-1380C." with "136-138°C."

Column 55,
Line 31, replace "(4-methyliminomethylphenyl)" with "(-4-Methylaminomothylphenyl)".
Line 59, replace "$C_{21}H_2QN3O_5$" with "$C_{28}H_{25}N_3O_5$".

Column 56,
Line 37, replace "(3,4-Methylenedioxyrhenyl)" with "(3,4-Methylenedioxyphenyl)".
Line 50, replace "8" with "β".

UNITED STATES PATENT AND TRADEMARK OFFICE
CERTIFICATE OF CORRECTION

PATENT NO. : 6,043,252
DATED : March 28, 2000
INVENTOR(S) : Agnes Bombrun

Page 4 of 5

It is certified that error appears in the above-identified patent and that said Letters Patent is hereby corrected as shown below:

Column 58,
Line 9, replace "172-1730C" with "172-173°C."
Line 50, replace "1.3.49" with "1,3,4,9".

Column 59,
Line 26, replace "a" with "an".

Column 60,
Line 15, replace "β2361" with "622361".
Line 34, replace "(3,4-Methylenedioxy-henyl)" with "(3,4-Methylenedioxyphenyl".

Column 61,
Line 21, replace "4,9-tetrahydro-g-carbolin-2-yl)" with "(4,9-tetrahydro-β-carbolin-2-yl)".
Line 61, after "dimethylaminoethoxy)" and before "phenyl)" delete [i].

Column 64,
Line 11, after "phenyl)" and before "propene" delete [i].
Line 37, replace "tetrahydro-g-carbolin-2-yl]" with "tetrahydro-β-carbolin-2-yl]".
Line 65, after "methoxy)" and before "phenyl)" delete [r].

Column 65,
Line 25, replace "1-methylethoxy)pDhenyl)" with "1-methylethoxy)phenyl".
Line 51, after "phenyl)" and before "propene" delete [p].

Column 67,
Line 47, replace "(3,4-Methylenedioxyrhenyl)" with "(3,4-Methylenedioxyphenyl)".

Column 68,
Line 4, replace "$C_{27}H_{22}FN3O_4$" with "$C_{27}H_{22}FN_3O_4$".
Line 9, replace "tetra-hydro-β-carbolin-2-yl1-3-" with "tetra-hydro-β– carbolin-2-yl]-3-".
Line 38, after "ylethoxy)" and before "phenyl)" delete [r].

Column 69,
Line 11, after "2-hydroxypropoxy)" and before "phenyl)" delete [T].

UNITED STATES PATENT AND TRADEMARK OFFICE
CERTIFICATE OF CORRECTION

PATENT NO. : 6,043,252
DATED : March 28, 2000
INVENTOR(S) : Agnes Bombrun

It is certified that error appears in the above-identified patent and that said Letters Patent is hereby corrected as shown below:

Column 71,
Line 24, after "methyl)" and before "phenyl)" delete [i].
Line 65, after "ylethoxy)" and before "phenyl)" delete [T].

Column 72,
Line 11, replace (3,4-Methylenedioxyhepny)" with "(3,4-Methylenedioxyphenyl)".
Line 44, replace "w as treated" with "was treated".
Line 48, replace "whit e" with "white".

Signed and Sealed this

Thirtieth Day of October, 2001

Attest:

NICHOLAS P. GODICI
Attesting Officer    Acting Director of the United States Patent and Trademark Office